US011813370B2

(12) United States Patent
Romo et al.

(10) Patent No.: US 11,813,370 B2
(45) Date of Patent: *Nov. 14, 2023

(54) STERILIZATION UNITS, SYSTEMS, AND METHODS

(71) Applicant: Leviant, Inc., Hawthorne, NY (US)

(72) Inventors: Luis F. Romo, New York, NY (US); Arto Cinoglu, Bohemia, NY (US); David Moses, Bohemia, NY (US)

(73) Assignee: LEVIANT, INC., Westport, CT (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/148,873

(22) Filed: Jan. 14, 2021

(65) Prior Publication Data
US 2021/0244834 A1    Aug. 12, 2021

Related U.S. Application Data

(63) Continuation of application No. 16/454,385, filed on Jun. 27, 2019, now Pat. No. 10,894,102, which is a (Continued)

(51) Int. Cl.
*G01N 23/00* (2006.01)
*A61N 5/00* (2006.01)
(Continued)

(52) U.S. Cl.
CPC ................... *A61L 2/10* (2013.01); *A61L 2/24* (2013.01); *A61L 9/20* (2013.01); *A61L 2202/11* (2013.01);
(Continued)

(58) Field of Classification Search
CPC ..... A61L 2/00; A61L 9/00; A61L 9/18; A61L 9/20
(Continued)

(56) References Cited

U.S. PATENT DOCUMENTS

| 4,448,750 A | 5/1984 | Fuesting |
| 5,080,209 A | 1/1992 | Yurko |

(Continued)

FOREIGN PATENT DOCUMENTS

| AU | 2013361188 A1 | 7/2015 |
| AU | 2013361188 B2 | 5/2017 |

(Continued)

OTHER PUBLICATIONS

"U.S. Appl. No. 14/744,461, Non Final Office Action dated Jul. 1, 2016", 15 pgs.
(Continued)

*Primary Examiner* — Monzer R Chorbaji
(74) *Attorney, Agent, or Firm* — NIXON PEABODY LLP

(57) ABSTRACT

A Sterilization Unit includes: a UV-C radiation source configured to emit UV-C radiation; and a room partition selectably configurable between two or more different partition geometrics and configured, in each of the two or more different partition geometrics, to (a) physically separate floor space of a room into sterilization target area and a non-target area, and (b) direct the UV-C radiation to the target area from at least two different directions while shielding the non-target area from the UV-C radiation.

21 Claims, 31 Drawing Sheets

Related U.S. Application Data continuation of application No. 15/860,493, filed on Jan. 2, 2018, now Pat. No. 10,376,604, which is a continuation of application No. 15/491,856, filed on Apr. 19, 2017, now abandoned, which is a continuation of application No. 14/744,461, filed on Jun. 19, 2015, now Pat. No. 9,675,720, which is a continuation of application No. PCT/US2013/076717, filed on Dec. 19, 2013.

(60) Provisional application No. 61/776,914, filed on Mar. 12, 2013, provisional application No. 61/739,098, filed on Dec. 19, 2012.

(51) Int. Cl.
| | |
|---|---|
| *G02B 5/00* | (2006.01) |
| *A61L 2/10* | (2006.01) |
| *A61L 9/20* | (2006.01) |
| *A61L 2/24* | (2006.01) |

(52) U.S. Cl.
CPC ..... *A61L 2202/121* (2013.01); *A61L 2202/16* (2013.01); *A61L 2202/25* (2013.01)

(58) Field of Classification Search
USPC .......... 422/22, 24; 250/455.11, 492.1, 505.1
See application file for complete search history.

(56) References Cited

U.S. PATENT DOCUMENTS

| | | |
|---|---|---|
| 5,145,366 A | 9/1992 | Janhunen |
| 5,272,848 A | 12/1993 | Maas |
| 5,533,305 A | 7/1996 | Bielecki |
| 5,891,399 A | 4/1999 | Owesen |
| 7,829,016 B2 | 11/2010 | Deal et al. |
| 8,067,750 B2 | 11/2011 | Deal |
| 9,107,973 B1 | 8/2015 | Robinson et al. |
| 9,675,720 B2 * | 6/2017 | Romo ................ A61L 2/24 |
| 10,376,604 B2 * | 8/2019 | Romo ................ A61L 2/10 |
| 10,894,102 B2 | 1/2021 | Romo et al. |
| 2002/0085947 A1 | 7/2002 | Deal |
| 2003/0018373 A1 | 1/2003 | Eckhardt et al. |
| 2003/0202902 A1 | 10/2003 | Elliott |
| 2004/0056201 A1 | 3/2004 | Fink et al. |
| 2005/0201910 A1 | 9/2005 | Shau et al. |
| 2006/0175554 A1 | 8/2006 | Riddell |
| 2007/0157385 A1 | 7/2007 | Guy et al. |
| 2007/0194255 A1 | 8/2007 | Garcia et al. |
| 2007/0274879 A1 | 11/2007 | Millikin |
| 2008/0056933 A1 | 3/2008 | Moore et al. |
| 2008/0178543 A1 | 7/2008 | Maas |
| 2009/0272029 A1 | 11/2009 | Aiking et al. |
| 2011/0044848 A1 | 2/2011 | Wright |
| 2011/0169646 A1 | 7/2011 | Raichman |
| 2011/0172810 A1 | 7/2011 | Mlodzinski et al. |
| 2011/0215261 A1 | 9/2011 | Lyslo et al. |
| 2011/0243789 A1 | 10/2011 | Roberts |
| 2011/0259864 A1 | 10/2011 | Galietti |
| 2012/0074334 A1 | 3/2012 | Milligan |
| 2013/0002445 A1 | 1/2013 | Stibich et al. |
| 2015/0086420 A1 | 3/2015 | Trapani |
| 2015/0192689 A1 | 7/2015 | Li et al. |
| 2015/0246148 A1 | 9/2015 | Blechschmidt et al. |
| 2015/0367008 A1 | 12/2015 | Romo et al. |
| 2016/0021860 A1 | 1/2016 | Fortney |
| 2016/0128526 A1 | 5/2016 | Dobrinsky et al. |
| 2016/0354503 A1 | 12/2016 | Hutchens et al. |
| 2017/0112953 A1 | 4/2017 | Dayton et al. |
| 2017/0112954 A1 | 4/2017 | Dayton |
| 2017/0216468 A1 | 8/2017 | Romo et al. |
| 2017/0304473 A1 | 10/2017 | Farren et al. |
| 2017/0367785 A1 | 12/2017 | Munari |
| 2018/0140727 A1 | 5/2018 | Romo et al. |
| 2018/0256764 A1 | 9/2018 | Kreitenberg |
| 2019/0365938 A1 | 12/2019 | Romo et al. |

FOREIGN PATENT DOCUMENTS

| | | | |
|---|---|---|---|
| AU | 2017213522 B2 | 7/2019 | |
| CN | 2155875 Y | 2/1994 | |
| CN | 2621044 Y | 6/2004 | |
| CN | 2688291 Y | 3/2005 | |
| DE | 20016160 U1 | 11/2000 | |
| EP | 2934606 A1 | 10/2015 | |
| EP | 2772272 B1 | 3/2017 | |
| EP | 3354289 A1 | 8/2018 | |
| JP | 04091794 U | 8/1992 | |
| JP | H07289616 A | 11/1995 | |
| JP | 2001327590 A | 11/2001 | |
| JP | 2005168858 | 6/2005 | |
| JP | 2016506274 A | 3/2016 | |
| JP | 2017532138 A | 11/2017 | |
| JP | 6385363 B2 | 8/2018 | |
| WO | WO9317195 A1 | 9/1993 | |
| WO | WO9639820 A1 | 12/1996 | |
| WO | 2001051098 A1 | 7/2001 | |
| WO | WO0151098 A1 | 7/2001 | |
| WO | WO2008010684 A1 | 1/2008 | |
| WO | WO 2010/115183 | * 10/2010 | ............... A61L 2/10 |
| WO | WO2010115183 A1 | 10/2010 | |
| WO | WO2012142427 A1 | 10/2012 | |
| WO | WO2014100493 A1 | 6/2014 | |
| WO | 2019143699 A1 | 7/2019 | |

OTHER PUBLICATIONS

"U.S. Appl. No. 14/744,461, Notice of Allowance dated Jan. 23, 2017", 5 pgs.
"U.S. Appl. No. 15/491,856, Non Final Office Action dated Jul. 3, 2017", 11 pgs.
"U.S. Appl. No. 15/860,493, Final Office Action dated Dec. 6, 2018", 12 pgs.
"U.S. Appl. No. 15/860,493, Non Final Office Action dated Feb. 23, 2018", 11 pgs.
"U.S. Appl. No. 15/860,493, Notice of Allowance dated Mar. 27, 2019", 8 pgs.
"U.S. Appl. No. 15/860,493, Response filed Aug. 23, 2018 to Non Final Office Action dated Feb. 23, 2018", 14 pgs.
"U.S. Appl. No. 15/860,493, Response to Final Office Action dated Dec. 6, 2018 filed Mar. 5, 2019", 17 pgs.
"European Application Serial No. 13864597.3, Extended European Search Report dated Jul. 13, 2016", 8 pgs.
"European Application Serial No. 18157608.3, Extended European Search Report dated Apr. 24, 2018", 7 pgs.
"European Application Serial No. 18157608.3, Response Filed Feb. 1, 2019 to Extended European Search Report dated Apr. 24, 2018", 56 pgs.
"International Application Serial No. PCT/US2013/076717, International Search Report dated Apr. 1, 2014", 4 pgs.
"International Application Serial No. PCT/US2013/076717, Written Opinion dated Apr. 1, 2014", 9 pgs.
"U.S. Appl. No. 14/744,461, 312 Amendment filed Apr. 19, 2017", 14 pgs.
"U.S. Appl. No. 14/744,461, PTO Response to Rule 312 Communication dated May 8, 2017", 2 pgs.
"U.S. Appl. No. 14/744,461, Response filed Jan. 3, 2017 to Non Final Office Action dated Jul. 1, 2016", 17 pgs.
"Australian Application Serial No. 2013361188, Examination Report dated Aug. 31, 2016", 3 pgs.
"Australian Application Serial No. 2013361188, Response filed Apr. 13, 2017 to Examination Report dated Aug. 31, 2016", 3 pgs.
"Australian Application Serial No. 2017213522, First Examination Report dated May 8, 2018", 3 pgs.
"European Application Serial No. 13864597.3, Communication Pursuant to Article 94(3) EPC dated Mar. 7, 2018", 4 pgs.

(56) References Cited

OTHER PUBLICATIONS

"European Application Serial No. 13864597.3, Intention to Grant dated Apr. 24, 2017", 102 pgs.
"European Application Serial No. 13864597.3, Intention to Grant dated Oct. 11, 2017", 4 pgs.
"European Application Serial No. 13864597.3, Response filed Feb. 8, 2017 to Extended European Search Report dated Jul. 13, 2016" 15 pgs.
"European Application Serial No. 13864597.3, Response filed Feb. 21, 2018 to Intention to Grant dated Oct. 11, 2017", 22 pgs.
"European Application Serial No. 13864597.3, Response filed Apr. 30, 2018 to Communication Pursuant to Article 94(3) EPC dated Mar. 7, 2018" 34 pgs.
"European Application Serial No. 13864597.3, Response filed Aug. 14, 2017 to Intention to Grant dated Apr. 24, 2017", 11 pgs.
"International Application Serial No. PCT/US2013/076717, International Preliminary Report on Patentability dated Jul. 2, 2015" 11 pgs.
"Japanese Application Serial No. 2015-549741, Notice of Allowance dated Jul. 9, 2018", w/English Translation, 5 pgs.
"Japanese Application Serial No. 2015-549741, Office Action dated Dec. 15, 2017", w/English Translation 7 pgs.
"Japanese Application Serial No. 2015-549741, Voluntary Amendment filed Dec. 16, 2016", w/English Translation, 17 pgs.
Japanese Office Action in Japanese Application No. 2018-148410, dated May 18, 2020, 5 pages (with English Translation).

\* cited by examiner (SECTION A-A)

STERILIZATION UNITS, SYSTEMS, AND METHODS

CROSS-REFERENCE TO RELATED APPLICATIONS

This application is a continuation of U.S. patent application Ser. No. 16/454,385, filed Jun. 27, 2019, now allowed, which is a continuation of U.S. patent application Ser. No. 15/860,493, filed Jan. 1, 2018, now U.S. Pat. No. 10,376,604, which is a continuation of U.S. patent application Ser. No. 15/491,856, filed Apr. 19, 2017, now abandoned, which is a continuation of U.S. patent application Ser. No. 14/744,461, filed Jun. 19, 2015, now U.S. Pat. No. 9,675,720, which claims the benefit of International PCT Application No. PCT/US2013/076717, filed Dec. 19, 2013, which claims priority to U.S. Provisional Patent Application No. 61/739,098, filed Dec. 19, 2012, and U.S. Provisional Patent Application No. 61/776,914, filed Mar. 12, 2013; the entire contents of each of which is incorporated herein by reference.

FIELD

Some example embodiments of the present invention generally relate to a sterilization device and to methods for sterilizing. More particularly, some example embodiments of the present invention relate to a device for sterilization of a space, surface, or structure, and to methods of sterilizing a space, surface, or structure utilizing the device.

BACKGROUND

Microbial contamination is a global concern within many industries, especially in the healthcare industry. It costs countries billions of dollars in expenses per year, and, more importantly, the contaminant pathogens plague private and public (e.g. healthcare) settings and surroundings. Ultimately, these contaminated surroundings lead to infections and can ultimately lead to death.

Further, many communicable diseases are transmitted through contact with contaminated areas. The types and seriousness of communicable diseases transmitted in this manner are varied. For example, viral and bacterial diseases alike can be communicated by physical contact with surfaces upon which the infectious agents reside. Further, there is an increasing awareness and concern worldwide of the possibility of widespread outbreaks, or even pandemics, of communicable disease; these concerns stem in part from possible spontaneous mutations of influenza and other viruses, as well as the increasing resistance of bacterial strains to conventional and even newly-developed and powerful antibiotics.

Thus, a need exists for improved sterilization devices and methods for sterilization which may, inter alia, assist in providing sterilized spaces, surfaces, and/or structures, and in combating the spread of diseases that may be communicated via physical contact with infected areas.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY

In accordance with example embodiments, the need for improved sterilization devices and methods is satisfied. Example embodiments may address one or more of the problems and deficiencies of the art discussed above. However, example embodiments may additionally or alternatively prove useful in addressing other problems and deficiencies in a number of technical areas. Therefore, the scope of embodiments of the present invention should not necessarily be construed as limited to addressing any of the particular problems or deficiencies discussed herein.

Some embodiments of the presently-disclosed sterilization device and methods have several features, no single one of which is solely responsible for their desirable attributes. Without limiting the scope of these devices and methods as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. In accordance with some embodiments, these advantages may include, without limitation: providing improved sterilization devices and methods for sterilization which may, inter alia, assist in providing sterilized spaces, surfaces, and/or structures; providing a customizable sterilization exposure area; allowing for appropriate exposure, dosage, and sterilization processes of any spaces, surfaces, and/or structures in need of sterilization; combating the spread of diseases that may be communicated via physical contact with infected areas; providing devices and methods that have highly effective UV-C for sterilization; providing devices and methods that are easily integratable within, e.g., healthcare logistics; and allowing for sterilization in a fast, safe, and effective manner. Additional non-limiting unique capabilities of some embodiments of the invention include: being self-sterilizable; being buildable and stackable to maximize sterilization field; ability to operate a sterilization device while users are present with the invention in the same room; eradication of 99.9% of microorganisms; ability to use the device to partition rooms and allow use of sections of the room that are not under direct sterilization; ability of the device to form an enclosure within itself (e.g., a contained sterilization area); being expandable and contractible; portability; ability to prevent user UV-C contamination/exposure; ability to accommodate to a multitude of exposure angles; ability to function in an open area (e.g., large rooms or hospital wards), or more contained area (e.g., corners, hallways, etc.).

In accordance with example embodiments, a sterilization device includes: a UV-C radiation source configured to emit UV-C radiation; and a room partition selectably configurable between two or more different partition geometries and configured, in each of the two or more different partition geometries, to (a) physically separate floor space of a room into a sterilization target area and a non-target area, and (b) direct the UV-C radiation to the target area from at least two different directions while shielding the non-target area from the UV-C radiation.

The UV-C radiation source may include a plurality of UV-C radiation emitting devices.

The UV-C radiation emitting devices may each include one or more light elements configured to generate UV-C radiation.

The UV-C radiation emitting devices may be mounted to the room partition.

The sterilization device may be a free-standing unit configured to be stably self-supported on a flat floor surface when the room partition is in an upright position.

The room partition may include casters to allow the room partition to be rolled between multiple configurations.

The room partition may be selectably reconfigurable between a plurality of shapes corresponding to different delineations between the target area and the non-target area.

The room partition may include first and second panels, each configured to form a UV-C radiation barrier between the target area and the non-target area and each having a first face configured to face toward the non-target area and a second face configured to face toward the target area.

The sterilization device may further include an electronic control system including a computer processor configured to execute computer-readably instructions to perform at least one sterilization operation.

The processor may be configured to selectively control the radiation intensity and duration of the radiation source for the sterilization operation.

The processor may be configured to adjust power supplied to the radiation source based on age-based degradation of the radiation source in order to provide consistency of UV-C light intensity from the radiation source.

The processor may be configured to selectively control the plurality of UV-C radiation emitting devices dependent upon which of the plurality of shapes the partition is configured to have.

The processor may be configured to power on a subset of the UV-C radiation emitting devices while one or more of the other UV-C radiation emitting devices is powered off.

The processor may be configured to receive a signal from one or more sensors configured to measure UV-C light exposure in the target area.

The processor may be configured to receive at least one signal from a sensor configured to identify at least one of (a) an item in the target area, and (b) a physical location of the target area.

The at least one signal may be generated based on at least one RFID tag disposed on the item in the target area and/or at the physical location of the target area.

The sterilization device according to any one of claims 9 to 16, wherein the processor includes multiple underlying processors.

The control system may be physically configured as part of the room partition.

The control system may further include a transceiver configured to send and receive information over a communication network.

The control system may be configured to transmit information providing the identity of at least one of (a) an item in the target area and (b) the location of the target area.

The information transmission may indicate that the item or target area location has been sterilized by the sterilization unit.

The processor may be configured to receive via the transceiver and process information that identifies a target area and/or item that has been flagged as needing sterilization.

In accordance with example embodiments, a method includes: identifying by a computer processor a set of beds in a healthcare facility; determining, by a computer processor, a sterilization status of the respective beds based on RFID chips assigned to the respective beds; and sterilizing at least one of the beds based on the determined sterilization status of the at least one of the beds.

The identifying and the determining may be performed by the same computer processor or different computer processors.

In accordance with example embodiments, a sterilization device or unit includes: a UV-C source configured to emit UV-C radiation; a first panel including a first side, and an opposite second side configured to direct a first portion of the UV-C radiation outwardly away from the second side, the first panel configured to block UV-C radiation from passing outwardly from the first side of the first panel; and a second panel including a first side, and an opposite second side configured to direct a second portion of the UV-C radiation outwardly away from the second side, the second panel configured to block UV-C radiation from passing outwardly from the first side of the second panel; wherein the second panel is coupled to the first panel such that the first panel and the second panel form a free-standing sterilization unit, and an angle between the first panel and the second panel is adjustable to allow the sterilization device to conform to different spaces to be sterilized.

The UV-C source may include a plurality of UV-C radiation emitters.

One or more of the UV-C radiation emitters may be mounted to the first panel and/or the second panel.

The angle between the first panel and the second panel may be adjustable from a first angle that is less than 5 degrees to a second angle that is greater than 40 degrees.

The angle between the first panel and the second panel may be adjustable from a first angle that is less than 5 degrees to a second angle that is greater than 170 degrees.

At least one of the first panel and the second panel includes a window configured to allow visual inspection of an area to be sterilized from a position that is not exposed to UV-C radiation generated by the UV-C radiation source.

The sterilization device may further include a third panel including a first side, and an opposite second side configured to direct a third portion of the UV-C radiation outwardly from the second side, the third panel configured to block UV-C radiation from passing outwardly from the first side of the panel, wherein the third panel is coupled to the first panel and slideable along a width of the first panel between a proximal position and a distal position.

The sterilization device may further include a slide mechanism via which the third panel is coupled to the first panel, the slide mechanism comprising a track and a slide block configured to move along the track.

The slide block may be configured to rotate relative to the track to allow the third panel to rotate relative to the first panel in a plane that includes the third panel.

The third panel may have a range of rotation of, e.g., greater than 3 degrees relative to the first panel. For example, the third panel may have a range of rotation of greater than 5 degrees relative to the first panel.

The slide block may be rotatable relative to the track due to clearance between the slide block and one or more guide rails of the track.

The third panel may be configured to rotate, when in the distal position, between a parallel orientation relative to the first panel and an angled orientation relative to the first panel.

The third panel, when in the angled orientation, may form, e.g., a right angle relative to the first panel.

The sterilization device may further include: a slide mechanism via which the third panel is coupled to the first panel, the slide mechanism comprising a track and a slide block configured to move along the track; and a pivot joint coupled to the slide block and about which the third panel is configured to rotate relative to the first panel between the parallel orientation and the transverse orientation.

The pivot joint may include a locking mechanism to releasably lock the angle of rotation of the third panel relative to the first panel.

The third panel may be constrained from rotating from the parallel position when the third panel is in the proximal position.

The sterilization device may be configurable into a U-shaped configuration in which the third panel and the second panel are at right angles relative to the first panel.

The sterilization device may further include a fourth panel including a first side, and an opposite second side configured to direct a fourth portion of the UV-C radiation outwardly from the second side, the fourth panel configured to block UV-C radiation from passing outwardly from the first side.

The sterilization device may be configurable into a multi-walled enclosure, each of the first panel, the second panel, the third panel, and the fourth panel constituting a respective one of the four walls such that the second side of each of the first panel, the second panel, the third panel, and the fourth panel is directed to the interior of the multi-walled enclosure.

The fourth panel may be slideably and rotatably coupled to the second panel.

The sterilization device may further include an extension arm, the sterilization device configurable into a C-shaped configuration to receive a hospital bed, with the first and second panels along a first longitudinal side of the bed, the third and fourth panels along the ends of the bed and the extension arm is extended across the bed and downward such that the extension arm configured to emit UV-C radiation from the longitudinal side of the bed that is opposite the first and second panels.

In accordance with example embodiments, a sterilization unit or device includes: a first panel; a second panel coupled to the first panel; a third panel coupled to the first panel; and a fourth panel coupled to the second panel, wherein each of the first panel, the second panel, the third panel, and the fourth panel includes a first side, an opposite second side, and a UV-C radiation source configured to emit UV-C radiation outwardly from the second side, each of the first panel, the second panel, the third panel, and the fourth panel configured to block UV-C radiation from being passing outwardly away from the respective first side, wherein the third panel is slideable between a proximal and distal position relative to the first panel and, in the distal position, pivotable relative to the first panel, wherein the fourth panel is slideable between a proximal and distal position relative to the second panel and, in the distal position, pivotable relative to the second panel, and wherein the sterilization device is selectably configurable among a plurality of configurations including a first configuration in which the second side of the first panel faces the second side of the second panel and a second configuration in which the second panel is at a right angle or greater relative to the first panel.

The first panel may be parallel to the second panel in the first configuration of the device.

In the second configuration of the device, the third panel may be parallel to the first panel and the fourth panel may be parallel to the second panel.

The sterilization device may further include a third configuration in which the third panel is oriented at an angle of 30 degrees or greater relative to the first panel.

The sterilization device may be positionable as a room partition to emit UV-C radiation into a corner of a room while blocking UV-C radiation from other portions of the room.

In the third configuration, the fourth panel may be oriented at an angle of, e.g., 30 degrees or greater relative to the second panel.

In the third configuration, the device may be positionable adjacent to a straight wall to enclose a space between the wall and the device such that the device emits UV-C radiation into the space while blocking UV-C radiation from being emitted away from the space.

In the second configuration, the third panel may be parallel to the first panel, the fourth panel may be parallel to the second panel, and the device may be positionable as a room partition to emit UV-C radiation into a corner of a room while blocking UV-C radiation from other portions of the room.

The sterilization device may further include a cantilevered arm comprising a radiation source configured to emit UV-C radiation, the cantilevered arm moveable between a folded position and an extended position.

In the second configuration of the device, the first panel may be parallel to the second panel, the third panel may be perpendicular to the first panel, the fourth panel may be perpendicular to the second panel, and the cantilevered arm may be in the extended position.

In the second configuration, the device may define a space to receive a hospital bed such that the hospital bed is irradiated with UV-C light from four different sides, corresponding respectively to (a) the first and second panels, (b) the third panel, (c) the fourth panel, and (d) the cantilevered arm.

The sterilization device may be modular such that a free end of the third panel is configured to mate with a free end of a fourth panel of a like device, and a free end of the fourth panel is configured to mate with a free end of a third panel of a like device.

The sterilization device may further include an electronic control system configured to selectably control the amount of UV-C radiation emitted from at least one of the panels based at least in part on the configuration of the panels.

In accordance with example embodiments, a method includes: providing a plurality of UV-C radiation-emitting panels to form a partitioned floor space in a room; and emitting UV-C radiation from the panels to sterilize the partitioned floor space while blocking the UV-C radiation from floor space outside the partitioned floor space.

The partitioned floor space may be part of a hospital room.

The portioned floor space may include a hospital bed.

The plurality of UV-C radiation-emitting panels may be part of a mobile unit configured to sterilize temporary medical field operations remote from a hospital.

These and other features and advantages of example embodiments of the invention will become apparent from the following detailed description of the various aspects of the invention taken in conjunction with the appended claims and the accompanying drawings.

BRIEF DESCRIPTION OF THE DRAWINGS

FIG. 34 shows a block diagram of an exemplary cloud computing environment according to example embodiments.

FIG. 35 shows an example of a computing device and a mobile computing device in connection with example implementations.

FIG. 36 schematically shows, in connection with an example, of a contaminated field surrounded by a sterilization unit of an example implementation.

DETAILED DESCRIPTION OF THE INVENTION

Figure 1:
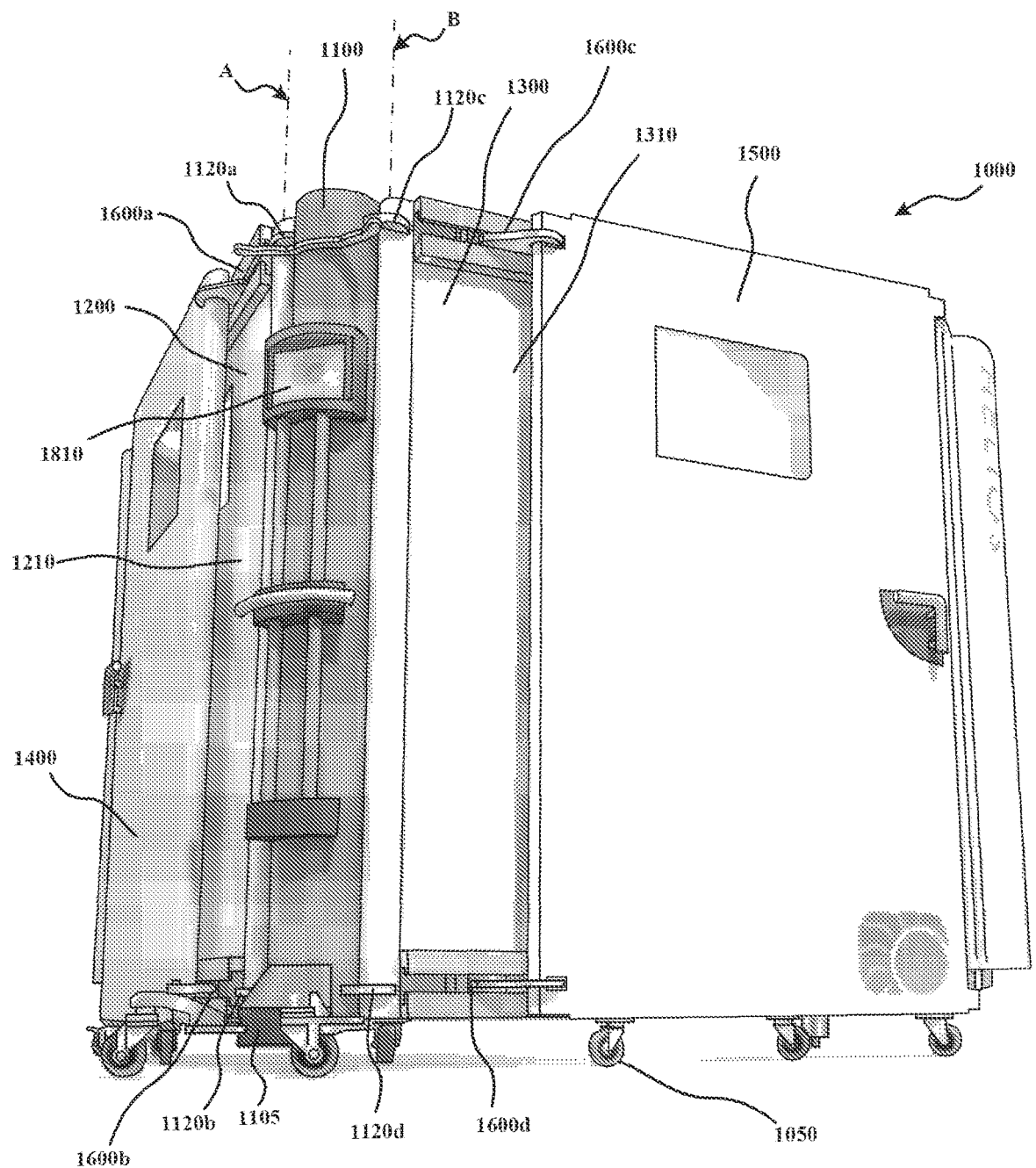
FIG. 1 a perspective view of a sterilization unit in accordance with an example embodiment.

Some example embodiments of the present invention are generally directed to, inter alia, a sterilization device and to methods for sterilizing.

Although the present invention entails many different embodiments, certain embodiments of the invention are shown and described. It should be understood, however, that the present disclosure is not intended to limit the invention to the embodiments illustrated.

Reference numerals retain their designation and meaning for the same or like or similar elements throughout the various drawings except to the extent indicated otherwise.

In one aspect, example embodiments of the invention relate to a device for sterilization of a space, surface, or structure. The device may include a sterilization structure that has an outer first face and an inner second face, where the inner face comprises one or more UV-C radiation sources.

In some embodiments, the central sterilization structure comprises a first panel and a second panel, wherein the first and second panels are attached to one another to form the central sterilization structure, In some embodiments, the central sterilization structure is a structure comprising a first panel and a second panel, wherein the first and second panels are attached to another to form the central sterilization structure. As used herein, the term "attached" refers to both direct and indirect attachments. So, for example, in the case of the first and second panels of the central sterilization structure of the device of the invention, "attached to one another" means that the first and second panels are attached to one another either directly or indirectly (e.g., through any acceptable joining structure, for example, through a central structure such as a central beam or base portion).

In some embodiments, the first and second panels may be fixedly attached to one another, meaning that the panels are attached either directly or indirectly (e.g., through a structure such as a central beam) and are not configured to move in relation to one another. In some embodiments, the first and second panels may be moveably attached to one another, meaning that the panels are attached directly or indirectly and are configured to be able to move in relation to one another. As used herein, "moveably attached" means that an item is able to move in any desired or art-accepted manner (e.g., slidingly, translationally, hingedly, and/or rotationally, etc.) in relation to the item to which it is directly or indirectly attached (e.g., where moveably attached, the first and second panels are able to move in any desired or art-accepted manner in relation to one another).

In some embodiments, panels and/or other elements of devices of the invention are hingedly attached, meaning. e.g., that elements are attached such that at least one element is able to turn or pivot with respect to the other, and/or that the elements are positions such that they (or at least one of the elements) can be rotated with respect to each other. For example, in relation to hingedly attached panels, the panels are attached such that at least one of the panels is able to turn or pivot with respect to the other (e.g., through any acceptable attachment means), and/or that the panels are positioned such that they (or at least one of the panels) can be rotated with respect to each other. In some embodiments, hingedly attached refers to a mechanism of attachment wherein the panels of the device are attached, for example, with a bracket hinge, telescope hinge, ball bearing hinge, pivot hinge etc. where a pivotal axis perpendicular to the direction or degree of motion can be identified.

In some embodiments, panels and/or other elements of devices of the invention are slidingly attached, meaning, e.g., that the elements are attached such that at least one element is able to slide back and forth (for example, in a linear and/or parallel direction) in relation to the other element. For example, in relation to slidingly attached panels, the panels are attached such that at least one of the panels is able to slide back and forth in in relation to the other panel.

In some embodiments, panels and/or other elements of devices of the invention are translationally attached, meaning, e.g., that elements are attached such that at least one element is able to move in at least one linear direction in relation to another element. As used herein, "translationally" includes movement in more than one direction, e.g., in two, three, four, five directions, etc. The direction(s) of translational movement may be any desired direction(s).

In some embodiments, structure of the sterilization device or unit provides sufficient support (e.g., by virtue of an L-shaped configuration) for the sterilization device to stably stand upright during operation, for example, such that inner and/or outer faces of the sterilization device are relatively perpendicular to a floor.

In some embodiments, the sterilization device comprises one or more supportive structures. Supportive structures include any desirable structures that enhance the device (e.g., a stabilization-enhancing structure). For example, in some embodiments, the sterilization device comprises a supporting appendage and/or or a base. In some embodiments, the sterilization device comprising a supporting appendage that extends from an outer face of the sterilization device.

In some examples, the sterilization structure of the sterilization device of the invention includes an outer face and an inner face, where the inner face comprises one or more UV-C radiation sources.

In accordance with example embodiments, the UV-C light or radiation sources may be one or more suitable sources that emit ultraviolet (UV) electromagnetic radiation having a wavelength of between about 100 and about 280 nm. The UV-C radiation sources may be configured, e.g., to sterilize any space, surface, and/or structure.

The UV-C radiation sources may be any suitable source. In some implementations, the one or more radiation sources may include one or more germicidal fluorescent lamp. In some examples, the lamp may have a wattage greater than 15 W, e.g., greater than 20 W, e.g., greater than 30 W, e.g., greater than 40 W, e.g., 41 W or greater, and the lamp may operate on any suitable voltage circuit, e.g., an alternating current source of 120V. In some examples, the lamp may output UV-C light (e.g., 253.7 nm wavelength) at greater than 15 W, e.g. greater than 20 watts. e.g., 21 watts or greater. In some examples, the lamp may provide a UV-C light intensity, at 3 meters distance from the bulb, of 15 or greater, e.g., 17 or greater, microwatts per square centimeter. In a particular example, the lamp is (in nominal values) a 42 W lamp with a 425 mA current, 113V voltage, 21 W UV-C output, 17 microwatt per square centimeter at 3 meters, and an average bulb life of 16,000 hours.

In some embodiments, the UV radiation source is one or more ultraviolet lamps, for example, a model 3 watt 10.5 volt T6 Intermediate Screw (E17) Base Germicidal Preheat Incandescent lamp (EIKO), or its equivalent. In some embodiments, the UV-C radiation source is one or more of a traditional UV lamp, such as a mercury-based or non-mercury-based UV lamp. In some embodiments, the UV-C radiation source is one or more UV-C light emitting diode (LED) lamps. In some embodiments the UV-C radiation sources (e.g., bulbs) are shatter resistant, which can enhance the safety of the device. In some embodiments, the one or more UV-C radiation sources comprise at least two different types of UV-C radiation sources. In some embodiments, the sterilization device of the invention is one which excludes UV LEDs (the UV-C radiation source(s) is(/are) not one or more LEDs). The UV-C radiation sources used in the invention may be present in any size, shape, and number desired.

In certain embodiments, the one or more UV-C radiation source of the invention emits continuous radiation. In certain embodiments, the one or more UV-C radiation source of the invention is able to produce different patterns of radiation. The patterns may be, for instance, pulsed, fractional, collimated or scattered to ensure sufficient propagation of the UV-C radiation. In some examples, the patterns may be selected and/or controlled by or via a computer processor of a control system of the sterilization device.

In some embodiments, the inner face of the sterilization structure of the sterilization device includes a first panel and a second panel, and at least one of the first and second panels comprises one or more UV-C radiation sources. In some embodiments, both the first and second panels comprise one or more UV-C radiation sources. Where the face of a panel comprises one or more UV-C radiation sources, that face may be called an "active face".

In some embodiments, the sterilization device of the invention comprises two or more (e.g., three, four, five, six, seven, eight, nine, or ten or more) UV-C radiation sources.

In some embodiments, the sterilization device of the invention comprises one or more of an array of UV-C radiation sources.

In some embodiments, the device of the invention includes a control or management mechanism. As used herein, "management mechanism" refers to a mechanism that, alone or together with some mechanism, contributes to controlling and/or powering the sterilization device. In some embodiments, the management mechanism may include, for example, an activation switch for controlling a part of the device (e.g., for controlling one or more UV-C radiation sources of the sterilization device). In some embodiments, the management mechanism includes a power source. The power source may be suited, for example, for electrically powering one or more UV-C radiation sources. Any acceptable power source may be used. In some embodiments, the power source may include an AC power cord, a DC power cord, e.g., from a transformer or battery pack, a USB or IEEE 1394 receptacle for plugging into a (DC) powered USB or IEEE 1394 device, a battery or set of batteries, or a fuel cell. In some embodiments, the management mechanism may include a timing unit or circuit to control the duration of exposure of a target to one or more UV-C radiation sources. In some embodiments, the management mechanism comprises a control box. In some embodiments, the management mechanism comprises a switch (e.g., a gyroscopically-based switch), also referred to herein as a "safety trigger", that automatically turns-off the device of the invention if the device tips all or partially over. The switch or safety trigger may be implemented as a precautionary item that aims to prevent accidental UV exposure to a user in case the device were to fall over during a sterilization process and or be bumped and redirected during a sterilization process, which could result in accidental exposure to a user. In some embodiments, the management mechanism serves as an advantageous aspect of the integratability of the device within the complex healthcare environment. In various embodiments, the management mechanism is able to recognize, record, and/or report parameters such as date, time, user ID, patient room number, type of sterilization surface or space (e.g., hospital bed), duration of sterilization, optical intensity, and/or sterilization effectiveness. In such embodiments, the management mechanism may beneficially contribute toward providing logistical structure for the sterilization process, and may thereby reduce infection rates in a healthcare institution.

In various embodiments, the devices and methods of the invention utilize one or more field markers, which may serve multiple purposes. In some embodiments, field markers are used to communicate with the management mechanism. For example, in some embodiments, one or more field markers (which may be any desirable structure, e.g., small buoy-like structures) have a UV (e.g., UV-C) detector and a software mechanism to communicate with the management mechanism. In embodiments where the device of the invention comprises one or more field marker(s), the field marker(s) may either be attached to, or may exist as a separate physical entity (or entities) from the device of the invention. In certain embodiments, the field marker includes (e.g., has a coating of) a polymer containing UV sensitive pigments, enabling the field marker to change color(s) during a sterilization cycle, thereby giving the user a qualitative affirmation that the desired sterilization is taking place. In some embodiments, at the onset of a sterilization procedure, the one or more field markers may be placed on or near the object (e.g., surface or structure) or space being sterilized-then the sterilization process may be initiated and the field marker communicates to the management mechanism once sufficient UV-C exposure to the object or space being sterilized has been reached. This communication can function as a quantitative affirmation that the sterilization process has been completed and successful. This parameter can be determined by, e.g., intensity, proximity and exposure time, alone or in any combination. In some embodiments, the invention can also contain a sensor mechanism along the faces of panels or other structures, which may also act as a safety mechanism in case a user or other person were to accidentally attempt to walk through the sterilization field during a sterilization process. This sensor may be, for example, a light, vibration, infrared, and/or ultrasonic sensor.

In some embodiments, the control or management system or mechanism is in electrical communication, whether direct or indirect, with the sterilization device. In some embodiments, the management mechanism is physically dissociated from an outer face of the sterilization structure of the sterilization device. For example, in some implementations, the management mechanism may be free-standing, and in some implementations, the management mechanism may be a self-contained device. In some examples, the management mechanism is physically connected to the device of the invention. In some examples, the management mechanism is located on the device of the invention. For example, in some implementations, the management mechanism is located on the sterilization structure of the sterilization device of the invention, for example, on the outer face of the one or more panels of the sterilization structure. In some examples, some aspects of the management mechanism are located separately from other aspects of the management mechanism. For example, a power switch may be physically located separate and apart from a power source.

FIG. 1 is a perspective view of a sterilization device 1000 according to an example embodiment, and depicts an outer view of a sterilization structure. In various embodiments, the outer face of the sterilization structure is intended to be the point of operation, or the user interface for devices of the invention.

The sterilization device shown in FIG. 1 includes a first panel 1200 and a second panel 1300 that are hingedly attached to one another to form a free-standing sterilization structure. More specifically, first panel 1200 is indirectly hingedly attached to second panel 1300 through base body 1100. Base body 1100 is connected to base 1105. In the illustrated embodiment, base body 1100 is essentially a hollow tubular structure, to which the panels 1200 and 1300 connect via joints 1120*a*, 1120*b*, 1120*c*, and 1120*d*, collectively referred to as joints 1120. The joints 1120 allow the panels 1200 and 1300 to rotate relative to each other between a closed configuration, as illustrated in the left portion of FIG. 2, to open configurations such as shown in the top, right, and bottom portions of FIG. 2.

The first panel 1200 and the second panel 1300 pivot relative to the base body via two separate parallel vertical rotation or pivot axes A and B, as shown in FIG. 1. The first pivot axis A is defined by joints 1120*a* and 1120*b*, and the second pivot axis B is defined by joints 1120*c* and 1120*d*. It should be understood, however, that any number of joints, including a single joint, may be provided for each pivot axis. It should be further understood that other configurations may include only a single pivot axis between the first panel 1200 and the second panel 1300, e.g., in configurations where the first panel 1200 is directly hinged or otherwise mounted to the second panel 1300. Moreover, the one or more pivot axes of the panels 1200 and 1300 may be provided in any suitable orientation relative to each other and/or the surroundings, e.g., the floor on which the device 1000 is supported.

The first panel 1200 has a first face 1210 and a second face 1220. Likewise, the second panel 1300 has a first face 1310 and a second face 1320.

Slideably connected to the first and second panels 1200 and 1300 are third and fourth panels 1400 and 1500, respectively. The third panel 1400 is mounted to slide relative to the first panel 1200 via a first set of parallel guide mechanisms 1600*a* and 1600*b*, while the fourth panel 1500 is mounted to slide relative to the second panel 1300 via a second set of parallel guide mechanisms 1600*c* and 1600*d*. As these mechanisms 1600*a*, 1600*b*, 1600*c*, and 1600*d* operate in the same manner in the illustrated example, they are described generically as guide mechanism 1600, it being understood that these elements have the same features, except that guide mechanisms 1600*a* and 1600*b* are mirror images with respect to guide mechanisms 1600*c* and 1600*d*.

In addition to each of the third and fourth panels 1400 and 1500 being slideable between respective proximal positions (see, e.g., FIG. 1, and left-side portion of FIG. 2) and distal positions (see, e.g., FIGS. 6 and 7 and top portion of FIG. 2), the fourth and fifth panels 1400 and 1500 are rotatable, after moving into their distal positions, relative to the respective first and second panels 1200 and 1300. The fourth and fifth panels 1400 and 1500 are shown in rotated orientations in the bottom and right-side portions of FIG. 2 and in FIG. 10.

Figure 3:
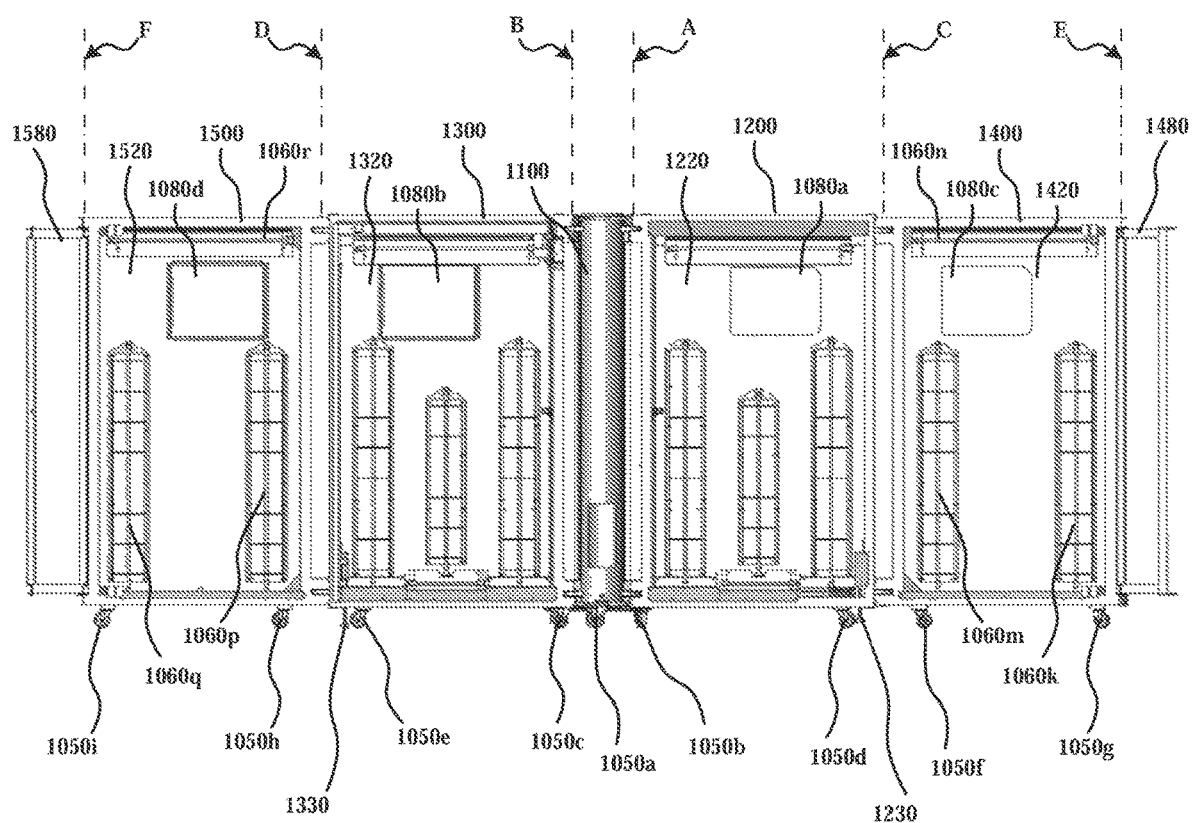
FIG. 3 is a view of an active side of the sterilization unit of FIG. 1 in an expanded linear configuration.

Referring to FIG. 3, the third and fourth panels 1400 and 1500 are rotatable relative to the first and second panels 1200 and 1300 about rotation or pivot axes C and D, which in the illustrated example are vertical and parallel to the pivot axes A and B of the respective first and second panels 1200 and 1300. It should be appreciated, however, that in some examples the pivot axes may be non-vertical and/or non-parallel to each other. The angle of rotation of adjacent elements (e.g., panels) about the axes A, B, C, and D may be within any suitable range and include any number of angles, e.g., 45 degrees, 90 degrees, 135 degrees, 180 degrees, 225 degrees, 270 degrees, or 360 degrees.

At the distal ends of the third and fourth panels 1400 and 1500 are first and second linking sections or panels 1480 and 1580 respectively. The linking sections 1480 and 1580 are rotatable relative to the third and fourth panels 1400 and 1500 about rotation or pivot axes E and F, illustrated in FIG. 3. Although these axes E and F are parallel with axes A, B, C, and D, any suitable rotation axes may be provided. Linking panels 1480 and 1580 may be folded or rotated about respective axes E and F in any suitable angle and/or direction and may include, in some implementations, a matte black or other suitable surface configured to reduce light reflection and/or light leakage around the edges of the unit 1000.

The linking sections 1480 and 1580 are complementary in that they are configured to be releasably attached to each other at their respective distal ends via a latching and/or locking mechanism. This allows the sterilization unit 1000 to be folded and secured into the orientation shown in the bottom portion of FIG. 2 and in FIG. 11, as well as securing the unit 1000 in its closed orientation, as shown, for example, in the left-side portion of FIG. 2.

The complementary nature of the linking sections 1480 and 1580 also allow multiple instances of the sterilization unit 1000 to be linked to each other end-to end. In some such examples, the control system of one of the linked sterilization units may control all of the other linked units 1000 in a master-slave arrangement.

Figure 4:
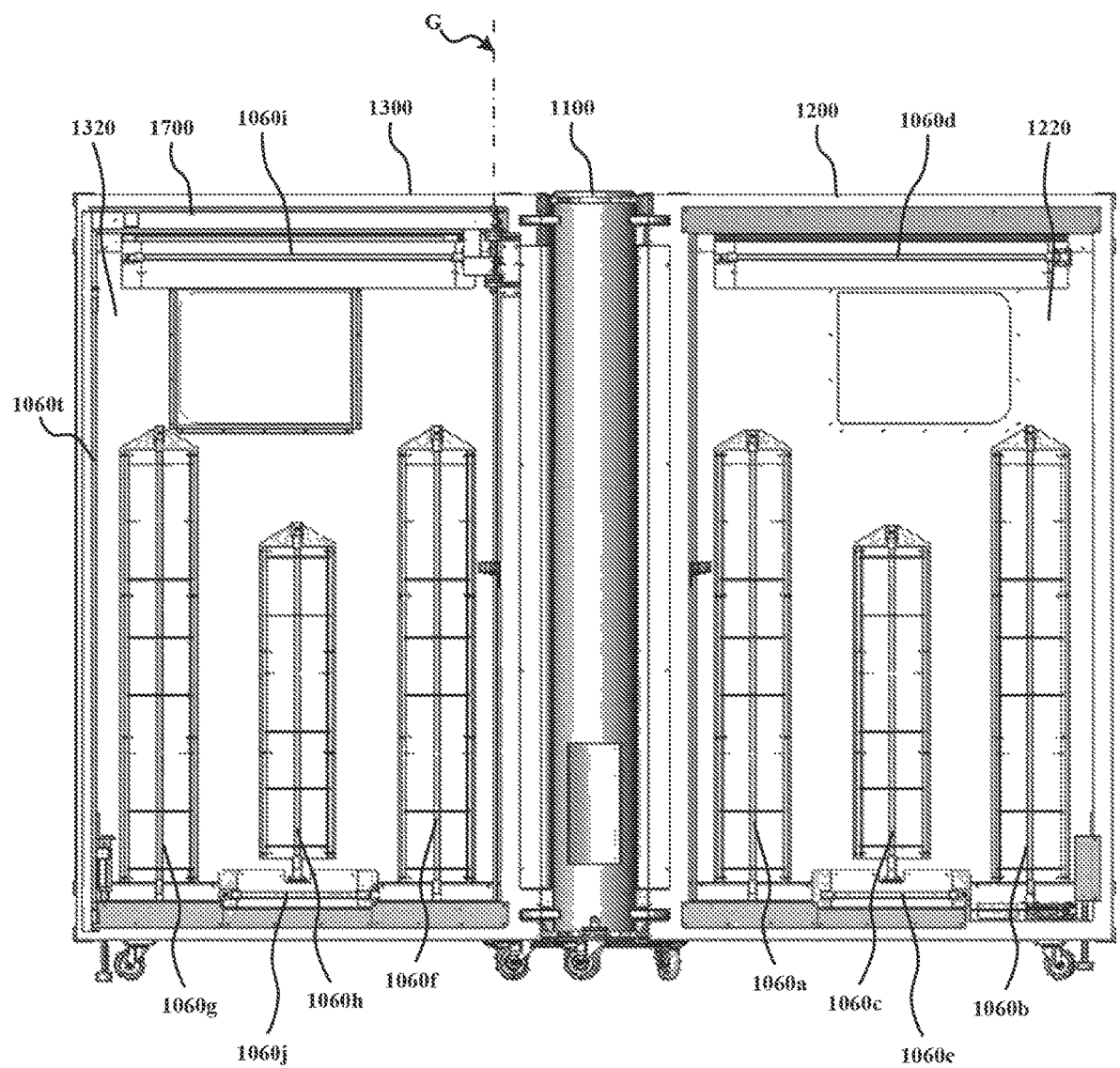
FIG. 4 is a view of an active side of the sterilization unit of FIG. 1 in a linear configuration without expanded distal panels.

Referring to FIGS. 3 and 4, the UV-C light is emitted from UV-C light sources 1060*a*, 1060*b*, 1060*c*, 1060*d*, 1060*e*, 1060*f*, 1060*g*, 1060*h*, 1060*i*, 1060*j*, 1060*k*, 1060*m*, 1060*n*, 1060*p*, 1060*q*, 1060*r*, and 1060*t* which may be generically and/or collectively referred to herein as UV-C light source or sources 1060 and include the features of the UV-C light sources described herein unless indicated otherwise. Each of the UV-C light sources includes a fluorescent UV-C emitting bulb and a curved reflective panel mounted behind the bulb. The reflective panel provides greater light intensity by reflecting light initially emitted away from the sterilization target back toward the target. The curvature may be round, parabolic, or any other suitable geometry. Some examples may not include reflectors, e.g., where direction light-emitting elements are provided.

Figure 5:
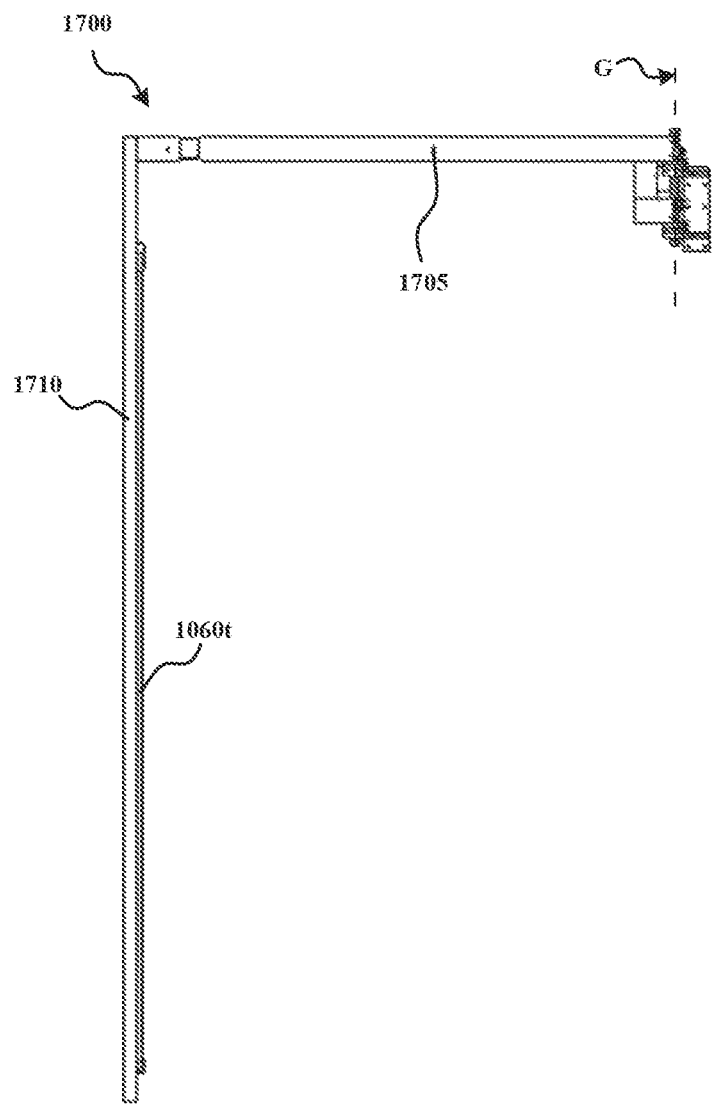
FIG. 5 is a side view of a pivot mechanism in the form of an extension arm.

Referring to, for example, FIGS. 4 and 5, the UV-C light source 1060*t* is mounted on a cantilevered pivot mechanism 1700, which pivots about a rotation or pivot axis G at a location that is relatively close to the base body 1100, although the location of the pivot axis G may be at any other suitable location in some examples. Although the pivot mechanism 1700 is mounted to the second panel 1300 it should be understood that the pivot mechanism 1700 may be mounted to any panel or base body or any other suitable component of the sterilization unit 1000. The pivot axis G is parallel to the other axes A, B, C, D, E, and F, but may be selected to be non-parallel and/or non-vertical in some examples. Further, although the pivot mechanism 1700 includes a single UV-C light source 1060*t* mounted on a downward extension 1710 in the illustrated example, it should be understood that any number of UV-C light sources may be provided and at any suitable location. For example, one or more additional UV-C sources may be provided on the pivot arm 1705 of the pivot mechanism 1700. This would allow, in some examples, UV-C light to be projected downwardly to a sterilization target or targets at a location below the pivot arm 1705.

Figure 10:
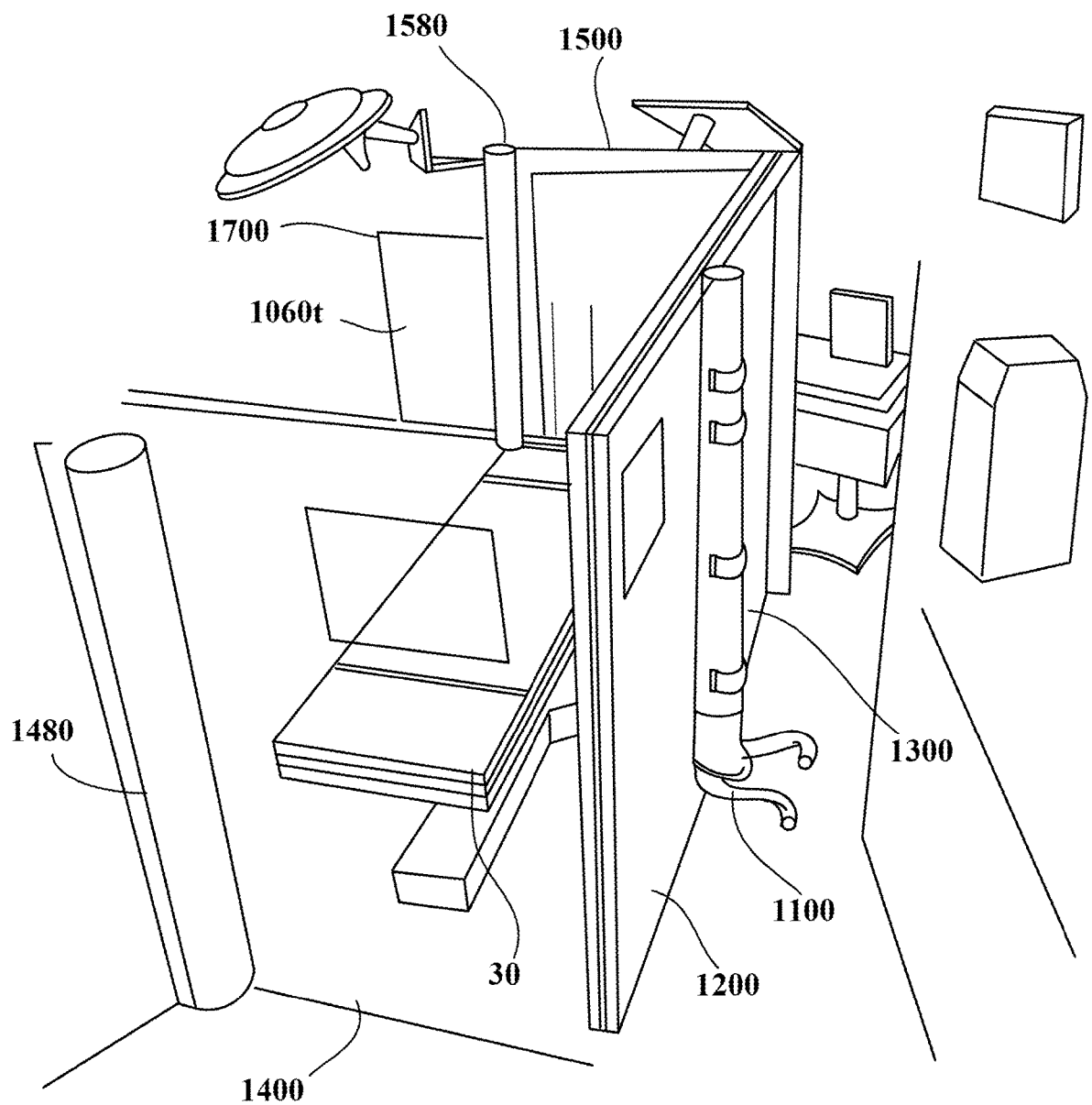
FIG. 10 is a perspective view of the sterilization unit of FIG. 1 in a C-shaped configuration when the extension arm in an extended position.

The pivot mechanism 1700 is actuatable to move the light source 1060*t* from a retracted position, as shown in FIG. 4, to an extended position, as shown in FIG. 10. The pivot mechanism may be actuated, for example, by manual actuation and/or automatic actuation, e.g., an electro-mechanical actuator which, in some examples, may be powered and/or controlled by the control system of the overall unit and/or a dedicated control system. The pivot mechanism 1700 may also be comprised of one or more UV-C emitting devices Although the UV-C-emitting components of the UV-C light sources 1060 are linear fluorescent bulbs, it should be appreciated that any suitable UV-C light source may be provided, e.g., non-linear and/or non-fluorescent elements.

The various panels 1200, 1300, 1400, and 1500, as well as the base body 1100 and the linking sections 1480 and 1580 are configured to block UV-C light radiation from passing therethrough.

Since the panels 1200, 1300, 1400, and 1500 include UV-C light sources mounted on their respective second faces 1220, 1320, 1420, and 1520, and the panels 1200, 1300, 1400, and 1500 are highly configurable, the sterilization unit 1000 is extremely adaptable to many different sterilization applications. Adding to this flexibility is the ability of the unit 1000 to selectively control the UV-C light sources based on particular applications.

Further, since the various panels 1200, 1300, 1400, and 1500, as well as the base body 1100 and the linking sections 1480 and 1580 are configured to block UV-C light radiation from passing therethrough, the sterilization unit 1000 is selectably configurable in a manner that irradiates—from multiple angles—desired sterilization targets while shielding the surroundings, including people and/or animals, from the UV-C light.

In some examples, such as illustrated in FIG. 3, one or more windows 1080 are provided. In the illustrated example, the each of the panels 1200, 1300, 1400, and 1500 includes a respective window 1080*a*, 1080*b*, 1080*c*, and 1080*d*, which may be generically and/or collectively referred to herein as window or windows 1080.

The windows 1080 allow visible light to pass from the irradiated sterilization area, but block UV-C light. This allows a human operator to view the sterilization zone without being exposed to the UV-C light. The window may be, for example, glass and/or one or more polymeric materials. The window may or may not include a protective barrier against UV-A and UV-B light which may be generated as byproducts from some UV-C light sources. Such protection may be provided, for example, as a protective film and/or tint, which in some examples may also serve to dampen the brightness of the light sources 1060 for bystanders.

The panels 1200, 1300, 1400, and 1500 are reconfigurable between a large number of selectable panel orientations depending upon, for example, desired mobilization of the unit 1000, the particular sterilization application, and/or space constraints in a particular environment. In some orientations, the panels 1200, 1300, 1400, and 1500 are controlled to sterilize spaces, surfaces, and/or objects onto which the unit 1000 is configured to direct UV-C light, as described in greater detail herein.

Referring to FIG. 3, the device 1000 includes casters 1050*a*, 1050*b*. 1050*c*, 1050*d*. 1050*e*, 1050*f*, 1050*g*. 1050*h*, and 1050*i*, which may be referred to collectively or generically herein as caster or casters 1050. The casters 1050*a*, 1050*b*, and 1050*c* are mounted at the base 1105 of the base body 1100, the casters 1050*d* and 1050*e* are mounted at the respective distal portions of the first and second panels 1200 and 1300, the casters 1050*f* and 1050*h* are mounted at respective proximal locations on the third and fourth panels 1400 and 1500, and the casters 1050*g* and 1050*i* are mounted at respective distal locations on the third and fourth panels 1400 and 1500. The casters 1050 thus fully support the sterilization unit 1000 while allowing the unit 1000 to be rolled to different locations and repositioned into the multiple configurations such as, for example, the various example configurations described herein.

Figure 2:
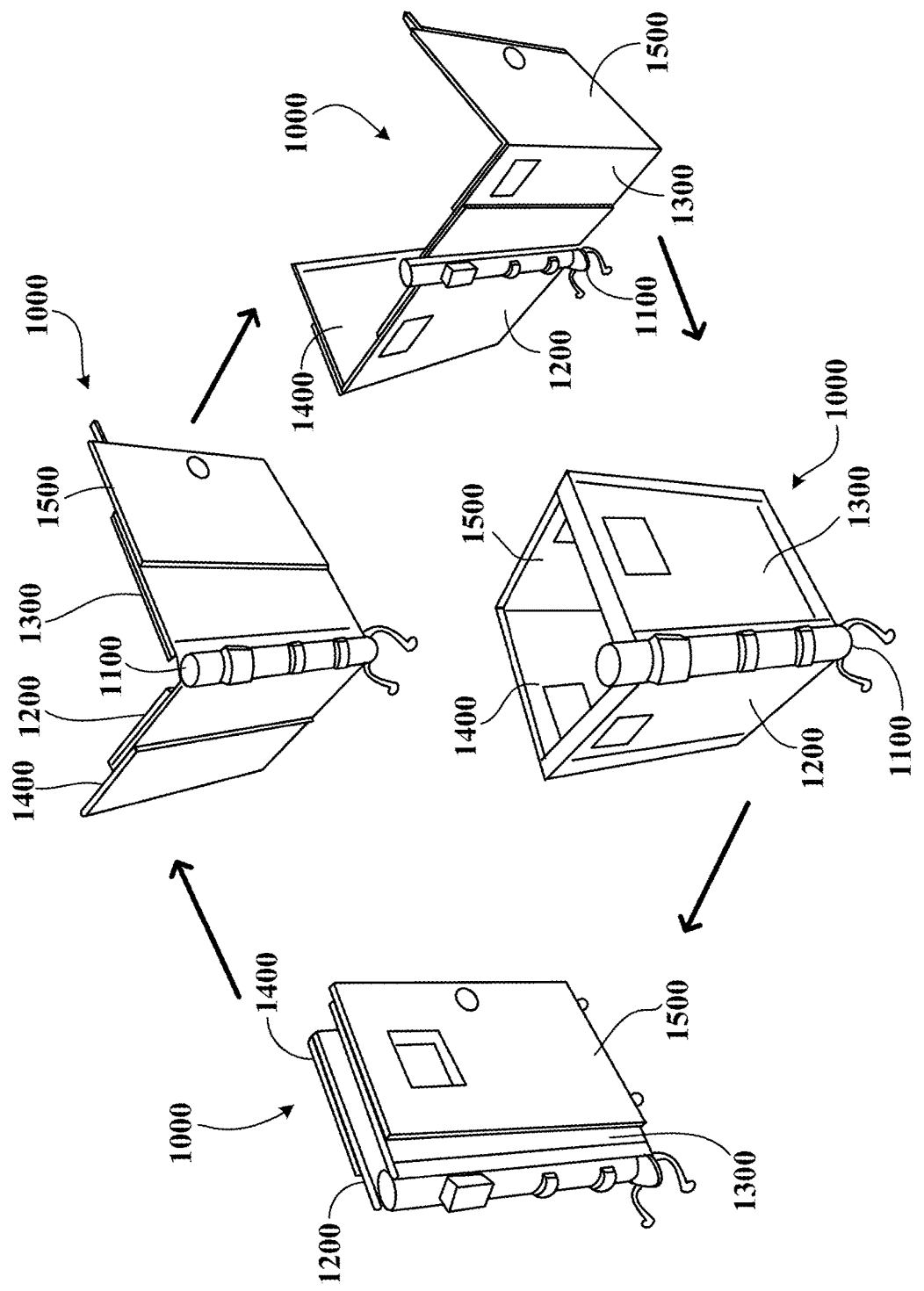
FIG. 2 shows some example configurations of the sterilization unit of FIG. 1.

Although the unit 1000 may be moved or transported while in any desired panel orientation, it may be particularly beneficial to configure the unit 1000 into a closed panel orientation, as illustrated in the left-side portion of FIG. 2, since the compact dimensions may allow the unit 1000 to be more easily maneuvered, including moving the unit through standard door openings (e.g., door openings that are 32 inches wide by 82.5 inches tall).

Once the unit 1000 is in a desired position in a room, the first and second panels 1200 and 1300 may be opened relative to each other at any suitable angle (e.g., assuming the closed, parallel position to be zero degrees, the selected angle may be any angle between zero and 360 degrees, e.g., 45 degrees, 90 degrees, 135 degrees, 180 degrees, 225 degrees, 270 degrees, or 360 degrees) and the third and fourth panels 1400 and 1500 may each by fully or partially slid into their distal positions and remain parallel to the slide path or rotated about their respective pivot axes C and D.

To secure the sterilization unit 1000 against unintentional rolling, the first panel 1200 and the second panel 1300 include securement feet 1230 and 1330 as illustrated, for example, in FIG. 3. The securement feet 1230 and 1330 are each actuatable between a retracted position, in which the feet 1230 and 1330 do not contact the surface supporting the unit 1000, and an extended position in which the feet 1230 and 1330 contact the surface supporting the unit 1000 in order to resist rolling via casters 1050. In the state illustrated in FIG. 3, the securement foot 1230 is in the retracted position and securement foot 1330 is in the extended position. Although the illustrated example includes securement feet, it should be appreciated that any form of temporary locking mechanism may be provided, and some examples may not include any mechanism to resist against rolling.

Figure 6:
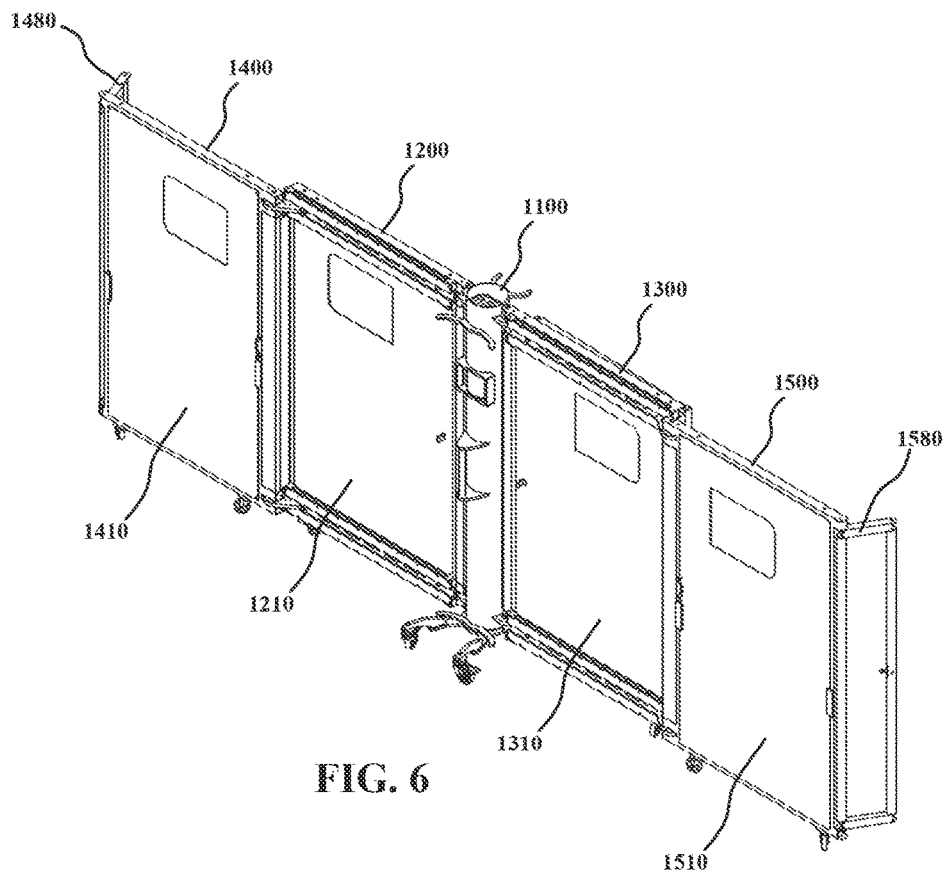
FIG. 6 is a perspective view of the sterilization unit of FIG. 1 in an expanded linear configuration.
Figure 7:
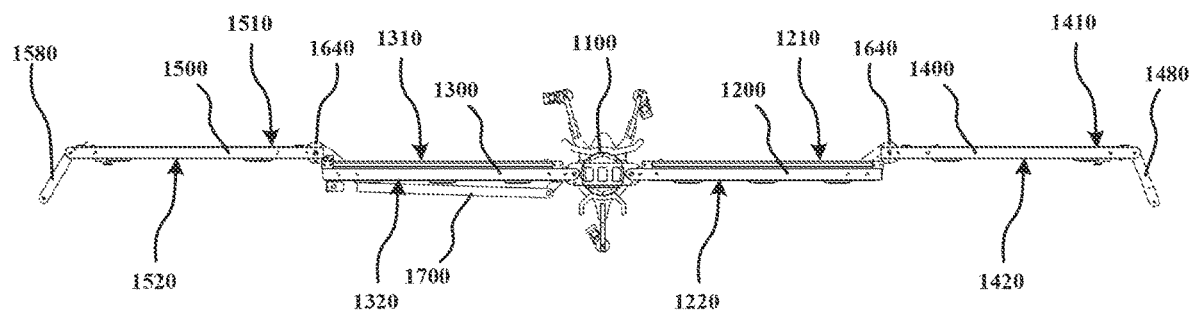
FIG. 7 is a top view of the sterilization unit of FIG. 1 in an expanded linear configuration.

FIGS. 6 and 7 show a configuration that may be advantageous for sterilizing an elongated surface, such as, for example, a wall of a hospital room or hallway. In this configuration, the first and second panels 1200 and 1300 have been rotated to an angle of 180 degrees and substantially coplanar, and the third and fourth panels 1400 and 1500 have been extended into their distal positions, without further rotation, such that each of the first panel 1200, the second panel 1300, the third panel 1400, and the fourth panel 1500 are parallel and have their UV-C sources 1060 directed to emit UV-C light in the same direction. For this example unit 1000, this configuration maximizes the effective length of the unit 1000, which may provide for more efficient sterilization of longer surfaces such as long walls in a room or a hallway.

Figure 12:
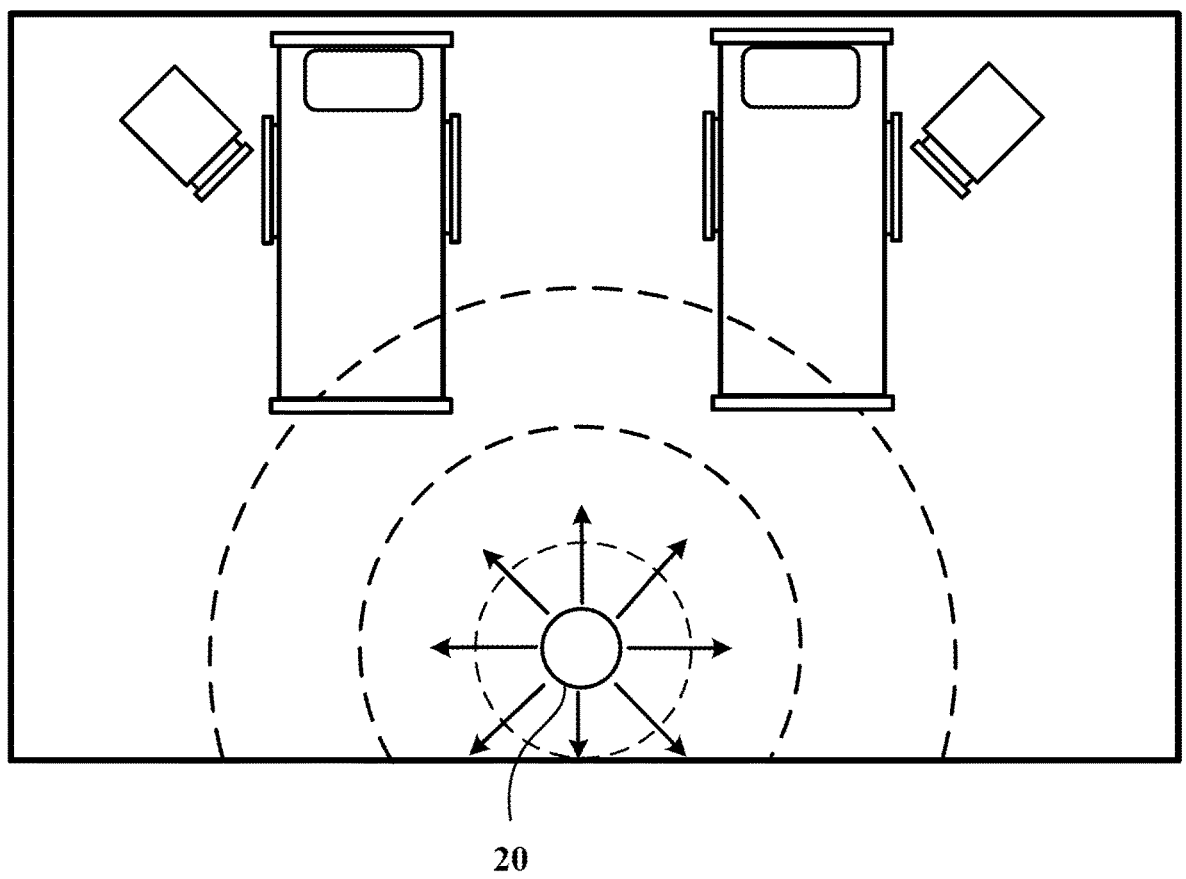
FIG. 12 is a sterilization system in accordance with related art.

Further, due to the presence of multiple UV-C sources 1060, the target surface, e.g., a wall, is hit at each location with light from multiple angles, which increases the effective light strength and facilitates light coverage, especially where there are irregularities in the target surface. In contrast, alternative systems such as shown in FIG. 12 only allow each location of a sterilization target to be hit with a UV-C radiation from a single direction, corresponding to the single source, and the UV-C light intensity decreases dramatically as the light progresses further away from the source 20. Another problem is the results in systems such as shown in FIG. 12 are never repeatable to achieve epidemiological results because of the target surfaces; in example implementations in accordance with the present invention, there are known quantities of space, which allows for reproducible results (e.g., light intensity at various locations) within the known quantities of space (e.g., surface area and/or volume). Alternative systems such as illustrated in FIG. 12 are, in contrast, subject to the size variation and/or irregularities of a room.

In the example of FIGS. 6 and 7, the linking sections 1480 and 1580 are rotated to provide shielding against UV-C light passing from the sterilization target area. In other examples, the linking panels 1480 and 1580 may be coupled to corresponding linking sections 1580 and 1480, respectively, of one or more other sterilization units 1000. This modular structure allows for an even longer effective length for simultaneous sterilization.

Figure 8:
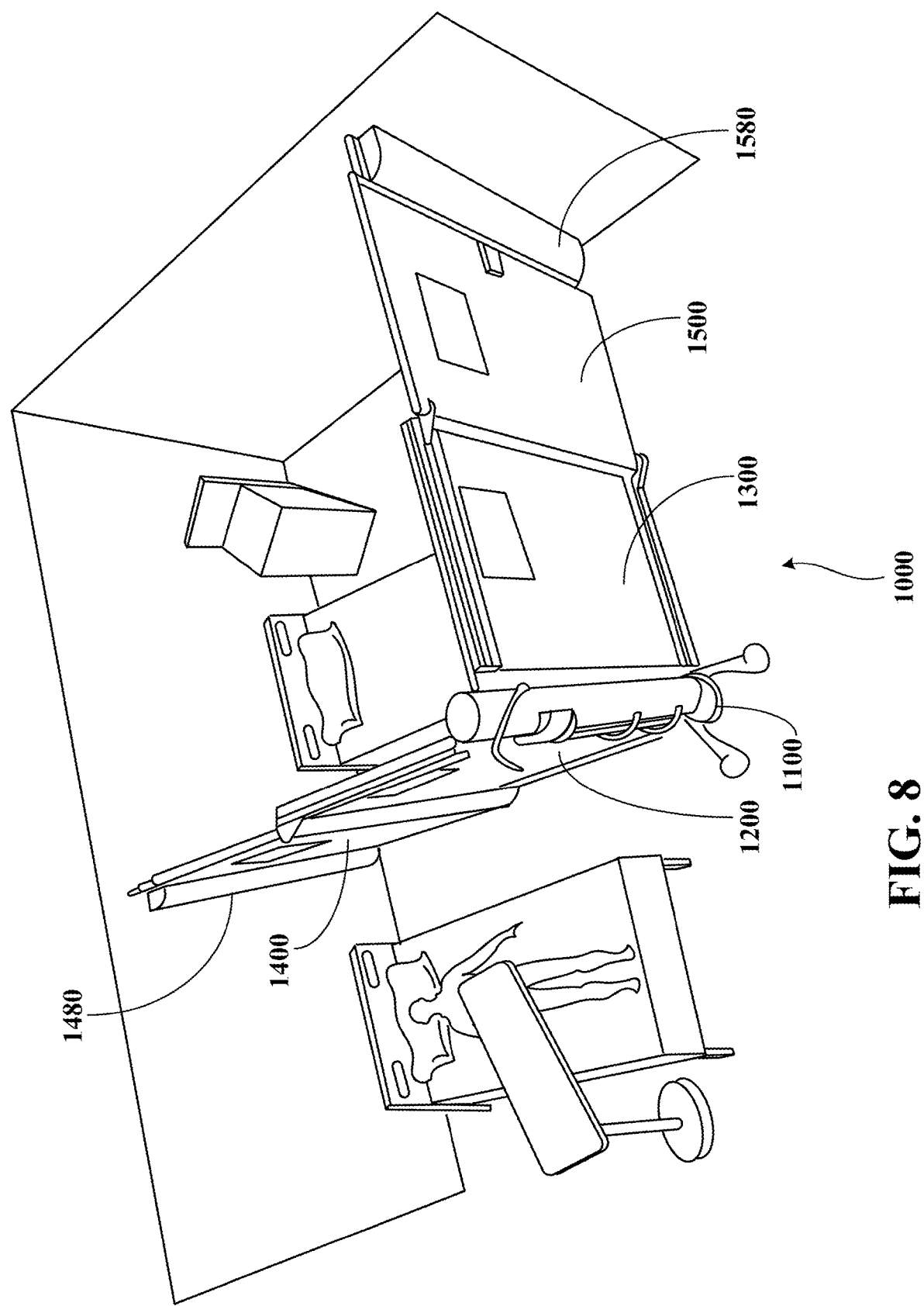
FIG. 8 is a perspective view of the sterilization unit of FIG. 1, in an orthogonal expanded configuration in a corner of a two-bed room of a healthcare facility.
Figure 9:
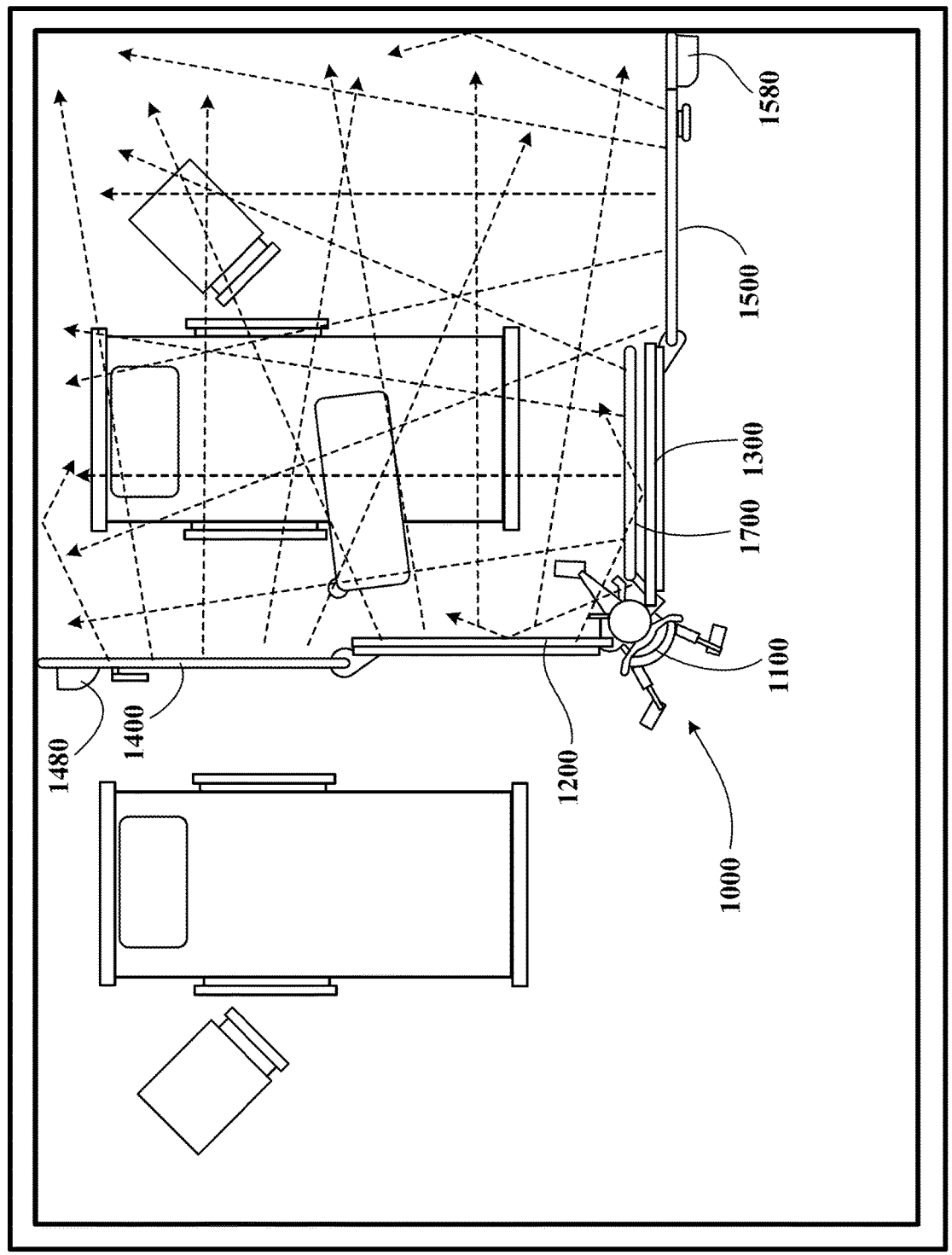
FIG. 9 a top view of the configuration of FIG. 8.

FIGS. 8 and 9 show an example configuration for sterilizing a portion of a two-bed hospital room. In these configurations, the sterilization unit 1100 has been rolled into the room, e.g., through a standard doorway entrance, and expanded into the illustrated configuration. This configuration is similar to that of FIGS. 6 and 7 in that the third and fourth panels 1400 and 1500 are in their fully extended distal positions, without further rotation, but differs in that the first and second panels 1200 and 1300 have been rotated to an angle less than 180 degrees, in particular a substantially right angle. Referring, for example, to FIGS. 8 and 9, it should be noted that the base body 1100 may be oriented at differing angles relative to the panels 1200 and 1300. In this manner, the base body 1100 may function as an additional linkage in the structure of the sterilization unit 1000, which provides for additional flexibility and allows for controls located on the base body 1100 to be oriented in a desired direction.

As illustrated, the configuration of FIGS. 8 and 9, as well as many other possible configurations, allows for only a selected target portion of a larger area (the room in this example) to be sterilized, while simultaneously blocking the UV-C light from other portions of the area. This has many potential advantages, including, for example, the ability to sterilize one bedding area of a room while simultaneously the second bed is inhabited by a patient and healthcare personnel are permitted to be present in the room without substantial exposure to the UV-C light. This also provides advantages for convenient healthcare work flow and permitting use of the space surrounding the sterilization unit in considerations for the urgency and expedited needs of a healthcare facility.

The room partition setups such as illustrated in FIGS. 8 and 9 may be extremely effective especially for contact precaution sterilization. In this position, the outer panels are fully extended and are placed against the wall as illustrated. The first and second, or inner, panels 1200 and 1300 form a 90° angle to each other creating an enclosure combined with the wall portions adjacent the corner of the room. The configuration may be locked via a locking mechanism such as described in greater detail herein.

Further, due to the orthogonal orientation of the first and third panels 1200 and 1400 relative to the second and fourth panels 1300 and 1500, the UV-C light sources 1060 provide enhanced UV-C irradiation across the entire target area. Light output from the four panels 1200, 1300, 1400, and 1500 are schematically illustrated in FIG. 9 by arrows shown in the sterilization target zone. The arrows use different styles of broken lines to help distinguish the output from the four different panels for illustration purposes and do not denote any differences in intensity of UV-C light coming from the various panels 1200, 1300, 1400, and 1500. As illustrated, the light paths overlap in the target zone, which increases effective intensity, coverage, and the number of angles from which the surfaces or objects are hit with the UV-C light. This focusing of UV-C energy from multiple directions results in convergent amplification on the target surface and pathogens. Since, for particular configurations, distances between the light sources and various locations within the sterilization target area are known and output intensities of the UV-C sources 1060 are known, the system 1000 may, in some implementations, selectively control the number and/or intensities of the UV-C sources based on the configuration in order to achieve adequate UV-C light intensity at locations to be sterilized.

As indicated above, alternative systems such as shown in FIG. 12 only allow each location of a sterilization target to be hit with a UV-C radiation from a single direction, corresponding to the single source, and the UV-C light intensity decreases dramatically as the light progresses further away from the source 20. In addition to not effectively sterilizing the target area, at least without repositioning the source 20 multiple times within the same room for a single object or area, the system of FIG. 12 also does not include any mechanism to prevent areas outside of a target area from receiving UV-C radiation.

FIG. 10 shows a further configuration of the of the sterilization unit 1000. This configuration is similar to the configuration of FIGS. 6 and 7 but differs in that the third and fourth panels 1400 and 1500 have been further rotated, about respective axes C and D, to be at substantially right angles to the first and second panels 1200 and 1300, and the pivot mechanism 1700 has been pivoted into a fully extended position orthogonal to the first and second panels 1200 and 1300. This configuration may be especially useful for elongated, e.g., rectangular, sterilization targets, such as, for example, a patient bed or operating table 30 such as that illustrated in FIG. 10. The light source 1060t allows for the sterilization unit 1000 to irradiate the target 30 with true 360 degree UV-C light exposure, e.g., on a surface, object, or space. It should be noted that in some examples the pivot mechanism 1700 includes multiple UV-C light sources and/or the unit includes multiple pivot mechanisms 1700.

The arrangement of FIG. 10 allows in some examples, a plurality of targets 30 to be sterilized sequentially. This may be facilitated, for example, by swinging open the third or fourth panel 1400 or 1500 to provide access for inserting and removing the respective targets 30 before and after the respective sterilizations.

Figure 11:
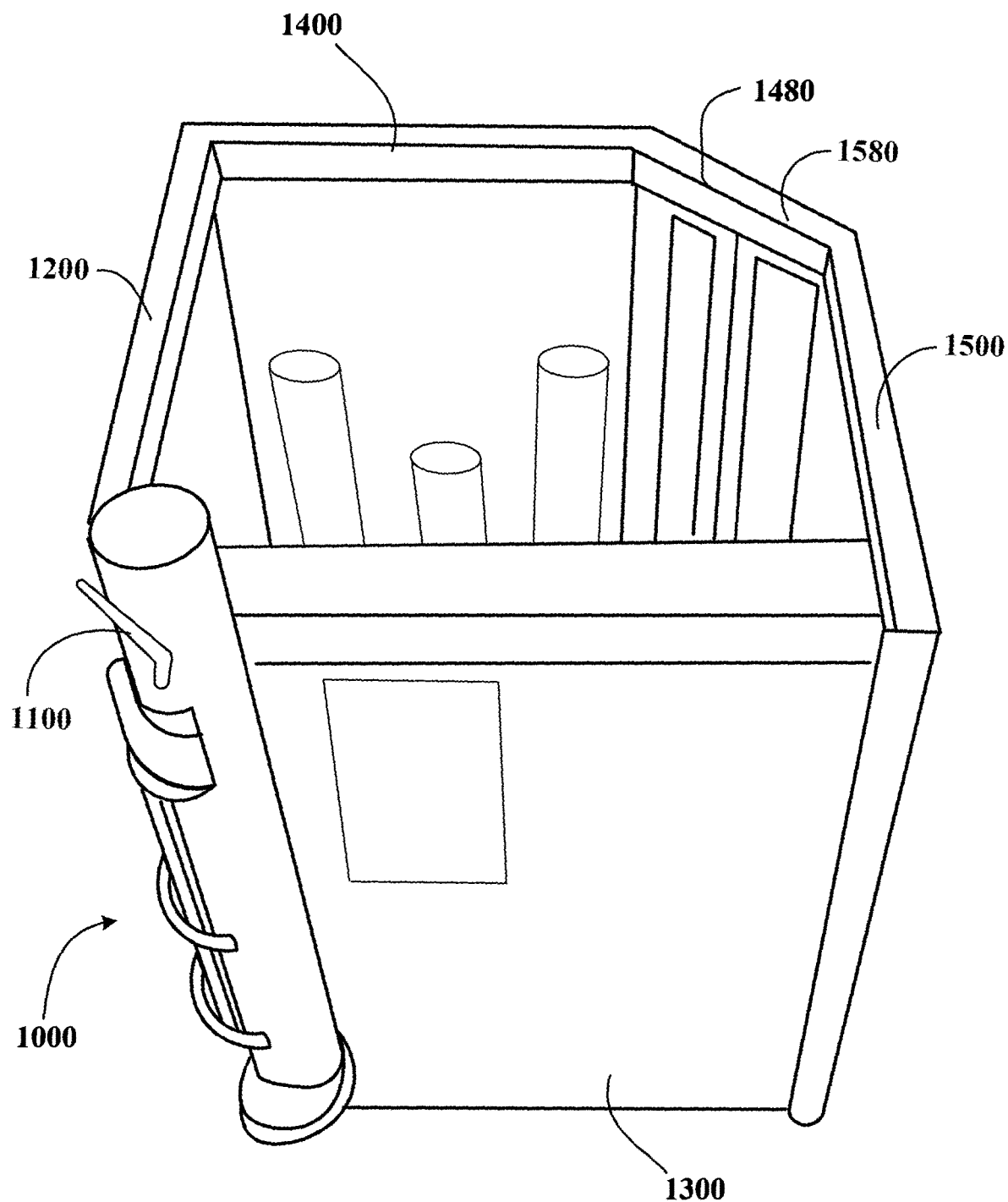
FIG. 11 is a perspective view of the sterilization unit of FIG. 1 in a cube-shaped enclosed orientation.

FIG. 11 shows a further configuration whereby the sterilization unit forms a continuous enclosure around the sterilization target or targets. In this configuration, the first and second panels 1200 and 1300 are rotated to be orthogonal to each other and the third and fourth panels 1400 and 1500 have been fully distally extended and further rotated to be orthogonal to the first and second panels 1200 and 1300, respectively. To complete and secure the enclosure, the first linking section 1480 is latched with the second linking section 1580. This arrangement provides for the UV-C light to impinge on the sterilization target or targets from all four sides while blocking the UV-C light from the surrounding areas.

The sterilization unit 1000 may be advantageously utilized for discharge sterilization of patient rooms, which is a sterilization procedure that occurs when a patient is being released from a healthcare facility. In some examples, the healthcare worker would implement the sterilization unit 1000 after mechanical cleaning of patient room. Example Items that need sterilization that could be performed by the sterilization unit 1000:

Patient bed (All sheets and linens off bed)
Night stand
Sink/Sink Area
Bathroom
Chair
   Over-the-bed-table/Meal tray
Wall/Patient Zone The patient bed may need to be sterilized independently from all other items to ensure effective 360° sterilization. Depending on the layout of room, some other items, e.g., chair, nightstand, and food tray may be combined and effectively sterilized at the same time. In some other example implementations, all items may be sterilized simultaneously.

Figure 14:
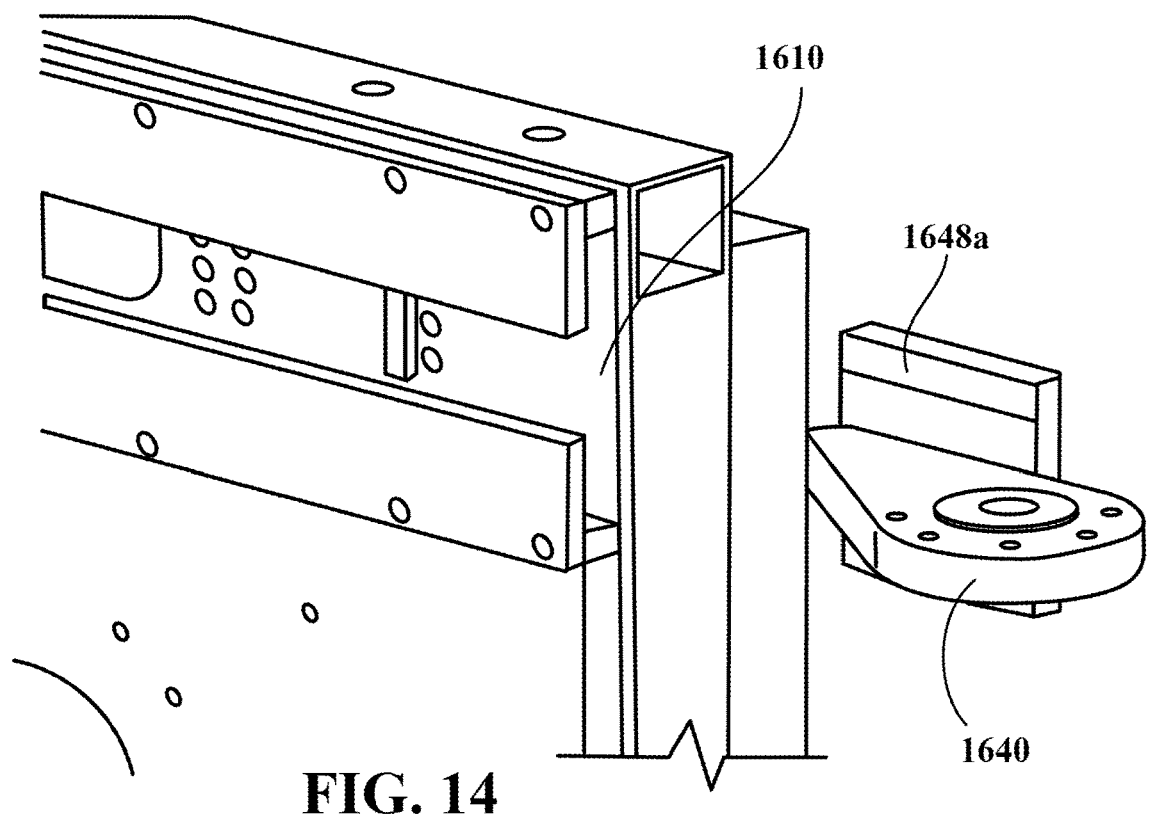
FIG. 14 shows the guide mechanism of FIG. 13 with a guide carriage removed from a guide channel.
Figure 15:
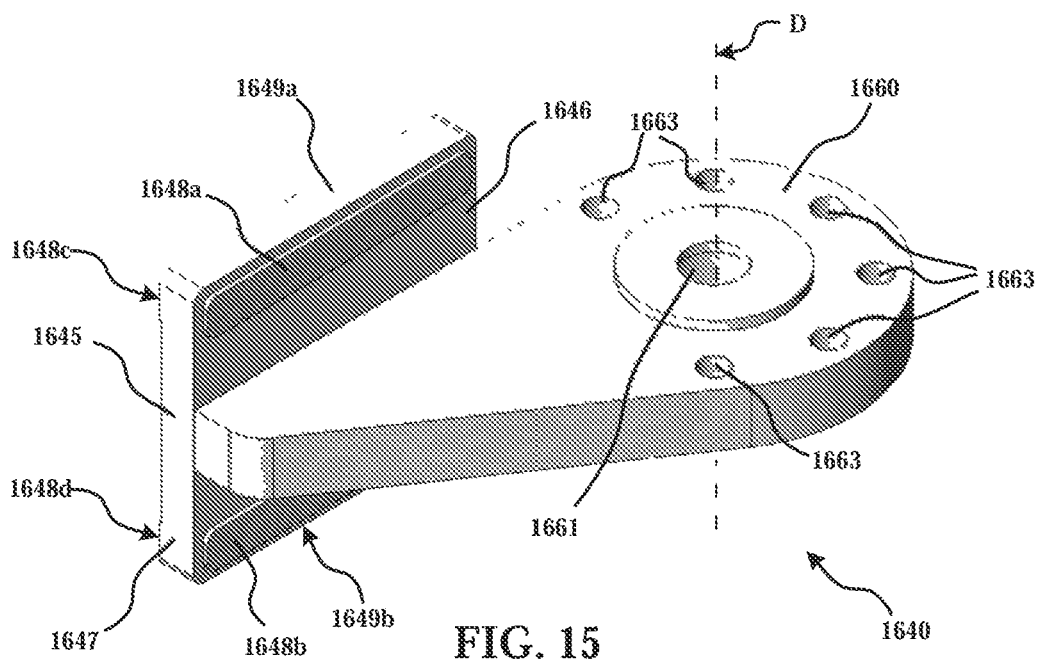
FIG. 15 is a perspective view of the guide carriage of FIG. 13.
Figure 16:
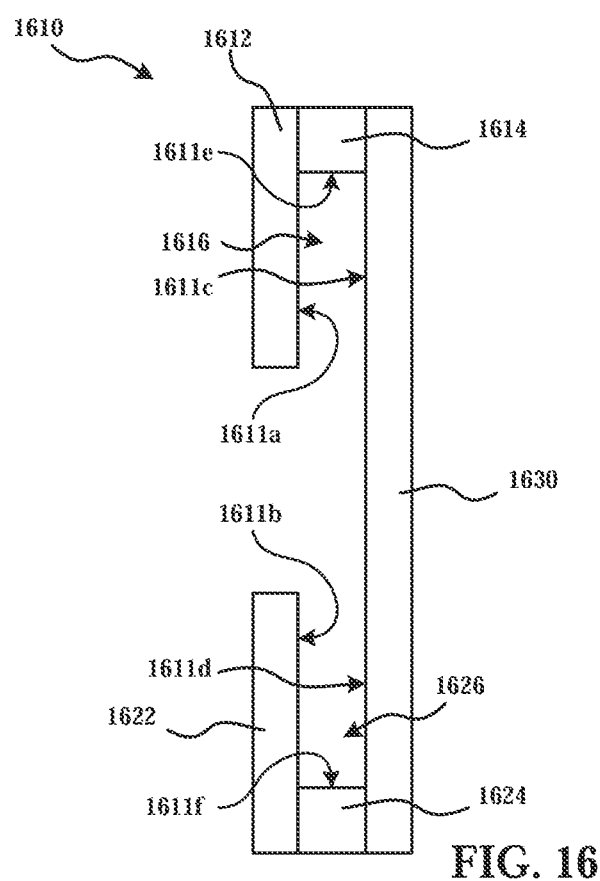
FIG. 16 is an end view of the guide channel of FIG. 13.

FIGS. 13 to 21 show in greater detail the guide mechanism 1600 by which the third and fourth panels 1400 and 1500 slide and rotate relative to the respective first and second panels 1200 and 1300. The example illustrated is, in particular one of the mechanisms 1600c or 1600d linking the second and fourth panels 1300 and 1500, it being understood that the guide mechanisms 1600a and 1600b are mirror images of what is illustrated in FIGS. 13 to 21. The guide mechanisms 1600 each include a linear C-shaped guide channel 1610 and a guide carriage 1640 configured to be received in the guide channel 1610. Referring to FIG. 16, the guide channel 1610 is C-shaped and includes a back plate 1630, which mounts directly to the first or second panel 1200 or 1300. The guide channel 1610 also includes an upper flange 1612 and a lower flange 1622 spaced apart and supported from the back plate 1630 via an upper block 1614 and a lower block 1624, respectively, to form a respective upper and lower spaces or recesses 1616 and 1626.

Referring to FIG. 15, the guide carriage includes a guide plate 1645 and a mounting plate 1660. The guide plate 1645 includes an upper extension 1646 and a lower extension 1647. When the guide carriage and channel of respective FIGS. 15 and 16 are assembled, as illustrated, for example, in FIG. 13, the upper extension 1646 of the guide carriage 1640 is received and laterally constrained in the upper recess 1616 of the guide channel 1610, and the lower extension 1647 of the guide carriage 1640 is received and laterally constrained in the lower recess 1626 of the guide channel 1610. This mating allows the guide carriage 1640 to slide along axis G, shown in FIG. 13. Although the axis G is horizontal and linear in the illustrated example, it should be understood that any suitable sliding path may be provided, including, for example, curved, nonlinear, and/or non-horizontal paths.

To apply lateral support forces during the sliding of the guide carriage 1640 relative to the guide channel 1610, the guide carriage 1640 includes bearing surfaces 1648a, 1648b, 1648c, and 1648d, which may be collectively referred to herein as bearing surfaces 1648. Bearing surfaces 1648a, 1648b, 1648c, and 1648d are configured to contact and be slideable along respective bearing surfaces 1611a, 1611b, 1611c, and 1611d of the guide channel 1610, which is illustrated in FIG. 16, in order to laterally constrain the guide carriage 1640 as it slides along the path defined by the guide channel 1610. These interfaces constitute a plain bearing, although it should be appreciated that any other suitable guide mechanism may be provided, e.g., one or more linear bearings or other guides.

The bearing surfaces 1648 may be formed of a low-friction material, such as, for example, PTFE, although any suitable material may be provided.

As indicated above, the guide carriages 1640 and guide channels 1610 provide lateral constraint between the guide carriages 1640 and the guide channels 1610, which are mounted to the first and second panels 1200 and 1300. Referring to FIG. 1, these guide interfaces are provided at two locations—one upper and one lower—on each panel 1200, 1300, 1400, 1500. The guide channels 1610 extend along the length of the first and second panels 1200 and 1300, while the guide carriages 1640 mount along a proximal end of each of the third and fourth panels 1400 and 1500.

Figure 13:
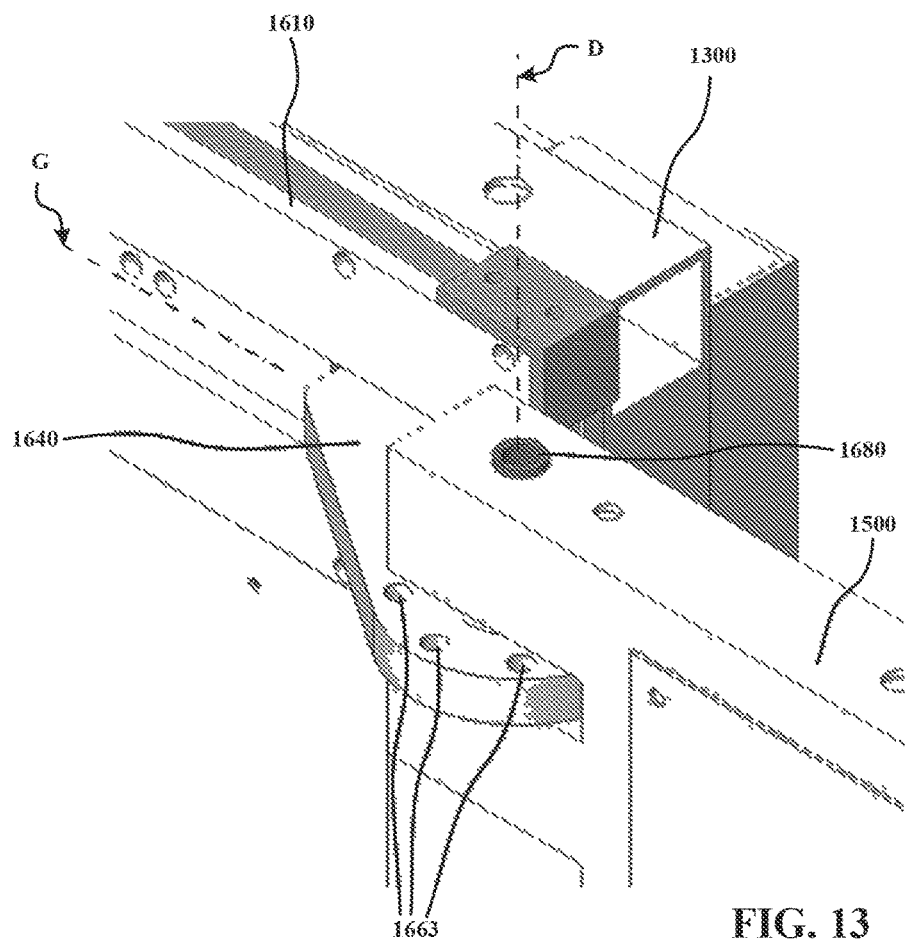
FIG. 13 shows a guide mechanism joining two panels of the sterilization unit of FIG. 1.

Referring to FIGS. 13 to 15, the third and fourth panels 1400 and 1500 are each mounted to the mounting plates 1660 of the guide carriages 1640 via a pivot or rotation shaft 1680 which passes through an opening 1661 in the mounting plate 1660, forming the respective rotation axis C or D depending on the panel, axis D being shown in the illustrated example of FIG. 15. Referring to FIG. 13, the third and fourth panel 1400 and 1500 have a clevis structure that extends above and below the mounting plate 1660 to receive the pivot shaft 1680 above and below the mounting plate 1660.

After rotating the third or fourth panel 1400 or 1500 the angle of rotation may, in some examples, be temporarily set or locked in position. In the illustrated example of FIGS. 13 to 21, the angle is temporarily locked by selectively pushing a locking pin through a recess or hole in the panel 1400 or 1500 and one of a plurality of recesses or holes 1663 at various angles about the opening 1661. It should be understood, however, that any suitable mechanism may be provided.

Likewise, the angle of each of the first and second panels 1200 and 1300 is locked by an analogous locking system.

The locking of the rotation angle of each panel 1200, 1300, 1400, and 1500 may be activated by levers or switches, e.g., on each of the respective panels. Further the locking, or any other actuation described herein may be performed manually or automatically by an actuator (e.g., a motor, leadscrew, hydraulic piston, pneumatic piston, and/or any other suitable actuator).

Figure 17:
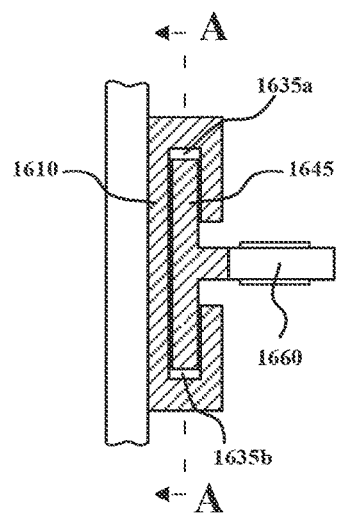
FIG. 17 is an end view of the guide chassis and guide channel of FIG. 13.
Figure 18:
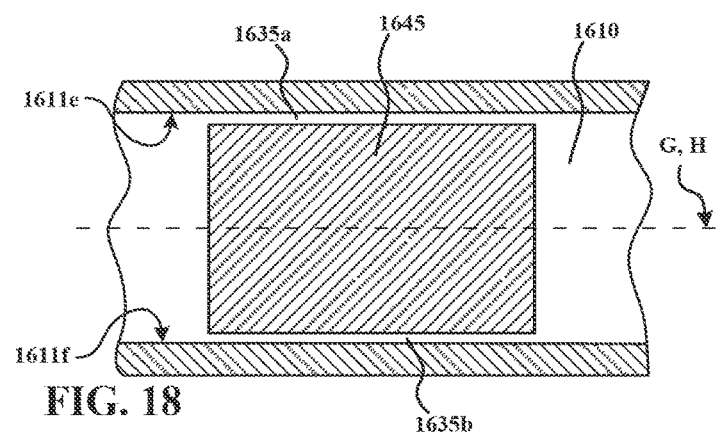
FIG. 18 is a cross sectional-view taken through line A-A of FIG. 17.

Although the proximal portions of the third and fourth panels 1400 and 1500 are laterally supported by the guide mechanisms 1600, the weight of the third and fourth panels 1400 and 1500 is supported by respective sets of casters including casters 1050f and 1050g for third panel 1400 and casters 1050h and 1050i for fourth panel 1500. Accordingly, on flat, even surfaces, the guide plates 1645 of the guide carriages 1640 are maintained level and at an approximately centered distance relative to upper and lower channel surfaces 1611e and 1611f, leaving upper and lower clearances or gaps 1635a and 1635b, as illustrated in FIGS. 17 and 18.

Figure 19:
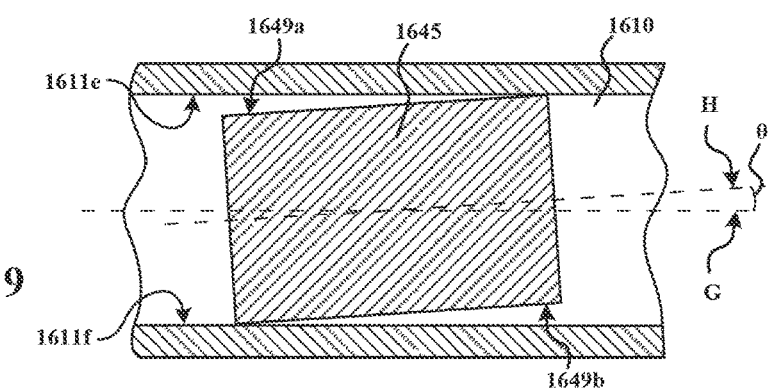
FIG. 19 is a cross sectional-view taken through line A-A of FIG. 17 when one of the panels is on an upslope.

Providing the substantial clearances 1635a and 1635b provides forgiveness and helps prevent binding of the mechanisms 1600 on uneven surfaces. For example, FIG. 19 illustrates a situation where the fourth panel 1500 is on a slight upslope relative to a flat horizontal surface supporting the base 1100 and second panel 1300. Having both casters 1050h and 1050i of the fourth panel 1500 in contact with the up-sloped support surface causes the guide plate 1645 to be rotated with respect to the guide channel 1610. This results in longitudinal axis H of the guide plate 1645, which in FIG. 18 aligns with the channel or path axis G, being angled at an angle θ relative to the axis G.

Figure 20:
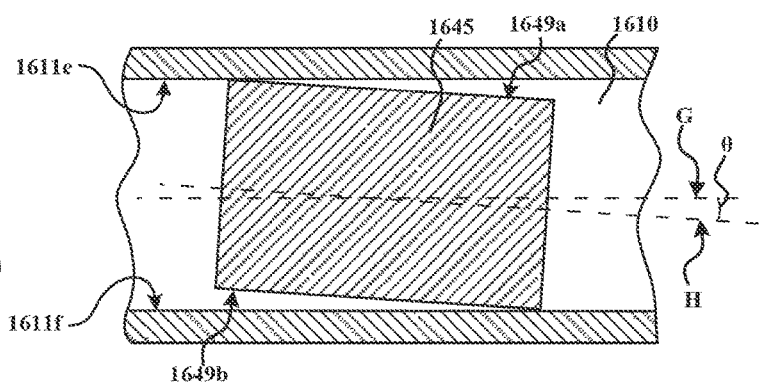
FIG. 20 is a cross sectional-view taken through line A-A of FIG. 17 when one of the panels is on a downslope.

Similarly, FIG. 20 illustrates a situation where the fourth plate 1500 is on a slight downslope relative to a flat horizontal surface supporting the base 1100 and second panel 1300. Having both casters 1050h and 1050i of the fourth panel 1500 in contact with the down-sloped support surface causes the guide plate 1645 to be rotated with respect to the guide channel 1610. This results in longitudinal axis H of the guide plate 1645 being angled relative to the axis G such that the angle θ is negative.

The maximum and minimum for the angle θ is determined in this example by the extent to which the guide plate 1645 can rotate in each direction before the upper or lower surface 1649a or 1649b of the guide plate 1645 contacts the upper or lower surface 1611e or 1611f of the guide channel 1610. Although any suitable range of rotation of the guide plate 1645 may be provided, in some implementations, the range of motion may include an angle θ that can vary, for example, (a) from 30 degrees to negative 30 degrees, (b) from 25 degrees to negative 25 degrees, (c) from 20 degrees to negative 20 degrees, (d) from 15 degrees to negative 15 degrees, (e) from 10 degrees to negative 10 degrees, (f) from 8 degrees to negative 8 degrees, (g) from 5 degrees to negative 5 degrees, or (h) from 3 degrees to negative 3 degrees. In some implementations, the permissible range for angle θ is selected based on intended applications. For example, in a hospital setting with relatively flat floors, a much smaller range of angles may be needed as compared to a surface in a field application such as, e.g., a war zone or disaster relief setting where the ground/support surface to the base 1100 would be much more irregular.

Figure 21:
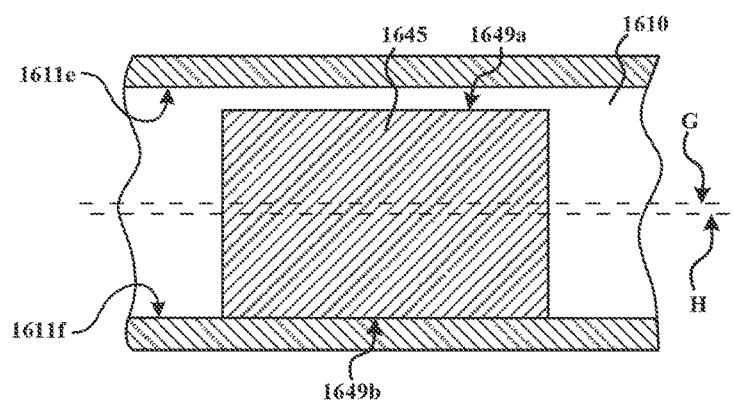
FIG. 21 is a cross sectional-view taken through line A-A of FIG. 17 when one of the panels is supported on a lowered parallel surface.

FIG. 21 illustrates a situation where the fourth plate 1500 is on a surface that is parallel but lower than the surface supporting the base 1100 and second panel 1300. Having both casters 1050h and 1050i of the fourth panel 1500 in contact with the lower parallel surface causes the guide plate 1645 to be translated downwardly with respect to the guide channel 1610 up until a limit set by contact between the lower surface 1649*b* of the guide plate 1645 and the lower surface 1611*f* of the channel 1610. Similarly, having the fourth plate 1500 is on a surface that is parallel but higher than the surface supporting the base 1100 and second panel 1300 would cause the guide plate 1645 to be translated upwardly with respect to the guide channel 1610 up until a limit set by contact between the upper surface 1649*a* of the guide plate 1645 and the upper surface 1611*e* of the channel 1610.

As indicated above, the sterilization unit includes a control system that manages various aspects and functions of the sterilization unit 1000, including, inter alia, selectively controlling the multiple UV-C sources. In some examples, the control system will determine what orientation the unit 1000 is in and activate one or more UV-C sources 1060 (e.g., as determined by the control system based on the unit orientation) for calculated or predetermined periods of time that may be the same or different among the activated UV-C source or sources (e.g., on a source by source or panel by panel basis).

The control system in the illustrated example includes a touchscreen 1810 which serves as both a display and an input device. It should be understood than any known displays, e.g., non-touchscreen displays, or user input devices, e.g., keyboards, trackpads, and/or mice, may be provided in addition or instead of a touchscreen.

FIGS. 22A to 22D include screen shots of example software in accordance with an example embodiment.

Figure 22A:
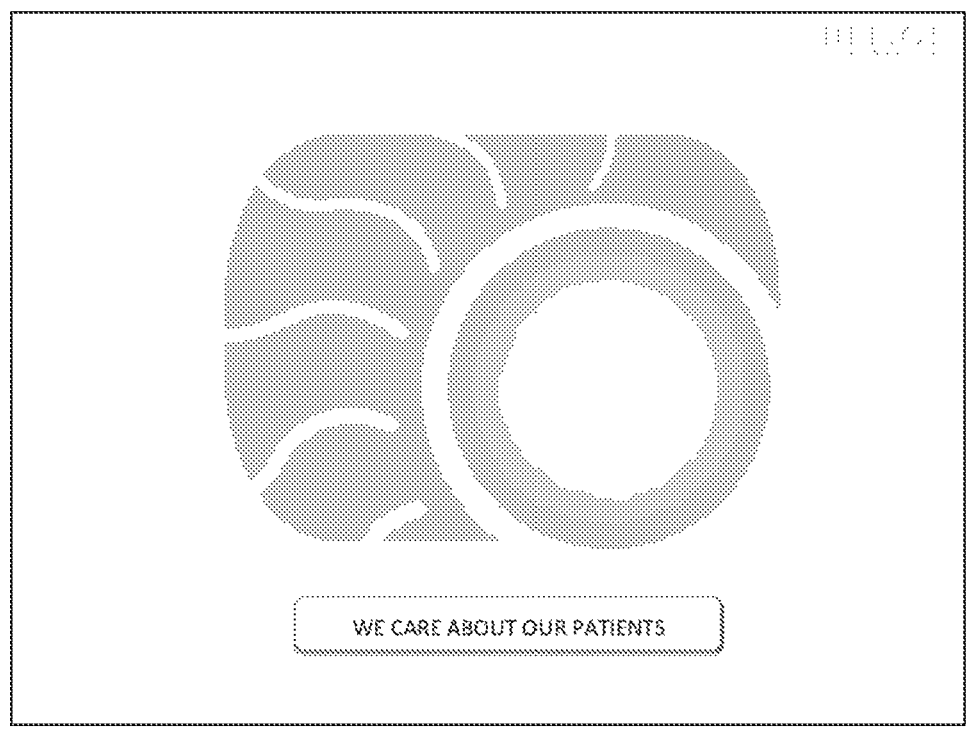
FIGS. 22A to 22E show screenshots of a computer interface of the sterilization unit of FIG. 1.

FIG. 22A is an initial start screen after powering up the unit 1000, e.g., plugging in a receptacle and/or activating a battery-based power supply, and settings have been loaded by a computer processor from a data storage device, e.g., any known computer data storage physically or wirelessly connected to the data storage computer allowing for internet/web connectivity and communication. Once this screen appears, the button at the bottom may be pressed to move to the next screen, which is illustrated in FIG. 22B.

Figure 22B:
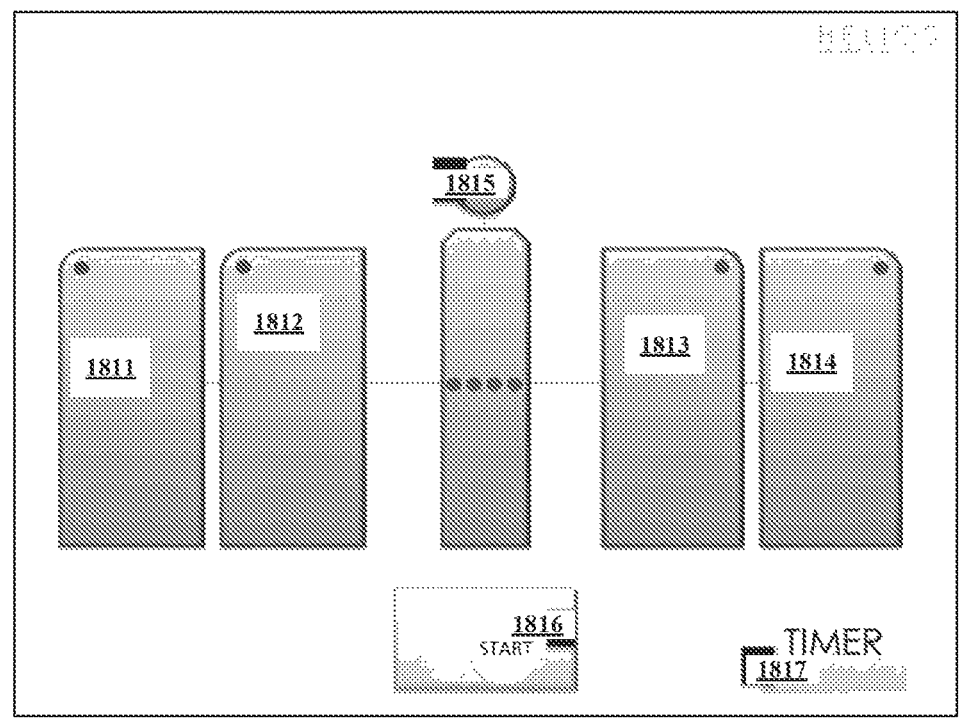
Figure 22C:
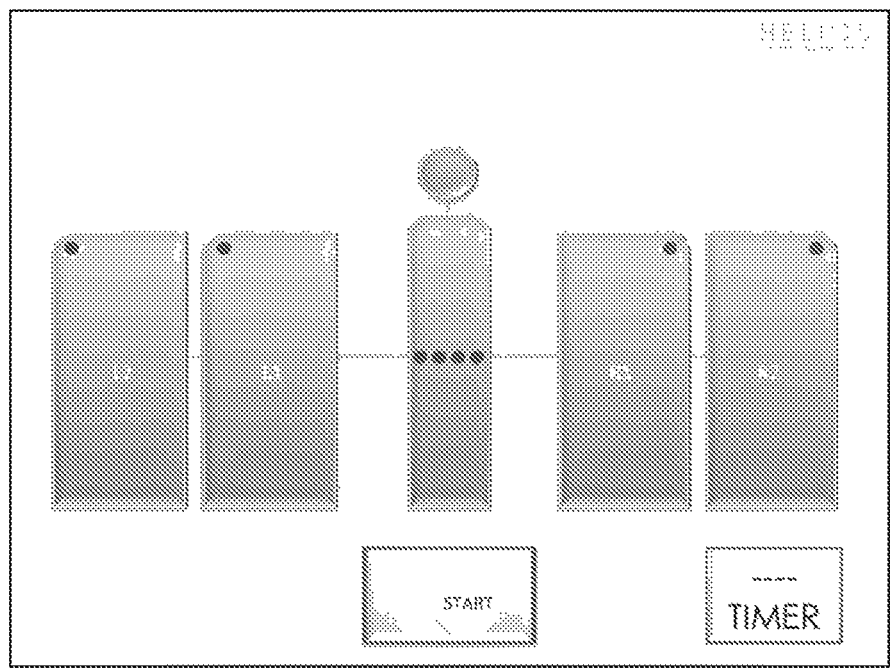

FIG. 22B is the control screen, which is the main screen for the sterilization unit 1000. In this example, it appears after the initial start screen. This screen is utilized to control the sterilization cycles of the sterilization unit 1000. From this screen, the user is able to select or deselect the panels (i.e., the first panel 1200, second panel 1300, third panel 1400, and/or fourth panel 1500 in the illustrated example) that will be needed for the sterilization process. The timer allows the user to choose the appropriate exposure time in seconds and the start button initiates the sterilization cycle. The user can click on the appropriate button or buttons for the desired action, e.g., the examples described herein. The buttons of the main screen control in the illustrated example are:
  (1811)—Left Extended Panel. This button corresponds to the third panel 1400 of the sterilization unit 1000.
  (1812)—Left Inner Panel. This button corresponds to the first panel 1200 of the sterilization unit 1000.
  (1813)—Right Inner Panel. This button corresponds to the second panel 1300 of the sterilization unit 1000.
  (1814)—Right Extended Panel. This button corresponds to the fourth panel 1500 of the sterilization unit 1000.
  (1815)—Extension Arm. This button corresponds to the cantilevered pivot mechanism 1700 of the sterilization unit 1000.
  (1816)—Start Button. This button begins one or more selected sterilization programs to perform a sterilization cycle.
  (1817)—Timer Button. In this example, the time is entered in seconds and corresponds to a desired sterilization time.

When a panel button is selected, a border around the button icon changes, e.g., turns to green, to indicate that the panel has been selected. Any one or more panels may be selected or deselected based on what panels are needed or not needed according to the positioning and specific configuration of the device.

Figure 22D:
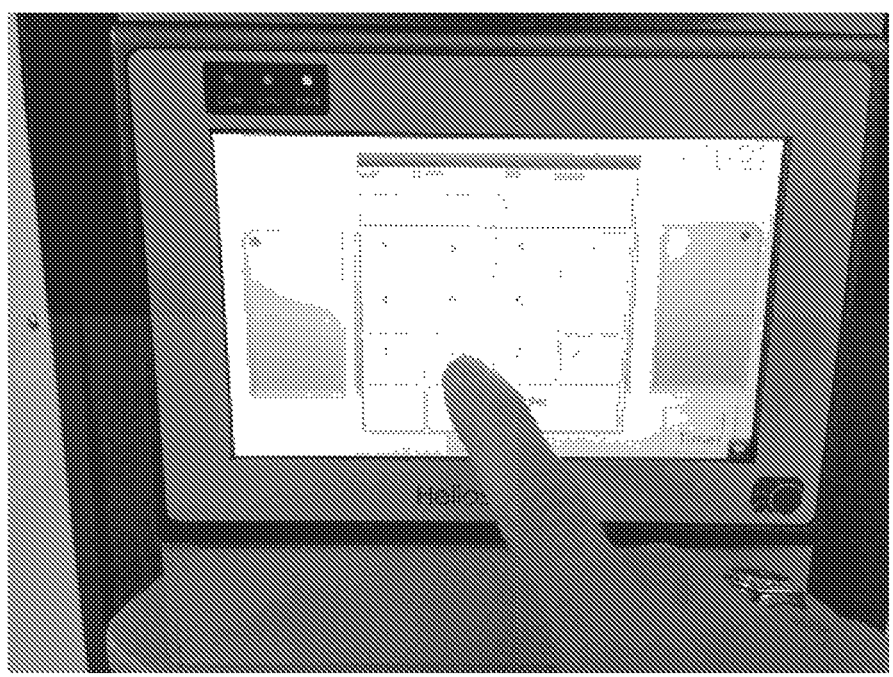

Referring to the screenshot of FIG. 22D, the timer button 1817 of the human-machine interface (HMI) launches a numeric keypad via which the operator may enter a desired sterilization time for the certain type of sterilization being performed. For example, if the required sterilization time is 60 seconds, the user would type in "60," corresponding to 60 seconds of UV-C radiation emitted from the selected panels.

Figure 22E:
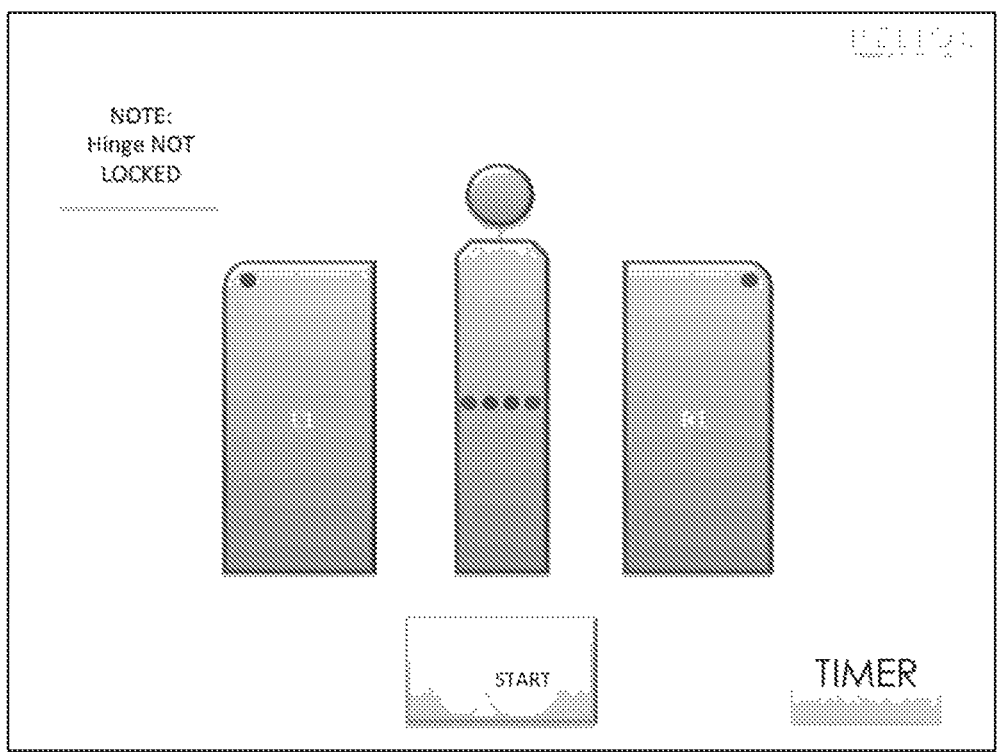

Referring to FIG. 22E, the illustrated screen may appear when the left hinges 1120*a* and/or 1120*b* and/or right hinges 1120*c* and/or 1120*d* are not locked. Further, locking systems in connection with guide mechanism 1600 are monitored. In this regard, if the third or fourth panel 1300 or 1400 is not distally extended and locked in its rotated position relative to respective first or second panel 1200 or 1300, then the respective third or fourth panel 1300 (or both if neither is extended and locked) is not shown on the screen or is otherwise indicated as not being activated.

In this example, the screen is showing the operator that hinge locks for both the first and second panels 1200 and 1300 are not engaged and therefore two red indicators at the two outer most positions. Once they both are engaged, the screen will return to the normal Control Screen.

In some examples, the computer processor may present the user with a menu of predefined sterilization programs, which may or may not ask for particular parameters from the user. These programs may automatically determine, inter alia, the panels, UV-C light sources, and/or sterilization times to be utilized. In some examples, the sterilization unit is fully or substantially automated, such that the unit 1000 itself automatically actuates (e.g., slides, rotates, locks, etc.) the panels into the orientations needed for a selected program. In some examples, the processor provides the user with instructions for manually configuring the panel orientation for a selected program. In some examples, the sterilization unit 1000 includes sensors that verify that the panels are in the correct orientation for the particular program. In some examples, the processor prevents the selected program from proceeding until the panels are in the required orientation and, in some examples, locked.

In some examples, the unit 1000 is self-reporting for parameters such as, for example, UV-C light intensity, in order for the unit 1000, e.g., via the control system, to determine if there are any problems with the operating state of the unit 1000.

In some examples, the processor may adjust an electrical power applied to one or more particular UV-C source based on age-based degradation of the output intensity of the source, e.g., a fluorescent bulb. This may be, for example, in response to a smart sensors system to provide internal feedback of the overall functionality and health of the sterilization unit.

The processor may also be able to send and receive signals, e.g., wirelessly, to indicate that particular items or locations have been sterilized and/or that indicate items or locations that are in need of sterilization.

In some examples, the processor adjusts light intensity and duration based on a selected sterilization program or configuration.

In some examples, the control system is configured to identify specific areas and/or items based on identifiers such as, for example, RFID tags, bar codes, or any other suitable mechanism.

Figure 23A:
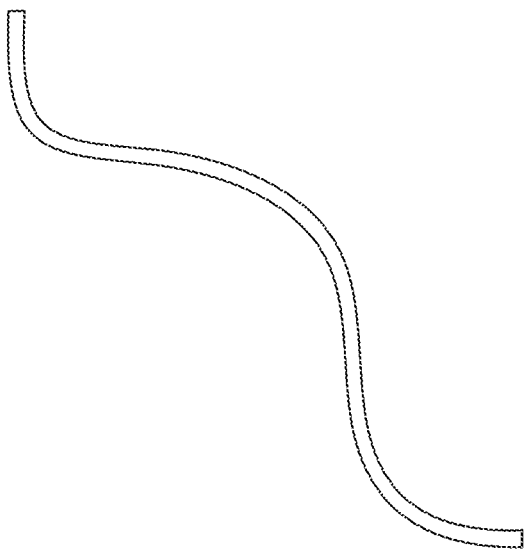
FIGS. 23A to 23C schematically illustrate variations of configurable sterilization units.
Figure 23B:
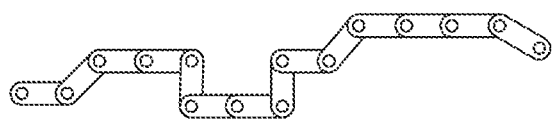
Figure 23C:
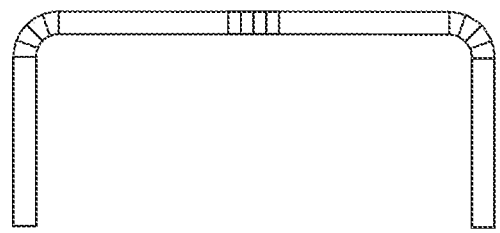

Although some example implementations described herein include four panels, it should be understood that other examples may include any suitable number of panels, including a single panel. Referring to the schematic illustrations of FIGS. 23A to 23C, which are top views, other examples may include bendable panels and/or connectors (see FIGS. 23A and 23C) and/or a plurality of very narrow panels (see FIG. 23B).

FIGS. 24A to 33A of other example implementations, in the form of sterilization units 100 and 200. The sterilization units 1000, 100, and 200 shown and described herein generally share all features in common except to the extent indicated otherwise.

An "L-shaped" or central sterilization structure as discussed herein may, in some implementations, refer to a structure comprising two appendages that extend from a center portion or vertex of the structure (i.e., the direct or indirect meeting point of the two appendages, or structure at the intercept or vertex of the two appendages—e.g., a central beam, a direct meeting point of the appendages, etc.). For embodiments of indirect attachment the two appendages may be connected to a center portion or vertex in any acceptable way. In some embodiments, appendages may be directly attached to support beams, which may be attached to the center portion or vertex, thereby indirectly attaching the appendages to one another through the center portion or vertex structure. The central sterilization structure, may in some implementations be configured such that the two appendages are capable of forming substantially a right angle (i.e., 90°±10°) with one another, whether attached directly or indirectly. While the central sterilization structure is operational in various conformations, some of which are described herein, the central sterilization structure is intended to be, and is operational to sterilize a space, surface, or structure when configured in an open configuration, e.g., at substantially right angle or at any other suitable angle, and when the faces of the panels of the invention are vertically oriented (i.e., perpendicular to a floor). Although some implementations may be described as "L-shaped," it should be understood that example implementations of the present invention may take many different shapes other than L-shaped units.

In some embodiments, the two appendages, e.g., panels, of the central sterilization structure are capable of forming, e.g., an angle of 90±45°, 40°, 35°, 30°, 25°, 20°, 15°, 10°, or 5°, as well as many other angles outside this range, as set forth herein.

In some embodiments, the central sterilization structure is a single, unitary structure, such that the two appendages represent a continuous single structure. The single structure may be rigid, such that the appendages are relatively non-movable in relation to one another, or flexible, such that the appendages are able to move in relation to one another.

Figure 24A:
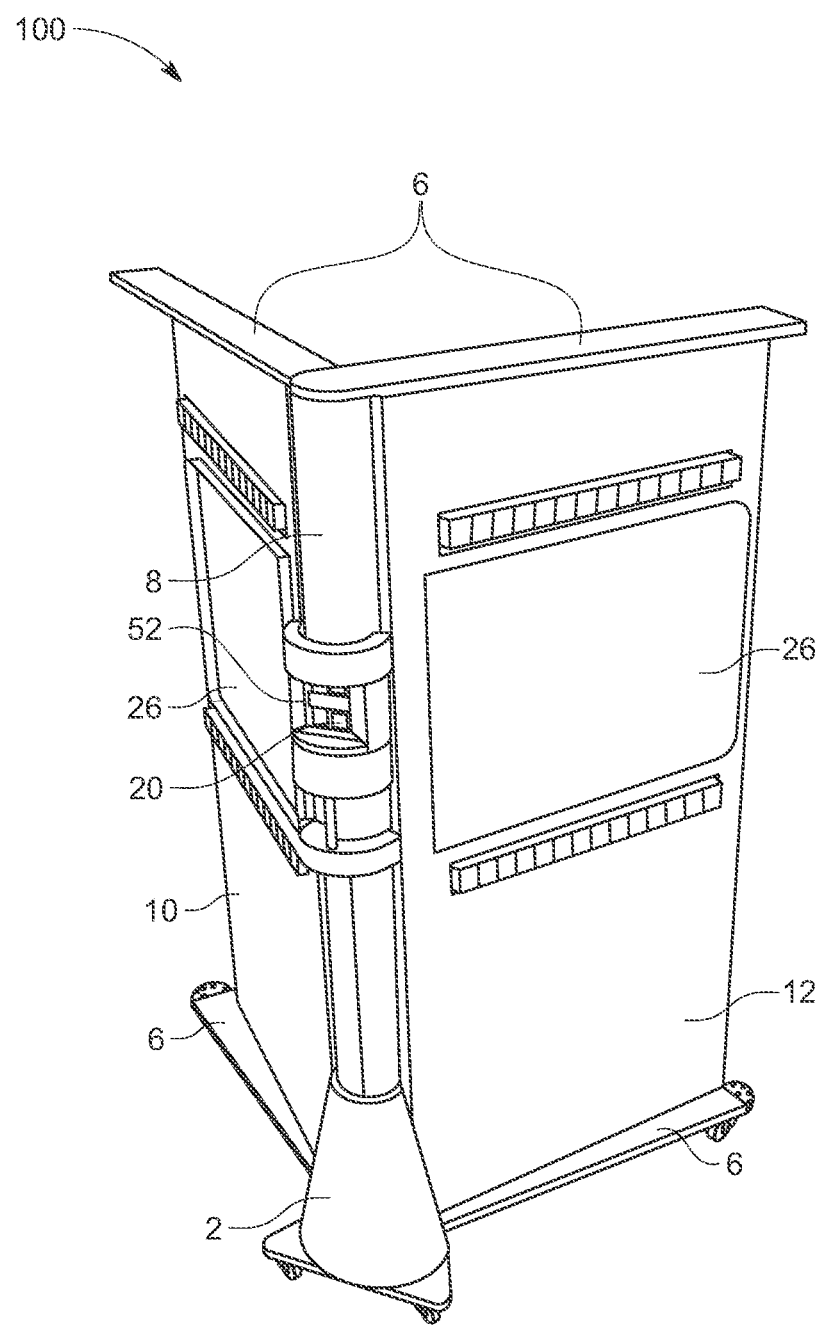
FIG. 24A is a perspective view of a sterilization device according to an example implementation, and depicts an outer view of a central sterilization structure of the embodied device.

FIG. 24A is a perspective view of a sterilization device or unit 100 according to an example embodiment, and depicts an outer view of a central sterilization structure. In various embodiments, the outer face of the central sterilization structure is intended to be the point of operation, or the user interface for devices of the invention.

The sterilization device shown in FIG. 24A comprises a first panel 10 and a second panel 12 that are hingedly attached to one another to form a central sterilization structure. More specifically, first panel 10 is indirectly hingedly attached to second panel 12 through central beam 8. Central beam 8 is connected to base 2. In the depicted embodiments, central beam 8 is essentially a hollow tube structure, to which support beams 6 are configured to connect. In particular, first panel 10 is connected to support beams 6, positioned at the top and bottom of panel 10, and second panel 12 is connected to support beams 6, positioned at the top and bottom of panel 12. The support beams 6 connected to panels 10 and 12 are connected to central beam 8, which thereby functions as a point of attachment, or vertex structure, for panels 10 and 12. Accordingly, in the depicted embodiment, first panel 10 and second panel 12 are attached to one another via central beam 8, even though the panels do not necessarily directly touch central beam 8. Support beams 6 also enhance the structure and stability of the depicted central sterilization structure.

The first panel 10 has a first face (pictured) and a second face (not pictured), the first face forming a part of the outer face of the central sterilization structure, the second face forming a part of the inner face of the central sterilization structure. The second panel 12 has a first face (pictured) and a second face (not pictured), the first face forming a part of the outer face of the central sterilization structure, the second face forming a part of the inner face of the central sterilization structure. In the depicted embodiment, the outer portion of central beam 8 (as shown), also forms a part of the outer face of the central sterilization structure and acts as the pivotal axis which formulates the hingedly attached joint that enables pivotal motion. The first face of the first panel 10, the depicted portion of central beam 8, and the first face of the second panel 12 are the major constituents forming the outer face of the central sterilization structure of the device 100 of FIG. 24A.

In some embodiments, sterilization devices of the invention comprise one or more (e.g., two, three, four, etc.) windows, which allow a user to see through a sterilization device of the invention so as to, e.g., accurately position the device and the object(s) (e.g., space, surface, or structure) intended to be sterilized. In preferred embodiments, the windows are UV-protecting windows, which do not permit penetration of harmful UV radiation. Sterilization device 100 of FIG. 24A includes two UV-protecting windows 26.

FIG. 24A depicts a sterilization device 100 having a control or management mechanism 20 located on a base or central beam 8 on the outer face of the central sterilization structure. In the depicted device, the management mechanism 20 comprises, inter alia, a control panel for operating one or more UV-C radiation sources, and a control screen.

In various embodiments, the sterilization device of the invention comprises one or more (for example, 1, 2, 3, 4, etc.) additional panels attached (e.g., adjacent to and typically connected to in any art-acceptable manner) to the central sterilization structure. In some embodiments, the one or more additional panels are fixedly attached to the, e.g. L-shaped, central sterilization structure. In some embodiments, the one or more additional panels are moveably attached to the central sterilization structure in any desired or art-acceptable manner. For example, in some embodiments, the one or more additional panels are each individually slidingly, translationally, hingedly, and/or rotationally attached to the central sterilization structure. In some embodiments, one or more additional panels is fixedly attached to the central sterilization structure and one or more additional panels is moveably attached to the central sterilization structure. In some embodiments, there are two or more additional panels attached to the central sterilization structure. In some embodiments, the one or more additional panels are at least slidingly attached to the central sterilization structure.

Figure 24B:
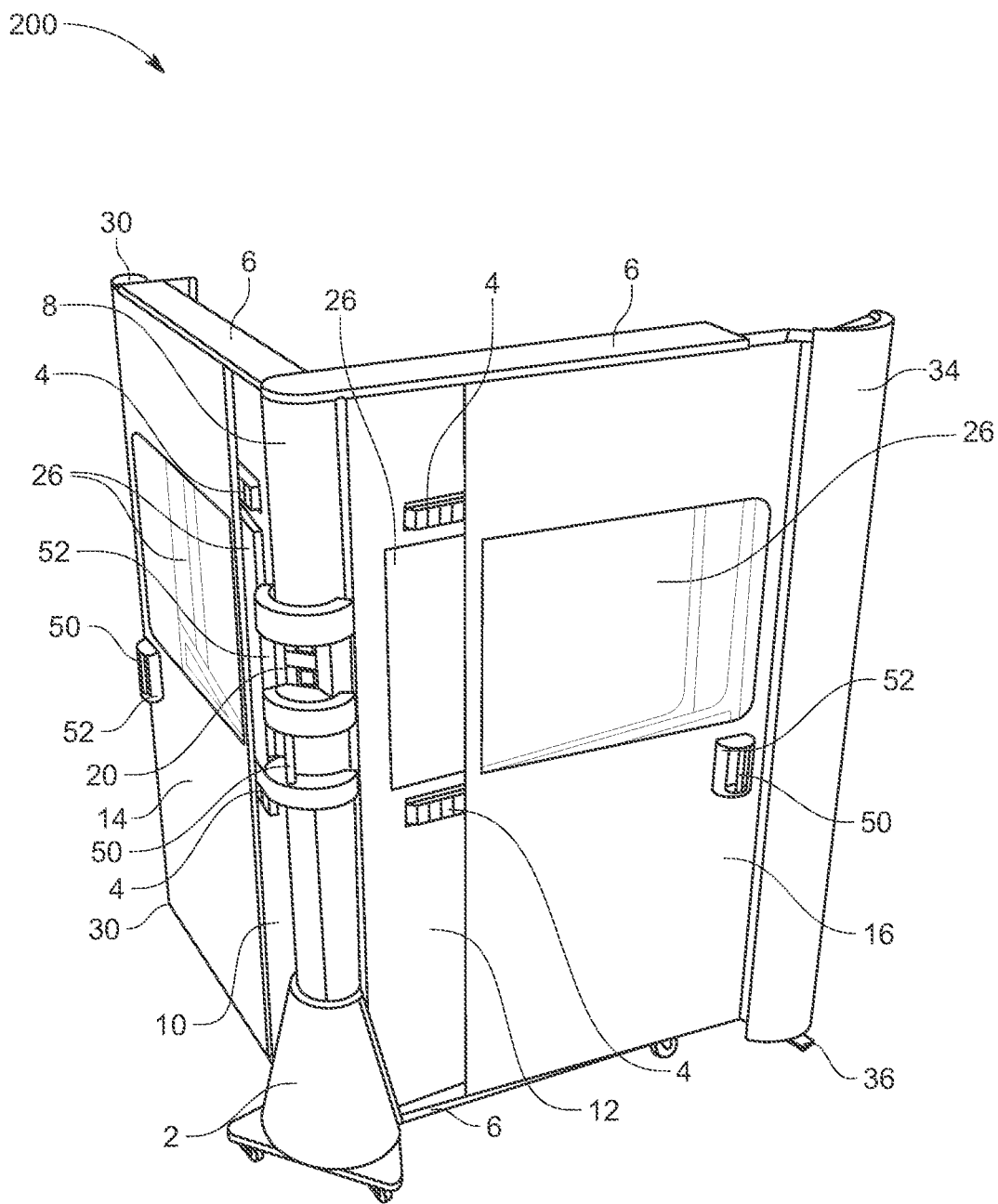
FIGS. 24B and 24C are perspective views of a sterilization device comprising the central sterilization structure of the device shown in FIG. 24A, except the device shown in FIGS. 24B and 24C comprises two additional panels attached to the central sterilization structure, shown in substantially retracted positions.
Figure 24C:
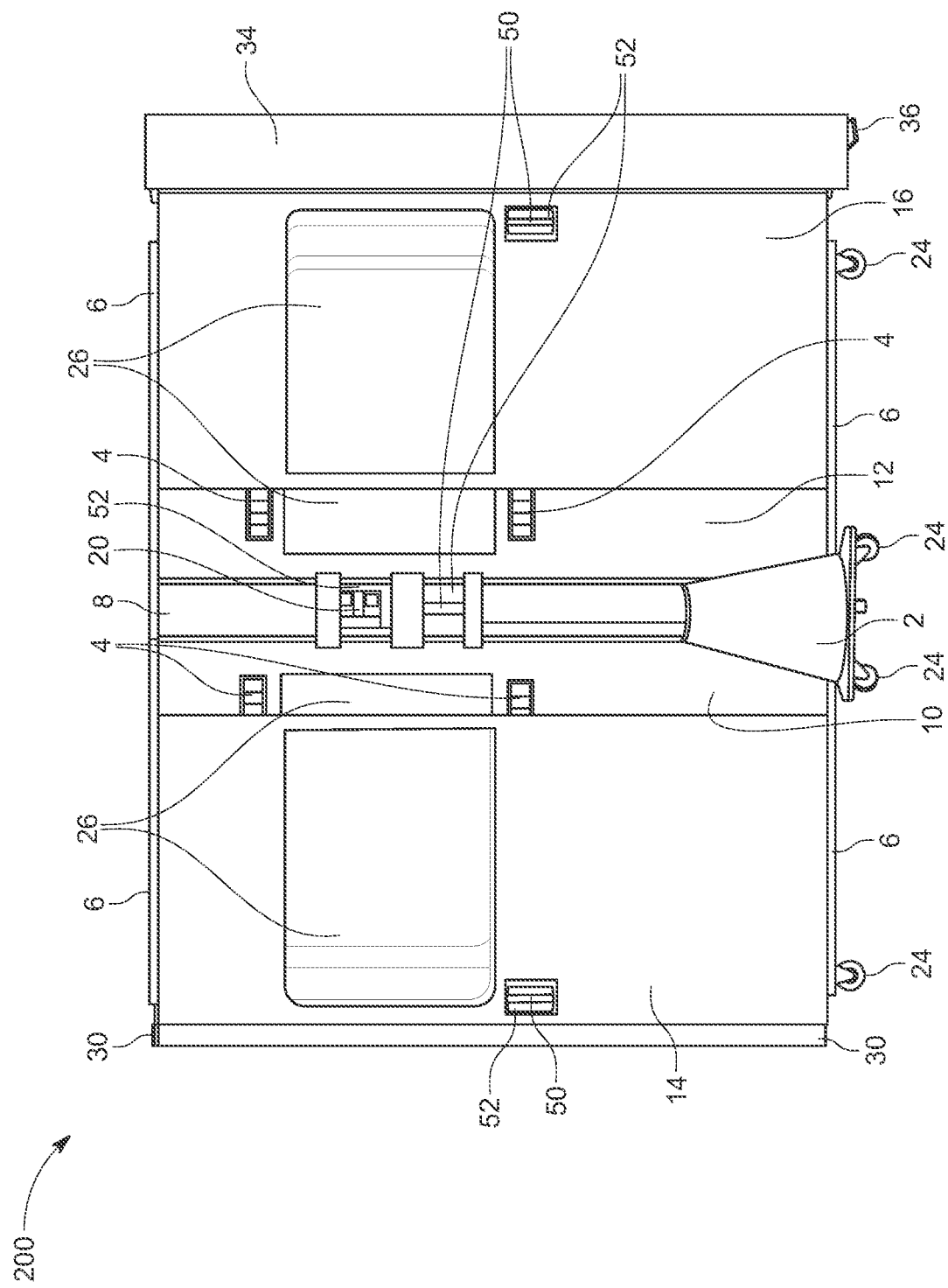

FIGS. 24B and 24C are perspective views of a sterilization device 200 comprising the central sterilization structure of the device 100 shown in FIG. 24A, except the device 200 shown in FIGS. 24B and 24C comprises two additional panels 14 and 16 slidingly attached to the central sterilization structure. The two additional panels 14 and 16 are shown in substantially retracted positions, where a majority of panels 10 and 12 is eclipsed behind panels 14 and 16, respectively. Panels 14 and 16 slide parallel adjacent to panels 10 and 12, respectively, of the central sterilization structure, such that the additional panels of the sterilization device 200 may be fully refracted, retracted to a certain extent, or extended fully or to any desired extend. Panels 14 and 16 extend from the central sterilization structure by sliding outwardly away from central beam 8 by any acceptable means, for example, along tracks 4, located on first panel 10 and second panel 12. In other embodiments utilizing tracks to enable sliding of panels, the tracks may be located in any other desirable position/location on the sterilization device 200, for example, at the top and bottom of the first faces of each of the first panel 10 and the second panel 12.

The device 200 of FIGS. 24B and 24C includes four UV-protecting windows 26.

The device 200 of FIGS. 24B and 24C comprises management mechanism 20, which, as in FIG. 24A, comprises, inter alia, a control panel for operating one or more UV-C radiation sources, and a control screen. The management mechanism 20 incorporates software that controls self-sterilization mechanisms 52 in a self-sterilization process. The management mechanism 20 also allows for controlling operation of (including e.g., intensities and exposure times) the UV-C radiation sources 40.

In some embodiments, panels of the sterilization device comprise coupling mechanisms, which are configured to enable the attachment (e.g., connection, joining, etc.) of one panel to at least one other panel. In some embodiments of the invention, the sterilization device is operable without utilizing the coupling mechanisms, whereas in other embodiments, the coupling mechanisms are used during operation of the device. The coupling mechanisms may be any mechanism that can serve the intended purpose of enabling attachment. For example, the coupling mechanisms may be, e.g., magnetic, fasteners (e.g., hook and loop fasteners, for example, fabric, plastic, etc.), coupling hinges and pins or other suitable counter coupling mechanism. In various embodiments, the coupling pin in the coupling column acts as a "ball and socket" ("pin and socket" as used in the depicted embodiment) connection with the coupling hinge. While the pin and hinge are interlocked when forming various contained configurations, the pin socket connection also provides some pivotal capabilities to the panels of the device of the invention. In some embodiments, one or more additional panels attached to the central sterilization structure comprise coupling mechanisms.

In the sterilization device 200 shown in FIGS. 24B and 24C, additional panels 14 and 16 comprise, as coupling mechanisms, coupling hinges 30, coupling pins 32 (not pictured in FIGS. 24B and 24C; see, e.g., FIG. 26), coupling column 34, and coupling control 36. In the sterilization device 200, additional panel 14 has two coupling hinges 30, although other embodiments may have no coupling hinges, only one coupling hinge, or more than two coupling hinges. The coupling hinges 30 are configured to align with, and be able to unite with coupling pins (not shown) on coupling column 34 on additional panel 16, such that additional panels 14 and 16 may be attached, when desired. Coupling (attachment of panels) occurs via coupling control 36. In various embodiments, where present, the coupling control 36 can be initiated electronically, or mechanically. In the mechanical version of the depicted embodiment, the coupling control 36 functions as a lever arm and when pressed (e.g., by a user's foot) it retracts the coupling pins. Upon the release of the control lever the pins engage with the coupling hinge and form the junction. In the case of an electrical control, this process can be initiated by the management mechanism and instead of having a mechanical junction it could be substituted for, e.g., a magnetic junction.

In various embodiments, the sterilization device is portable (e.g., movable, transportable). In some embodiments, the device is easily portable. For example, in some embodiments, the device is configured to be easily moved from one location to another. The device 200, as shown. e.g., in FIG. 24C, comprises wheels or casters 24, which make the device easily portable from one location to another. By virtue of wheels 24, device 200 is easily portable even while it remains configured in the vertical position depicted (the configuration in which the device is intended to be able to operate). This is an advantage over various prior art devices, which are not portable when configured in their intended operational configuration.

In certain embodiments, the sterilization device comprises one or more points of contact. As used herein, a "point of contact" is a designated area or mechanism on the sterilization device intended to represent a location on the device that a user would make contact with to maneuver the device. A common, non-limiting example of a point of contact is a handle. In some embodiments, at least one point of contact is located on the outer face of the central sterilization structure of a device according to the invention.

In certain embodiments, the sterilization device of the invention comprises one or more self-sterilization mechanisms. As used herein, a "self-sterilization mechanism" is a mechanism of the device of the invention that functions to sterilize a portion of the device that is not generally otherwise subjected to UV-C radiation from the UV-C radiation sources that are configured to sterilize a space, surface, or structure. In some embodiments, one or more self-sterilization mechanisms of the invention are located on the outer face of a central sterilization structure. In various embodiments, self-sterilization mechanisms include chambers which, in some embodiments, comprise one or more points of contact. The chamber self-sterilization mechanisms may be configured to sterilization the one or more points of contact.

As shown in FIG. 24C, device 200 includes points of contact 50, which are handles configured to allow a user to maneuver the device 200. In the device 200, points of contact 50 and management mechanism 20 are located in self-sterilization mechanisms 52, which are chambers configured to self-sterilize their contents (i.e., management mechanism 20 and points of contact 50 in device 200). The self-sterilization mechanisms 52 can sterilize using any desired or art-accepted means, for example, using germicidal sprays or UV-C radiation. In various embodiments, the self-sterilization mechanisms 52 are configured to shield a user during the period of self-sterilization. For example, in some embodiments, self-sterilization mechanisms 52 are chambers having cylindrical portions that are configured to cover the interior of the chamber and its contents, thereby containing the chamber and separating the chamber and its contents from a user, and sterilization (e.g., UV irradiation) is performed within the contained chamber. In various embodiments, operation of self-sterilization mechanisms 52 is controlled by management mechanism 20. In some embodiments, the self-sterilization mechanism is used between each sterilization use/cycle of a device of the invention. Where present, self-sterilization mechanisms can serve to prevent the device of the invention from becoming a carrier of pathogens. In such embodiments, the self-sterilization mechanisms prove an advantage over numerous prior art methods and devices by minimizing and/or preventing cross-contamination between the environment and a healthcare worker or patient. The self-sterilization mechanism(s) reduce the risk of the device of the invention itself becoming another transferring body for pathogens during and after a sterilization process and therefore the inventive device is a first of its kind to have embodiments that incorporate a self-sterilization mechanism.

Figure 25:
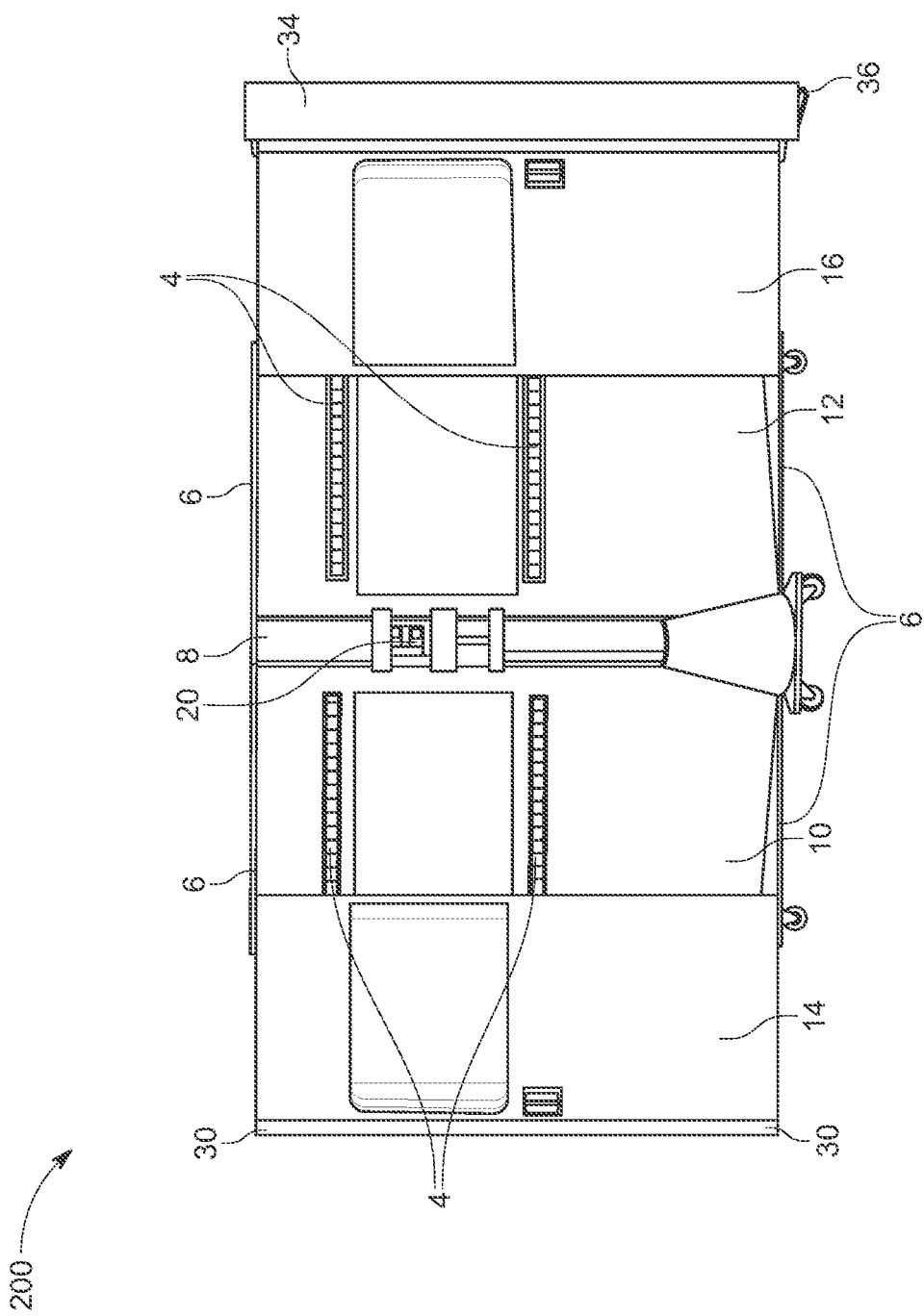
FIG. 25 is a view of the outer face of the central sterilization structure of a sterilization device according to an example implementation, where the central sterilization structure has two additional panels attached thereto, shown in extended positions.

FIG. 25 is a view of the outer face of the central sterilization structure of a sterilization device 200 according to an embodiment of the present invention. In particular, FIG. 25 depicts the device 200 of FIGS. 24B and 24C, where the two additional panels 14 and 16 attached to the central sterilization structure are shown in extended positions. While both of additional panels 14 and 16 are shown in extended positions in FIG. 25, in some embodiments, the device of the invention is configured such that neither (see, e.g., FIG. 24B) or only one of the additional panels is in an extended position. Extending the panels of the device of the invention can be helpful, for example, when sterilizing a larger object or portion thereof (e.g., a larger space, surface, or structure).

Figure 26:
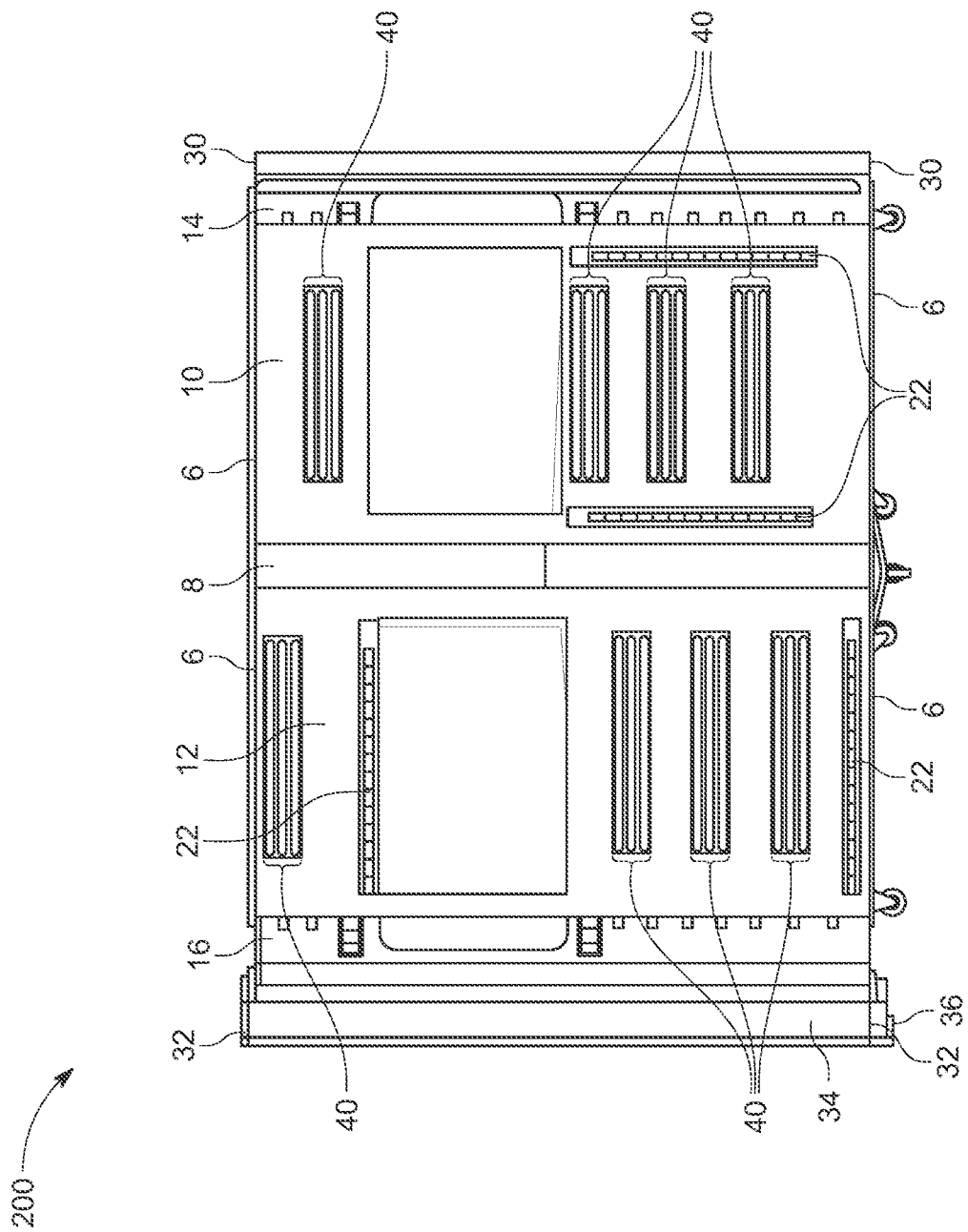
FIG. 26 is a view of the inner face of the central sterilization structure of a sterilization device according to an example implementation. Two additional panels are attached thereto, shown in substantially retracted positions.

FIG. 26 is a view of the inner face of the central sterilization structure of a sterilization device 200 according to an example embodiment. In particular, FIG. 26 depicts the device 200 of FIGS. 24B, 24C, where the two additional panels 14 and 16 attached to the central sterilization structure are shown in substantially retracted positions. The inner face of the central sterilization structure comprises UV-C radiation sources 40. As shown, the inner face of the central sterilization structure comprises the second face of first panel 10, the second face of second panel 12, and the depicted portion of central beam 8. The second face of first panel 10 has four groupings of UV-C radiation sources, with three UV-C radiation sources 40 in each group, for a total of 12 UV-C radiation sources on the second face of first panel 10. The second face of second panel 12 has four groupings of UV-C radiation sources, with three UV-C radiation sources 40 in each group, for a total of 12 UV-C radiation sources on the second face of second panel 12. Accordingly, the inner face of the depicted central sterilization structure has 24 UV-C radiation sources.

FIG. 26 illustrates the inner portion of coupling column 34, which comprises two coupling pins 32, located at the top and bottom of column 34. Coupling pins 32 are configured such that they are capable of meeting and attaching with coupling hinges 30, thereby permitting the sterilization device 200 to be configured in a contained configuration (see, e.g., FIGS. 31 and 32).

In some embodiments, sterilization devices according to the present invention comprise one or more angular mechanisms, which are structures configured to provide further angular positioning for optimal sterilization. The angular mechanisms of embodiments of the invention may be any structure that functions to assist in improving or optimizing the angle of UV-C radiation emitted from the device. In some embodiments, the angular mechanisms are reflective structures. In some embodiments, the angular mechanisms are shaped in any manner to angle UV-C radiation as desire. For example, in some embodiments, the angular mechanisms are convex structures, e.g., a cylinder of a portion thereof. In some embodiments, the angular mechanisms are configured to be stationary, whereas in some embodiments, the angular mechanisms are configured to be movable in any desired manner. For example, in some embodiments, the angular mechanisms extend out from the sterilization device, and can be manipulated into a plurality of different positions. In some embodiments, the angular mechanisms are e.g., robotic arms. In various embodiments, the robotic arms allow for the distribution of UV-C light above, below, right, left, and the opposite sides of a structure being sterilized. For example, for sterilizing, e.g., a hospital bed, in some embodiments, the bed may be positioned long-ways left-right, e.g., close to a wall, but not touching the wall within a room. The device of the invention could then be positioned between a user and the bed, thereby creating a barrier and creating the sterilization field. Once positioned as desired, the robotic arm(s) could extend outwards toward the hospital bed-some arms could be, e.g., positioned above and below and others positioned right & left and some or all of the arms could extend beyond the width of the bed so as to partially curve around the only side of the hospital bed not exposed to the UV-C sources, thereby enhancing the surface area of the bed that would be subject to UV-C exposure.

The sterilization device 200 depicted in FIG. 26 comprises four angular mechanisms 22, which, in the depicted device 200, are robotic arms.

Figure 27:
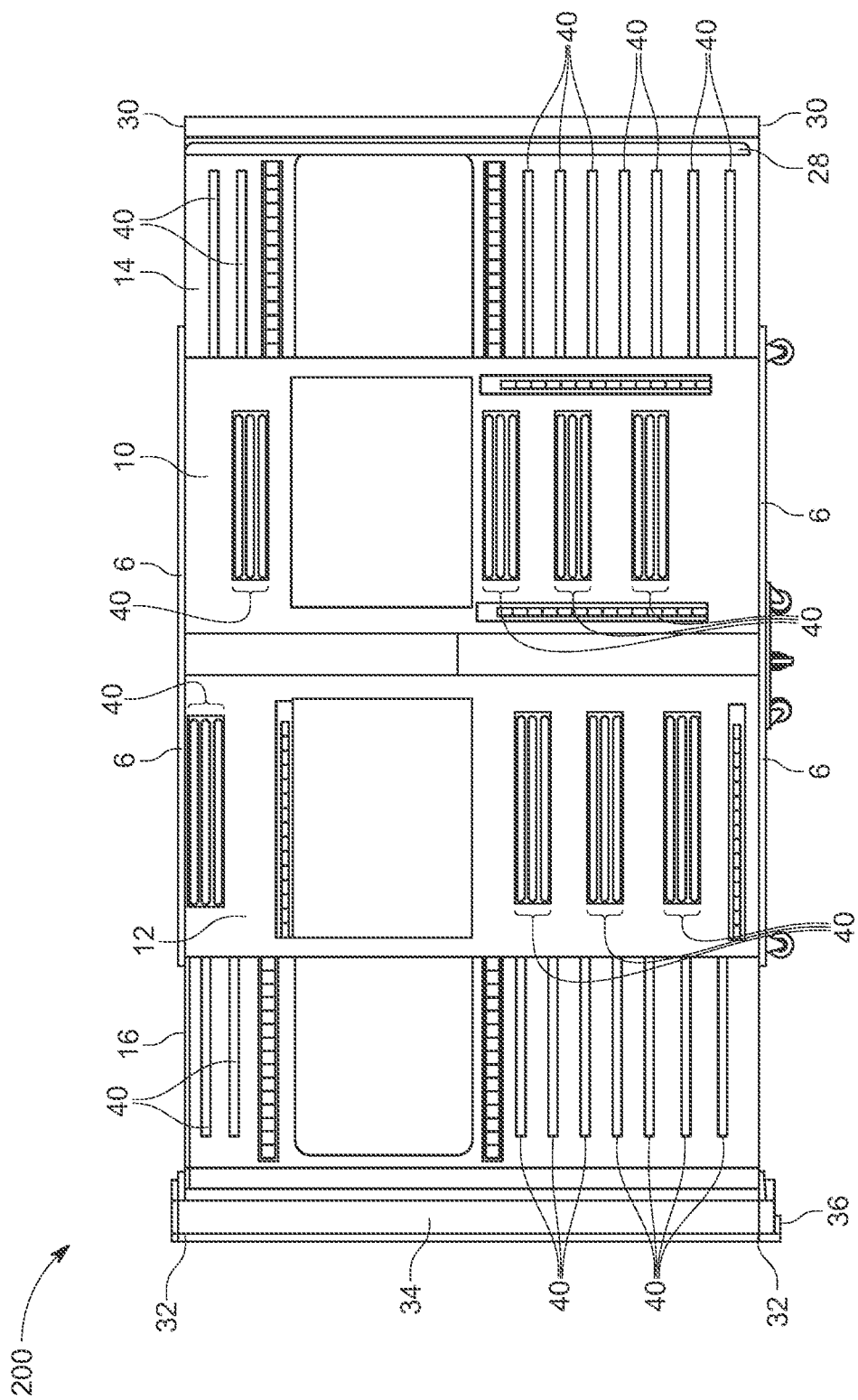
FIG. 27 is a view of the inner face of the central sterilization structure of a sterilization device according to an example implementation. Two additional panels are attached thereto, shown in extended positions.

FIG. 27 is a view of the inner face of the central sterilization structure of a sterilization device 200 according to an embodiment of the present invention. Two additional panels 14 and 16 are attached thereto, shown in extended positions. In particular, FIG. 27 depicts an inner view of the device 200 for which an outer view is shown in FIG. 25. As shown, in addition to the UV-C radiation sources 40 on panels 10 and 12, additional panels 14 and 16 also have UV-C radiation sources 40 disposed thereon, on the inner, second faces of the panels. While device 200 has UV-C radiation sources on each of the panels of the device, other embodiments of the invention have UV-C radiation sources on fewer than all of the panels of the device (e.g., on one, two, or three panels). The panels of the invention may comprise any desirable material(s). The surfaces of the second, inner faces (depicted) of panels 10, 12, 14, and 16 of device 200 comprise a reflective material that reflects UV-C radiation, such as polished aluminum. However, in certain embodiments, the material bordering the edges of one or more second, inner faces of panels used in the invention comprises a material that absorbs UV-C radiation for example pressed zinc oxide, black paint, or china clay. In such embodiments, UV-C splash at and around the edges of the device is reduced and/or prevented. In various embodiments, devices of the invention comprises one or more splash guard(s) 28 that are configured to reduce and/or prevent exposure of users to UV-C radiation around the perimeters of the panels. Coupling column 34 may also function to reduce and/or prevent user exposure to UV-C radiation.

In various preferred embodiments, the sterilization device of the present invention is configured such that users are shielded from, and/or are not exposed to harmful UV-C radiation.

Figure 28A:
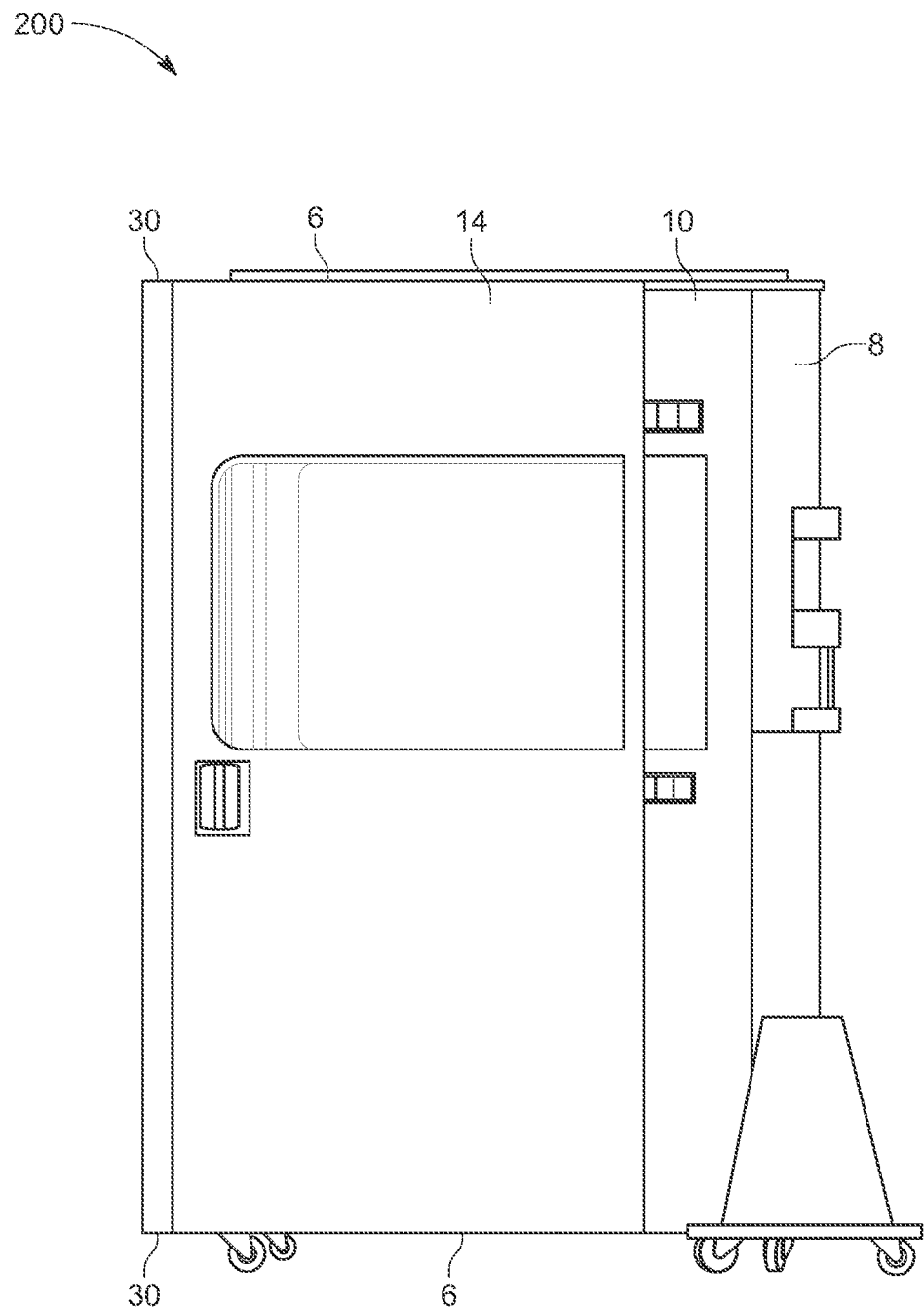
FIGS. 28A and 28B are views of left and right profiles, respectively, of an example implementation.
Figure 28B:
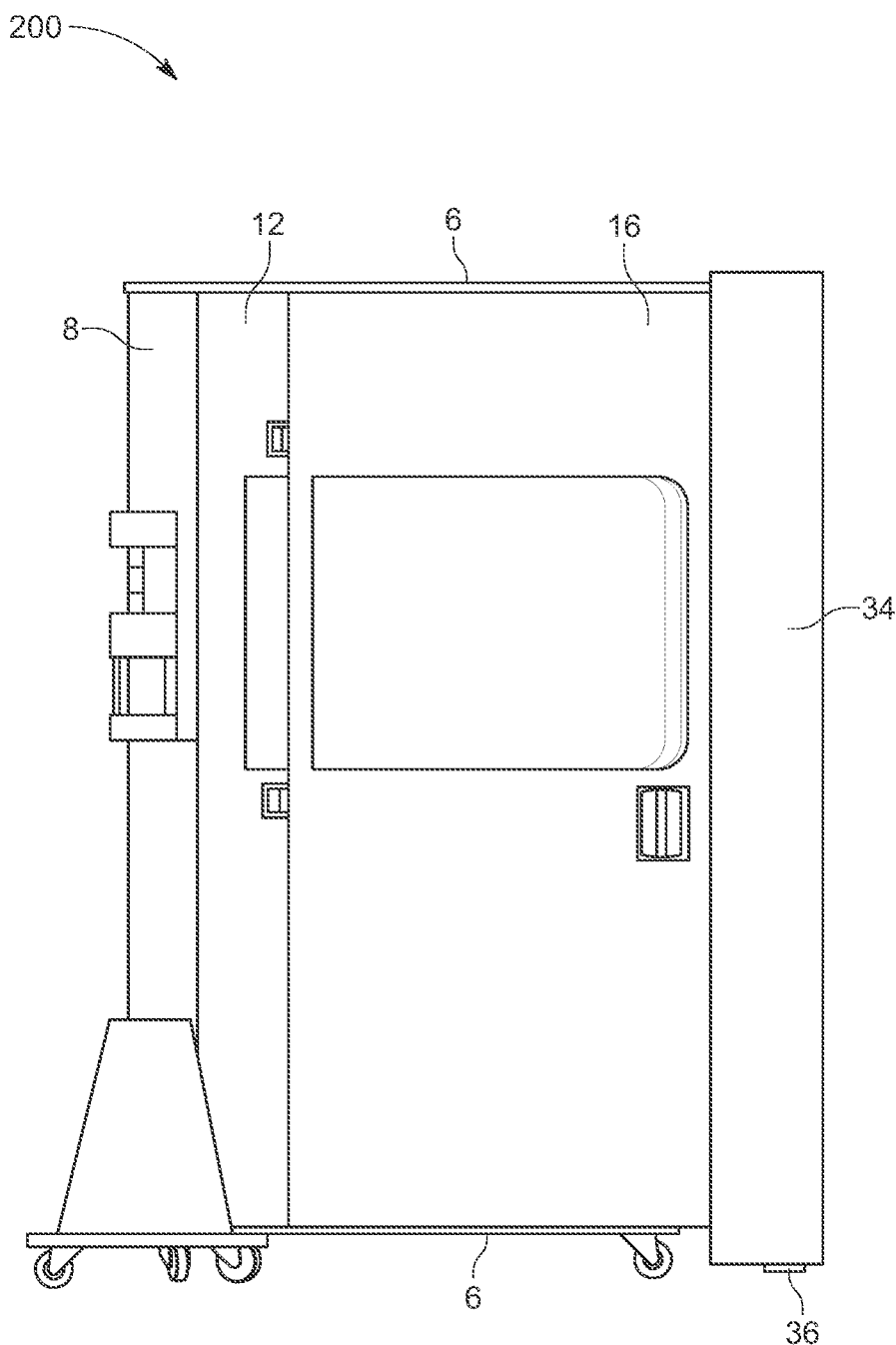

FIGS. 28A and 28B are views of left and right profiles, respectively, of an example embodiment. In particular, FIGS. 28A and 28B are profile views of the device 200 shown in FIGS. 24B and 24C.

Figure 29A:
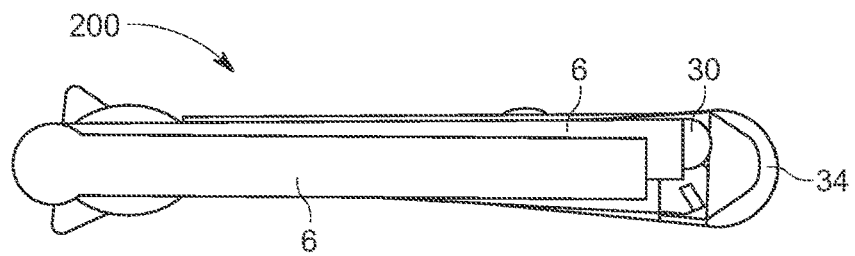
FIGS. 29A-D depict top views of embodiments in different configurations.
Figure 29B:
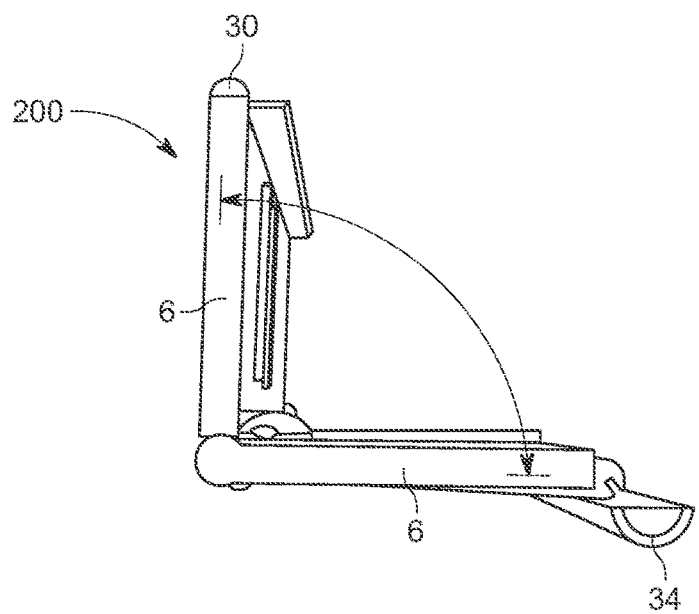
Figure 29C:
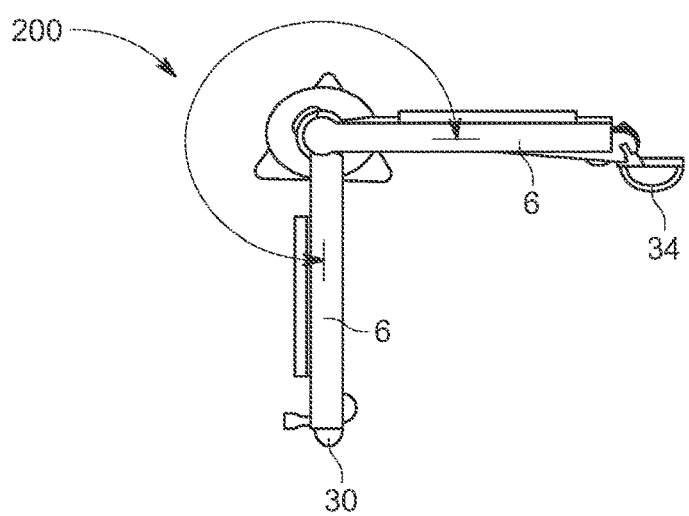
Figure 29D:
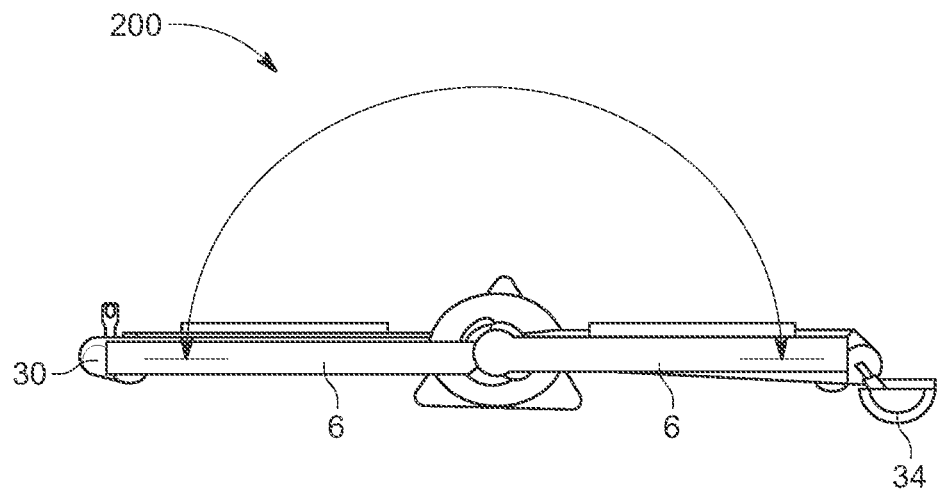

FIGS. 29A-D depict top views of example embodiments in different configurations. In particular, FIGS. 29A-D depict various top views of different rotational configurations of the device 200 shown in FIGS. 24B and 24C. FIG. 29A shows the device 200 of FIGS. 24B and 24C where first panel 10 (not pictured) and second panel 12 (not pictured) are folded into one another, as indicated by the positioning of the depicted support beams 6. FIG. 29B shows the device 200 of FIGS. 24B and 24C in a configuration where panels 10 and 12 (not pictured) are configured in a 90° angle. FIG. 29C shows the device 200 of FIGS. 24B and 24C in a configuration where panels 10 and 12 (not pictured) are configured in a 270° angle. FIG. 29D shows the device 200 of FIGS. 24B and 24C in a configuration where panels 10 and 12 (not pictured) are configured in a 180 angle.

Figure 30A:
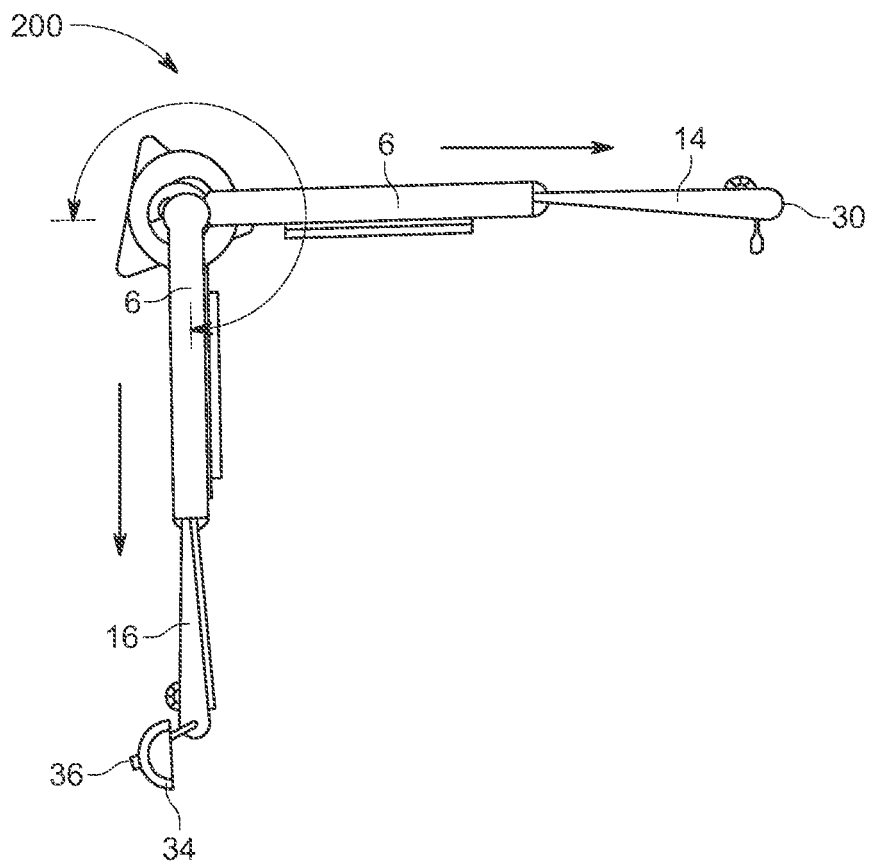
FIGS. 30A and 30B are top views of a device according to an embodiment, and depict rotational capabilities of the device.
Figure 30B:
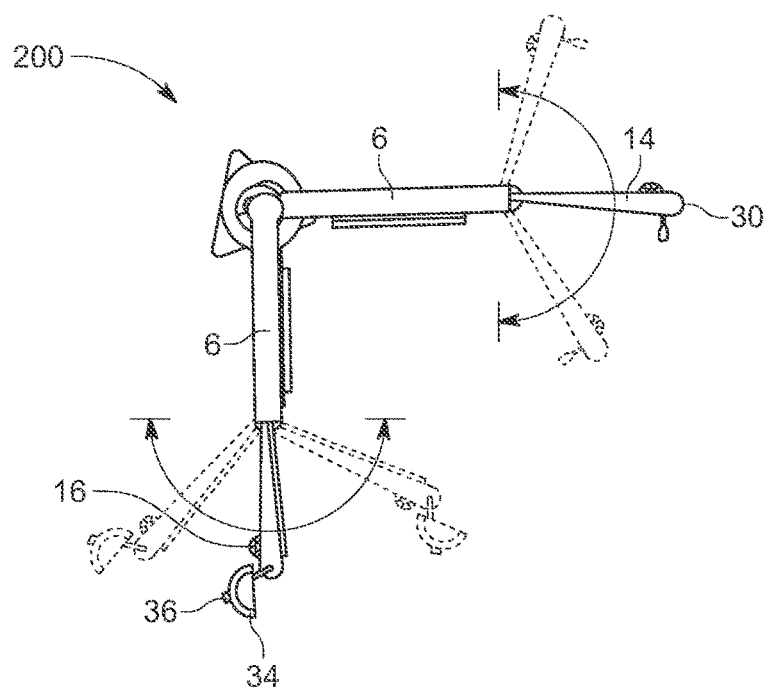

FIGS. 30A and 30B are top views of a device 200 according to an example embodiment, and depict rotational capabilities of the device. FIGS. 30A and 30B depict the device 200 shown in FIGS. 24B and 24C, with additional panels 14 and 16 extended, as in FIGS. 25 and 27. In the embodiment shown in FIG. 30A, additional panels 14 and 16 slide outward along, and extend from first panel 10 and second panel 12 along the direction of the arrows. In the embodiment shown in FIG. 30B, additional panels 14 and 16 are slidingly attached to panels 10 and 12, as in the FIG. 30A embodiment. However, in the embodiment of FIG. 30B, additional panels 14 and 16, upon reaching their fully-extended position, are configured to be able to pivot about the terminal point of attachment to panels 10 and 12, respectively.

Figure 31:
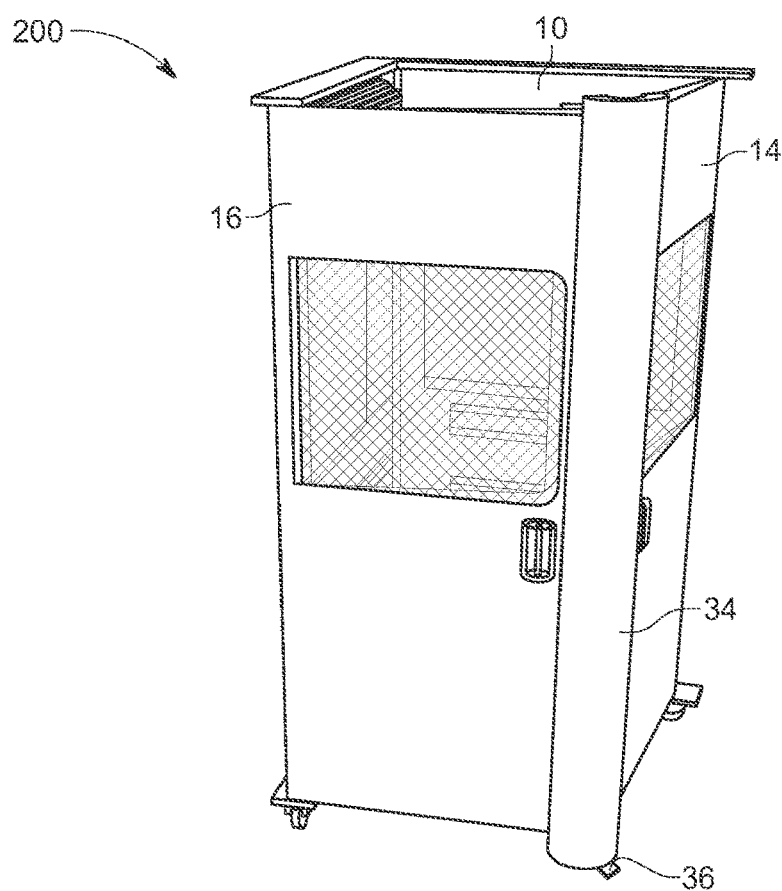
FIG. 31 is a view of a device according to an embodiment in a contained configuration, demonstrating the ability of the device to form an enclosure within itself (e.g., a contained sterilization area).

FIG. 31 is a view of a device 200 according to an embodiment in a contained configuration. In particular, FIG. 8 depicts an embodiment of the device 200 of FIG. 25, where additional panels 14 and 16 are in extended positions. The coupling hinges 30 (not shown) on the inner face of panel 14 align with, and are attached to coupling pins 32 (not shown) on coupling column 34 on additional panel 16, thereby attaching panels 14 and 16 to one another, such that device 200 is configured in a contained configuration.

Figure 32:
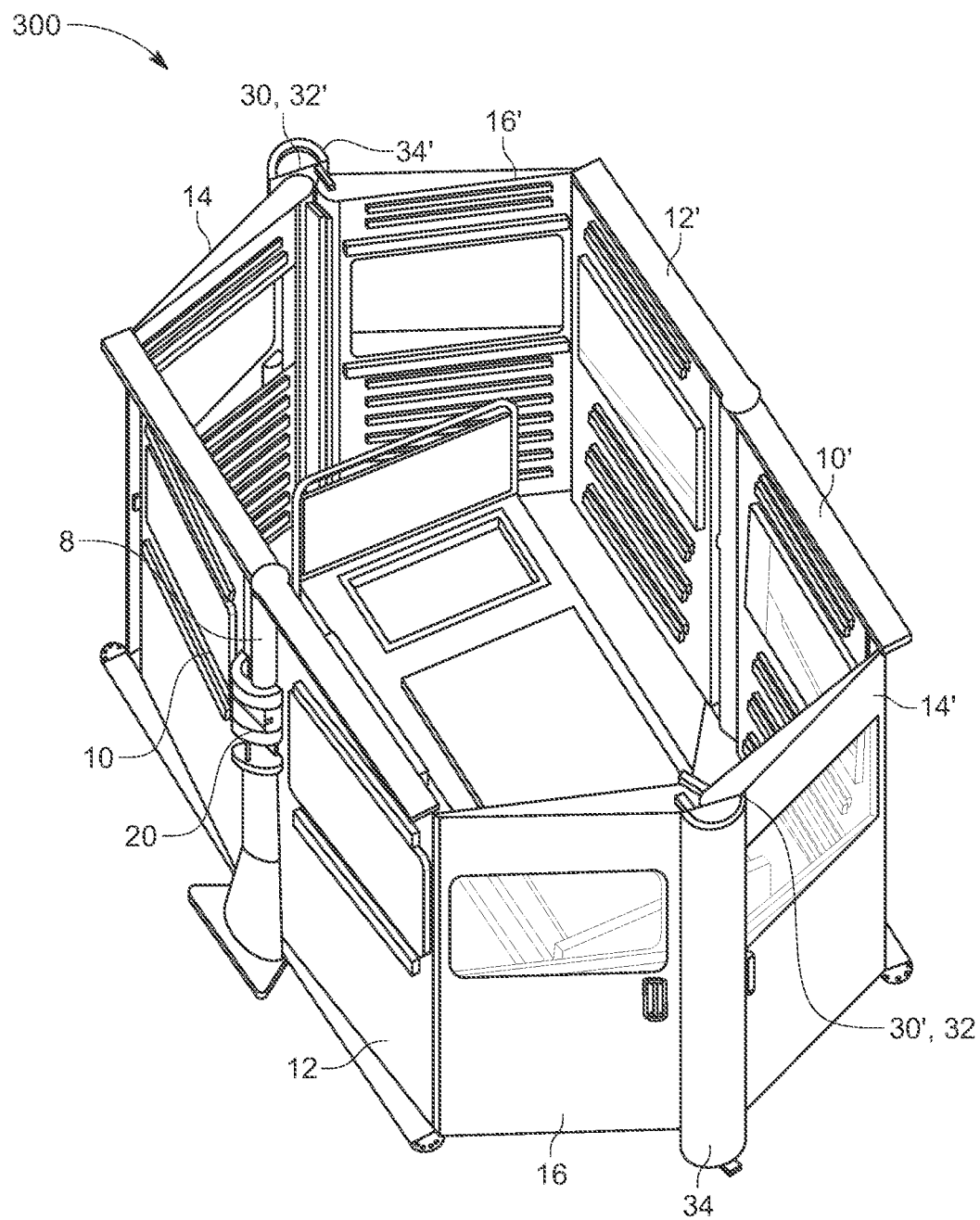
FIG. 32 is a top view of two devices according to an example embodiment in a contained configuration, with a hospital bed depicted therein. The two devices according to the invention are coupled together. One is positioned on the left and one on the right forming a larger enclosure and sterilization volume.

FIG. 32 is a top view of a device 300 according to an embodiment in a contained configuration, with a hospital bed depicted therein. The device 300 comprises two devices 200 as shown in FIG. 25, where the panels, coupling pins, and coupling hinges of one of the devices of FIG. 25 are labeled as described hereinabove, and where the panels, coupling pins, and coupling hinges of the second device of FIG. 25 are labeled as 10', 12', 14', 16', 30', and 32'. As depicted, the two devices 200 are attached via coupling pins 32 and coupling hinges 30' of the first and second devices 200 respectively, and via coupling pins 32' and coupling hinges 30 of the second and first devices 200 respectively (where only one pin and hinge are shown per device 200).

Figure 33:
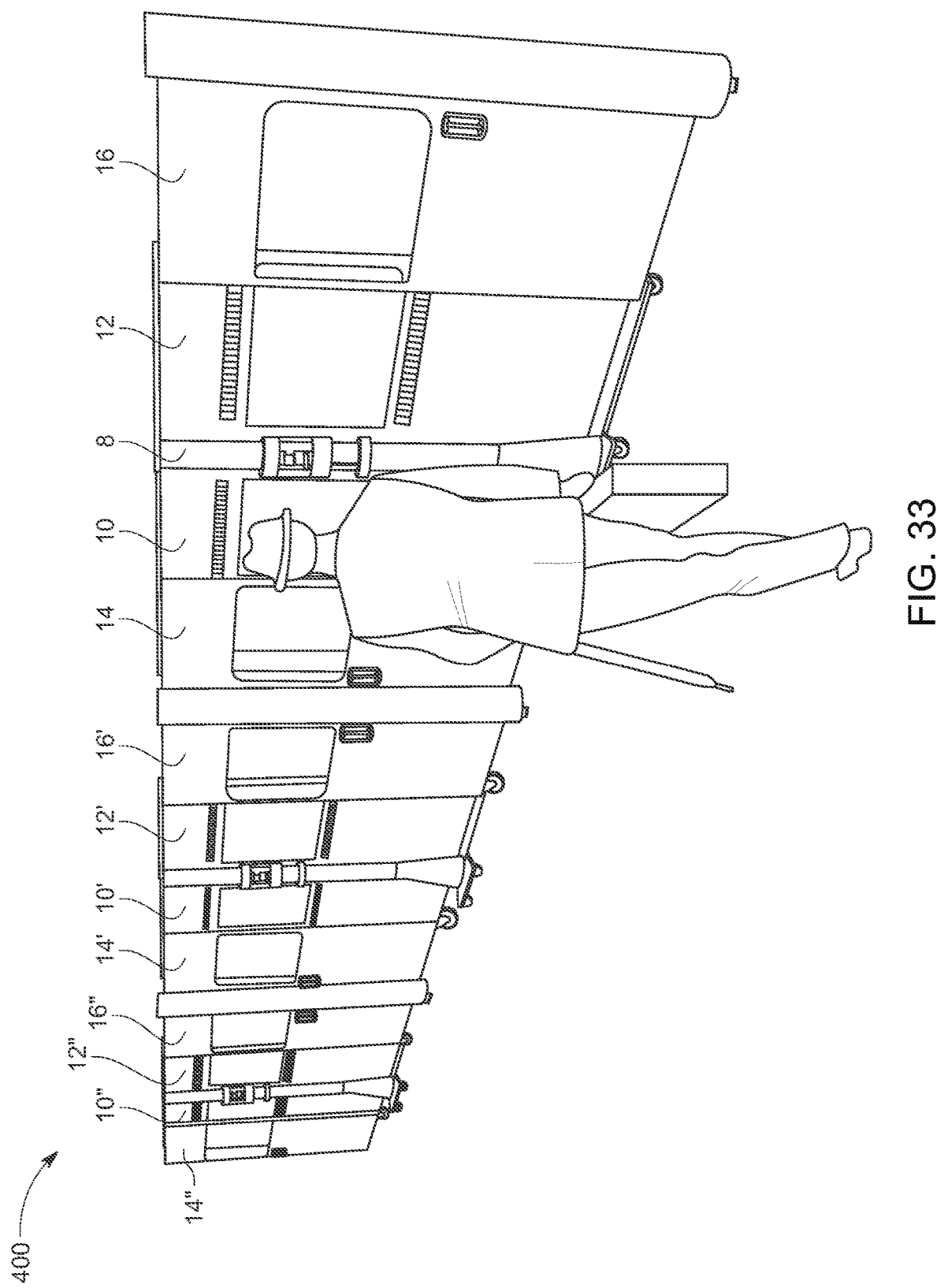
FIG. 33 depicts multiple devices according to an embodiment of the invention, shown in a linear configuration.

FIG. 33 depicts a device 400 according to an example implementation. The device 400 comprises three devices 200 as shown in FIG. 25, where the three devices are attached to each other, and are shown in a linear configuration.

In another aspect, example implementations provide or relate to a method of sterilizing a space, surface, or structure. The method may include exposing the space, surface, or structure to ultraviolet (UV) radiation emitted from the one or more UV-C radiation sources of a device according to the present invention.

In various embodiments, devices and methods of the present invention sterilize or are configured to sterilize one or spaces, one or more surfaces, and/or one or more structures (for example, kill at least 85%, or at least 88% or at least 90% or at least 91%, or at least 92% or at least 93% or at least 94% or at least 95% or at least 96% or at least 97% or at least 98% or at least 99% or at least 99.2% or at least 99.5% or at least 99.9% of pathogens, such as viruses and/or bacteria and/or other pathogens on a structure) by irradiating the target or targets with radiation comprising UV-C radiation. In some embodiments, three-dimensional UV-C irradiation of a target or targets, that is, irradiation from 2 or more directions, for instance, 2 or more orthogonal directions is provided.

Some implementations provide or relate to a method of sterilizing a space, surface, or structure by positioning the device of the invention within about 10 feet or fewer (e.g., 1, 2, 3, 4, 5, 6, 7, 8, 9, or 10 ft) from the space, surface, or structure, and irradiating the space, surface, or structure with UV-C radiation.

The following is a partial list of pathogens killed by example embodiments of the present invention emitting UV-C radiation, and some of the diseases they cause: Bacteriophage (*E. coli*), HIV, Infectious Hepatitis, Influenza (Flu), Poliovirus-Poliomyelitis, Tobacco mosaic, Rotovirus, S *Bacillus anthracis* (Anthrax), *Bacillus magaterium* sp. (Spores), *Bacillus magaterium* sp. (Veg), *Bacillus paratyphusus, Bacillus subtilus* spores, *Bacillus subtilis, Clostridium tetani* (Tetanus/Lockjaw), *Clostridium difficile, Corynebacterium diphtheriae* (Diphtheria), *Eberthella typosa, Escherichia coli* (*E. coli*), *Leptospira* Canicoal-infections (Jaundice), Methicillin-resistant *Staphylococcus Aureus* (MRSA) *Micrococcus candidus, Micrococcus spheroids, Mycobacterium tuberculosis* (Tuberculosis), *Neisseria catarrhalis, Phtomomnas aeruginosa, Pseudomonas fluorescens, Salmonella enteritidis, Salmonella paratyphi* (Enteic Fever), *Salmonella typhosa* (Typhoid Fever), *Salmonella typhimurium, Sarcina lutea, Serratia marcescens, Shigella dysenteriae* (Dysentery), *Shigella flexneri*—(Dysentery), *Shigella paradysenteriae, Spirillum rubrum, Staphylococcus Albus* (Staph), *Staphylococcus Aureus* (Staph), *Streptococcus hemolyticus, Streptococcus lactis, Streptococcus viridians, Vibrio comma*—(Cholera), and mold spores including *Aspergillius flavis, Aspergillius glaucus, Aspergillius niger, Mucor racemosus* A, *Mucor racemosus* B, *Oospora lactis, Penicillium expansum, Penicillium roqueforti, Penicillium digitatum*, and *Rhisophus nigricans*. The effectiveness of aspects of this invention to kill other pathogens will be apparent to those of skill in the art.

As shown in FIG. 34, an implementation of a network environment 3400 for use in controlling and operating one or more sterilization units is shown and described. Any of the components of this environment may be integrated into one or more sterilization units themselves, or provided as one or more entities separate from the sterilization unit or units. In brief overview, referring now to FIG. 34, a block diagram of an exemplary cloud computing environment 3400 is shown and described. The cloud computing environment 3400 may include one or more resource providers 3402a, 3402b, 3402c (collectively, 3402). Each resource provider 3402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 3402 may be connected to any other resource provider 3402 in the cloud computing environment 3400. In some implementations, the resource providers 3402 may be connected over a computer network 3408. Each resource provider 3402 may be connected to one or more computing device 3404*a*, 3404*b*, 3404*c* (collectively, 3404), over the computer network 3408.

The cloud computing environment 3400 may include a resource manager 3406. The resource manager 3406 may be connected to the resource providers 3402 and the computing devices 3404 over the computer network 3408. In some implementations, the resource manager 3406 may facilitate the provision of computing resources by one or more resource providers 3402 to one or more computing devices 3404. The resource manager 3406 may receive a request for a computing resource from a particular computing device 3404. The resource manager 3406 may identify one or more resource providers 3402 capable of providing the computing resource requested by the computing device 3404. The resource manager 3406 may select a resource provider 3402 to provide the computing resource. The resource manager 3406 may facilitate a connection between the resource provider 3402 and a particular computing device 3404. In some implementations, the resource manager 3406 may establish a connection between a particular resource provider 3402 and a particular computing device 3404. In some implementations, the resource manager 3406 may redirect a particular computing device 3404 to a particular resource provider 3402 with the requested computing resource.

FIG. 35 shows an example of a computing device 3500 and a mobile computing device 3550 that can be used to implement the techniques described in this disclosure. The computing device 3500 is intended to represent various forms of digital computers, such as laptops, desktops, workstations, personal digital assistants, servers, blade servers, mainframes, and other appropriate computers. The mobile computing device 3550 is intended to represent various forms of mobile devices, such as personal digital assistants, cellular telephones, smart-phones, and other similar computing devices. The components shown here, their connections and relationships, and their functions, are meant to be examples only, and are not meant to be limiting. The computing devices of FIG. 35 may be, for example, part of the control system of the sterilization units described herein.

The computing device 3500 includes a processor 3502, a memory 3504, a storage device 3506, a high-speed interface 3508 connecting to the memory 3504 and multiple high speed expansion ports 3510, and a low-speed interface 3512 connecting to a low-speed expansion port 3514 and the storage device 3506. Each of the processor 3502, the memory 3504, the storage device 3506, the high-speed interface 3508, the high-speed expansion ports 3510, and the low-speed interface 3512, are interconnected using various busses, and may be mounted on a common motherboard or in other manners as appropriate. The processor 3502 can process instructions for execution within the computing device 3500, including instructions stored in the memory 3504 or on the storage device 3506 to display graphical information for a GUI on an external input/output device, such as a display 3516 coupled to the high-speed interface 3508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 3504 stores information within the computing device 3500. In some implementations, the memory 3504 is a volatile memory unit or units. In some implementations, the memory 3504 is a non-volatile memory unit or units. The memory 3504 may also be another form of computer-readable medium, such as a magnetic or optical disk.

The storage device 3506 is capable of providing mass storage for the computing device 3500. In some implementations, the storage device 3506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 3502), perform one or more methods, such as any of the methods described herein. The instructions can also be stored by one or more storage devices such as computer- or machine-readable mediums (for example, the memory 3504, the storage device 3506, or memory on the processor 3502).

The high-speed interface 3508 manages bandwidth-intensive operations for the computing device 3500, while the low-speed interface 3512 manages lower bandwidth-intensive operations. Such allocation of functions is an example only. In some implementations, the high-speed interface 3508 is coupled to the memory 3504, the display 3516 (e.g., through a graphics processor or accelerator), and to the high-speed expansion ports 3510, which may accept various expansion cards (not shown). In the implementation, the low-speed interface 3512 is coupled to the storage device 3506 and the low-speed expansion port 3514. The low-speed expansion port 3514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 3500 may be implemented in a number of different forms, as shown in the figure. For example, it may be implemented as a standard server 3520, or multiple times in a group of such servers. In addition, it may be implemented in a personal computer such as a laptop computer 3522. It may also be implemented as part of a rack server system 3524. Alternatively, components from the computing device 3500 may be combined with other components in a mobile device (not shown), such as a mobile computing device 3550. Each of such devices may contain one or more of the computing device 3500 and the mobile computing device 3550, and an entire system may be made up of multiple computing devices communicating with each other.

The mobile computing device 3550 includes a processor 3552, a memory 3564, an input/output device such as a display 3554, a communication interface 3566, and a transceiver 3568, among other components. The mobile computing device 3550 may also be provided with a storage device, such as a micro-drive or other device, to provide additional storage. Each of the processor 3552, the memory 3564, the display 3554, the communication interface 3566, and the transceiver 3568, are interconnected using various buses, and several of the components may be mounted on a common motherboard or in other manners as appropriate.

The processor 3552 can execute instructions within the mobile computing device 3550, including instructions stored in the memory 3564. The processor 3552 may be implemented as a chipset of chips that include separate and multiple analog and digital processors. The processor 3552 may provide, for example, for coordination of the other components of the mobile computing device 3550, such as control of user interfaces, applications run by the mobile computing device 3550, and wireless communication by the mobile computing device 3550.

The processor 3552 may communicate with a user through a control interface 3558 and a display interface 3556 coupled to the display 3554. The display 3554 may be, for example, a TFT (Thin-Film-Transistor Liquid Crystal Display) display or an OLED (Organic Light Emitting Diode) display, or other appropriate display technology. The display interface 3556 may comprise appropriate circuitry for driving the display 3554 to present graphical and other information to a user. The control interface 3558 may receive commands from a user and convert them for submission to the processor 3552. In addition, an external interface 3562 may provide communication with the processor 3552, so as to enable near area communication of the mobile computing device 3550 with other devices. The external interface 3562 may provide, for example, for wired communication in some implementations, or for wireless communication in other implementations, and multiple interfaces may also be used.

The memory 3564 stores information within the mobile computing device 3550. The memory 3564 can be implemented as one or more of a computer-readable medium or media, a volatile memory unit or units, or a non-volatile memory unit or units. An expansion memory 3574 may also be provided and connected to the mobile computing device 3550 through an expansion interface 3572, which may include, for example, a SIMM (Single In Line Memory Module) card interface. The expansion memory 3574 may provide extra storage space for the mobile computing device 3550, or may also store applications or other information for the mobile computing device 3550. Specifically, the expansion memory 3574 may include instructions to carry out or supplement the processes described above, and may include secure information also. Thus, for example, the expansion memory 3574 may be provided as a security module for the mobile computing device 3550, and may be programmed with instructions that permit secure use of the mobile computing device 3550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 3552), perform one or more methods, such as those described above. The instructions can also be stored by one or more storage devices, such as one or more computer- or machine-readable mediums (for example, the memory 3564, the expansion memory 3574, or memory on the processor 3552). In some implementations, the instructions can be received in a propagated signal, for example, over the transceiver 3568 or the external interface 3562.

The mobile computing device 3550 may communicate wirelessly through the communication interface 3566, which may include digital signal processing circuitry where necessary. The communication interface 3566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 3568 using a radio-frequency. In addition, short-range communication may occur, such as using a Bluetooth®, Wi-Fin, or other such transceiver (not shown). In addition, a GPS (Global Positioning System) receiver module 3570 may provide additional navigation- and location-related wireless data to the mobile computing device 3550, which may be used as appropriate by applications running on the mobile computing device 3550.

The mobile computing device 3550 may also communicate audibly using an audio codec 3560, which may receive spoken information from a user and convert it to usable digital information. The audio codec 3560 may likewise generate audible sound for a user, such as through a speaker, e.g., in a handset of the mobile computing device 3550. Such sound may include sound from voice telephone calls, may include recorded sound (e.g., voice messages, music files, etc.) and may also include sound generated by applications operating on the mobile computing device 3550.

The mobile computing device 3550 may be implemented in a number of different forms, as shown in the figure. For example, it may be implemented as a cellular telephone 3580. It may also be implemented as part of a smart-phone 3582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for use in controlling and operating one or more sterilization units are provided. Having described certain implementations of methods and apparatus for use in controlling and operating one or more sterilization units, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

The terminology used herein is for the purpose of describing particular embodiments only and is not intended to be limiting of the invention. As used herein, the singular forms "a". "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features.

Furthermore, a device or structure that is configured in a certain way is configured in at least that way, but may also be configured in ways that are not listed.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention. Moreover, the features of the particular examples and embodiments described herein may be used in any combination. The present invention therefore includes variations from the various examples and embodiments described herein, as will be apparent to one of skill in the art.

Example 1—Effect of Multivector UV Energy on Eradication of Medically Important Bacteria and Fungi This Example shows, among other things, how embodiments of the invention may be used in a clinically relevant manner to eradicate bacteria and/or fungi that are of significant medical concern.

Study Design

In this Example, isolates of resistant bacterial pathogens and of pathogenic fungi were exposed to UV energy for various amounts of time (in seconds) and at different distances from the UV sources in the sterilization unit in a given experiment according to the following design.

Referring to FIG. 36, fields with text "UV": cumulatively make up a sterilization unit configured in accordance with the implementation of the present invention shown in FIG. 10, and indicate the approximate location of the UV sources comprising a portion of the sterilization unit; fields marked "P 1" to "P6": cumulatively made up a contaminated field with quantitative culture plates of bacteria or fungi, with each of the cells marked P1-P6 representing a section on the contaminated field. Preparation of the culture plates is described below. Each section P1-P6 contained two culture plates exposed to UV energy for a specific period of time. In this Example, the time points were 5 seconds, 15 seconds, 30 seconds, 60 seconds, 90 seconds, 120 seconds, or 180 seconds.

The number of colonies growing on each plate were counted and plotted as a function of time of (1) UV exposure, (2) distance from the UV energy element, (3) estimated energy of exposure, and (4) time-energy product. UV intensity ranges for a single second in time for the unit in this Example ranged from 1,000-2,500 microWatt/cm$^2$ using this value with the product of time in seconds, values of approximately 26,000 microWatts/cm$^2$*seconds are reached. Without wishing to be held to a particular theory, it is likely that these levels may be sufficient to achieve killing of extremely resistant organisms, for example, Anthrax spores.

Organisms

In this Example, each section P 1-P6 contained 3 isolates each of the following pathogens: methicillin-Resistant *Staphylococcus aureus* (MRSA), vancomycin-resistant *Enterococcus faecium* (VRE), ESBL *Escherichia coli*, carbapenernase-resistant *Klebsiella pneumoniae* (KPC), multi-drug-resistant *Pseudomonas aeruginosa, Acinetobacter* baumannii, C. albicans, C. glabrata, C. parapsilosis, C. krusei, Aspergillus fumigatus, Fusarium solani, and *Scedosporium apiospermum*.

Preparation of Inoculum

The inoculum for the quantitative culture assay was prepared by growing the isolate for 24 hours at 37° C. on Mueller Hinton Agar (MHA), inoculating the samples of 3 colonies into a starter broth of two 50 ml Erlenmeyer flasks of RPMI broth and incubating the broth for 2 hours in a gyratory water bath at 37° C. One hundred microliters (0.1 ml) of this suspension was transferred into 50 ml of fresh RPMI broth in each of two 250-m Erlenmeyer flasks. These flasks were incubated overnight at 37° C. for 16 hours in a gyratory water bath in order to generate logarithmic-phase growth. The suspension was then centrifuged, the pellet washed with normal saline, the concentration adjusted with a hemacytometer, and a serial dilution performed to obtain a suspension of 3,000-2,000 CFU/ml. One hundred microliters (0.1 ml) was then inoculated and spread onto MHA plates with 5% sheep blood for bacteria and potato dextrose plates for fungi.

The plates were then labeled, placed in the UV energy field, exposed to UV energy for one of the aforementioned time periods, and then incubated at 37° C. for 18 hours. The number of colonies on a given plated were then counted and recorded as shown in Table 1.

Statistical Analysis

All experiments were run in triplicate for a given species. Values are expressed as means±SEMs. All groups exposed to UV energy were compared against the unexposed control group by analysis of variance (ANOVA). A two-tailed P value of <0.05, which has already been adjusted for multiple comparisons by Bonferroni's method, is considered to be statistically significant.

Values are expressed as Mean t SEM (Standard error of the mean) of LOG (Cfu/ml) from six different locations of the grid at specific times of exposure to UV energy. Referring to Table 1, below, shaded cells represent time of exposure at which organism is completely cleared from the plates.

What is claimed is:

1. A system for disinfecting objects in a target zone having a perimeter, said system comprising:
    a plurality of UV-C light emitting sources configured to emit a UV-C radiation and disposed on a housing, wherein a first portion of the plurality of UV-C light emitting sources are located on a first panel of the housing and a second portion of the plurality of UV-C light emitting sources are located on a second panel of the housing, and wherein the second panel and the first panel form an angle such that the plurality of UV-C light emitting sources are disposed along at least a portion of the perimeter of the target zone; and
    a control system in communication with the plurality of UV-C light emitting sources, the control system comprising a processor configured to selectively control the plurality of UV-C light emitting sources such that at least some of the first portion of the plurality of UV-C light emitting sources are activated to illuminate the target zone with the UV-C radiation from first direction and such that at least some of the second portion of the plurality of UV-C light emitting sources are activated to illuminate the target zone with the UV-C radiation from a second direction that is different than the first direction, for a targeted amplification of converged multi-vector UV-C light at the target zone.

2. The system of claim 1, wherein the angle between the first panel and the second panel is adjustable.

3. The system of claim 2, wherein the angle is adjustable from a first angle that is less than 5 degrees to a second angle that is greater than 170 degrees.

4. The system of claim 1, wherein the housing comprises a room partition selectably configurable between two or more different partition geometries, wherein the room partition is configured, in each of the two or more different partition geometries, to (a) physically separate floor space of a room into the target zone and a non-target zone, and (b)

TABLE 1

Effect of multivector UV energy on eradication of medically important bacteria and fungi.

| Organisms | Time 0 (no exposure) | Time 5 sec | Time 15 sec | Time 30 sec | Time 60 sec | Time 90 sec | Time 120 sec | Time 180 sec |
|---|---|---|---|---|---|---|---|---|
| Methicillin-resistant *Staphylococcus aureus* (MRSA) | $8.2 \pm 1.4 \times 10^3$ | $1.9 \pm 0.4 \times 10^3$ | 0 | 0 | 0 | 0 | 0 | 0 |
| Vancomycin-resistant *Enterococcus faecium* (VRE) | $1.8 \pm 0.1 \times 10^3$ | $0.8 \pm 0.1 \times 10^3$ | $0.1 \pm 0.02 \times 10^3$ | 0 | 0 | 0 | 0 | 0 |
| ESBL *Escherichia coli* | $1.8 \pm 0.4 \times 10^4$ | $1.0 \pm 0.2 \times 10^3$ | $10 \pm 6$ | 0 | 0 | 0 | 0 | 0 |
| Carbapenemase-resistant *Klebsiella pneumoniae* (KPC) | $7.2 \pm 1.1 \times 10^3$ | $2.1 \pm 0.4 \times 10^3$ | $28 \pm 12$ | $4 \pm 2$ | 0 | 0 | 0 | 0 |
| Multidrug-resistant *Pseudomonas aeruginosa* | $1.5 \pm 0.07 \times 10^3$ | $0.4 \pm 0.1 \times 10^3$ | 0 | 0 | 0 | 0 | 0 | 0 |
| *Acinetobacter baumannii* | $4.2 \pm 0.4 \times 10^3$ | $1.9 \pm 0.2 \times 10^3$ | $38 \pm 10$ | $10 \pm 3$ | 0 | 0 | 0 | 0 |
| *C. albicans* | $3.0 \pm 0.2 \times 10^3$ | $2.8 \pm 0.2 \times 10^3$ | $0.7 \pm 0.1 \times 10^3$ | $32 \pm 13$ | 0 | 0 | 0 | 0 |
| *C. glabrata* | $2.2 \pm 0.2 \times 10^3$ | $0.4 \pm 0.07 \times 10^3$ | $10 \pm 2$ | 0 | 0 | | 0 | 0 |
| *C. parapsilosis* | $2.3 \pm 0.3 \times 10^3$ | $0.3 \pm 0.05 \times 10^3$ | $11 \pm 2$ | 0 | 0 | 0 | 0 | 0 |
| *C. krusei* | $1.9 \pm 0.06 \times 10^3$ | $0.5 \pm 0.1 \times 10^3$ | $37 \pm 15$ | 0 | 0 | 0 | 0 | 0 |
| *Aspergillus fumigatus* | $2.7 \pm 0.1 \times 10^3$ | $2.7 \pm 0.1 \times 10^3$ | $2.2 \pm 0.1 \times 10^3$ | $1.2 \pm 0.1 \times 10^3$ | $0.1 \pm 0.03 \times 10^3$ | $10 \pm 2$ | 0 | 0 |
| *Fusarium solani* | $1.7 \pm 0.1 \times 10^3$ | $1.1 \pm 0.2 \times 10^3$ | $0.3 \pm 0.1 \times 10^3$ | 0 | 0 | 0 | 0 | 0 |
| *Scedosporium apiospermum* | $1.8 \pm 0.1 \times 10^3$ | $0.3 \pm 0.05 \times 10^3$ | $12 \pm 5$ | 0 | 0 | 0 | 0 | 0 | direct the UV-C radiation to the target zone from at least two different directions while shielding the non-target zone from the UV-C radiation.

5. The system of claim 4, wherein the first panel and the second panel are configured to form a UV-C barrier between the target zone and the non-target zone and each having a first face configured to face toward the non-target zone and a second face configured to face toward the target zone.

6. The system of claim 4, wherein the room partition includes casters such that the room partition can be rolled between multiple configurations.

7. The system of claim 1, further comprising: a third panel including a first side, and an opposite second side configured to direct a third portion of the UV-C radiation outwardly from the opposite second side, the third panel configured to block the UV-C from passing outwardly from the first side of the third panel, wherein the third panel is coupled to the first panel and slideable along a width of the first panel between a proximal position and a distal position.

8. The system of claim 7, further comprising: a slide mechanism via which the third panel is coupled to the first panel, wherein the slide mechanism comprises a track and a slide block configured to move along the track.

9. The system of claim 8, wherein the slide block is configured to rotate relative to the track to allow the third panel to rotate relative to the first panel in a plane that includes the third panel.

10. The system of claim 9, wherein the third panel has a range of rotation of greater than 3 degrees relative to the first panel.

11. The system of claim 7, further comprising a fourth panel including a first side, and an opposite second side configured to direct a fourth portion of the UV-C radiation outwardly from the second side, the fourth panel configured to block the UV-C radiation from passing outwardly from the first side.

12. The system of claim 11, wherein the housing is configurable into a multi-walled enclosure having four walls, wherein each of the first panel, the second panel, the third panel, and the fourth panel corresponds to a respective one of the four walls such that the second side of each of the first panel, the second panel, the third panel, and the fourth panel is directed to an interior of the multi-walled enclosure.

13. The system of claim 1, wherein the control system comprises at least one computer processor configured to adjust an intensity and a duration of the UV-C light emitting sources for the UV-C radiation.

14. The system of claim 13, wherein the at least one computer processor is configured to adjust power supplied to the UV-C light emitting sources based on age-based degradation of the UV-C light emitting sources in order to provide consistency of UV-C intensity from the UV-C light emitting sources.

15. The system of claim 13, wherein the at least one computer processor is configured to receive a signal from one or more sensors configured to measure UV-C exposure in the target zone.

16. The system of claim 15, wherein the control system further comprises a transceiver configured to send and receive information over a communication network.

17. The system of claim 16, wherein the control system is configured to transmit information providing an identity of at least one of (a) an item in the target zone and (b) a location of the target zone.

18. The system of claim 17, wherein the transmitted information indicates that the item or target zone location has been exposed to the UV-C radiation by the UV-C light emitting sources.

19. The system of claim 16, wherein the at least one computer processor is configured to receive via the transceiver and process information that identifies the target zone or an item that has been flagged as needing exposure to the UV-C radiation.

20. The system of claim 1, wherein at least one of the first panel and the second panel includes a window configured to allow visual inspection of an area to be illuminated with UV-C radiation from a position that is not exposed to the UV-C radiation generated by the UV-C light emitting sources.

21. A system for disinfecting objects in a target zone having a perimeter, said system comprising:
a plurality of UV-C light emitting sources configured to emit a UV-C radiation and disposed on a housing, wherein a first portion of the plurality of UV-C light emitting sources are located on a first panel of the housing and a second portion of the plurality of UV-C light emitting sources are located on a second panel of the housing, and wherein the second panel and the first panel form an angle such that the plurality of UV-C light emitting sources are disposed along at least a portion of the perimeter of the target zone;
a memory storing machine-readable instructions; and
a control system in communication with the plurality of UV-C light emitting sources, the control system comprising a processor that is configured to execute the machine-readable instructions to:
illuminate the target zone from a first direction with UV-C light emitted from at least some of the first portion of the plurality of UV light emitting sources;
illuminate the target zone from a second direction with UV-C light emitted from at least some of the second portion of the plurality of UV light emitting sources, the second direction being different than the first direction;
focus the UV-C light from the first direction and the second direction to achieve a targeted amplification of converged multivector UV light.

* * * * *